(12) United States Patent
Gertner

(10) Patent No.: US 9,125,642 B2
(45) Date of Patent: Sep. 8, 2015

(54) EXTERNAL AUTONOMIC MODULATION

(71) Applicant: Kona Medical, Inc., Palo Alto, CA (US)

(72) Inventor: Michael Gertner, Menlo Park, CA (US)

(73) Assignee: Kona Medical, Inc., Bellevue, WA (US)

( * ) Notice: Subject to any disclaimer, the term of this patent is extended or adjusted under 35 U.S.C. 154(b) by 96 days.

(21) Appl. No.: 14/099,834

(22) Filed: Dec. 6, 2013

(65) Prior Publication Data
US 2014/0236048 A1 Aug. 21, 2014

Related U.S. Application Data

(63) Continuation of application No. 12/725,450, filed on Mar. 16, 2010, which is a continuation-in-part of application No. 12/685,655, filed on Jan. 11, 2010, now Pat. No. 8,295,912.

(Continued)

(51) Int. Cl.
A61B 8/06 (2006.01)
A61B 18/04 (2006.01)
A61N 7/02 (2006.01)
(Continued)

(52) U.S. Cl.
CPC . *A61B 18/04* (2013.01); *A61B 8/06* (2013.01); *A61B 8/0841* (2013.01); *A61N 7/00* (2013.01); *A61N 7/02* (2013.01); *A61B 6/506* (2013.01); *A61B 8/0833* (2013.01); *A61B 8/4245* (2013.01); *A61B 8/485* (2013.01); *A61B 19/5244* (2013.01); *A61B 2018/00982* (2013.01); *A61B 2019/5236* (2013.01); *A61B 2019/5276* (2013.01); *A61N 7/022* (2013.01); *A61N 2007/003* (2013.01); *A61N 2007/0026* (2013.01);
(Continued)

(58) Field of Classification Search
CPC .......... A61B 2018/00434; A61B 2018/00511; A61B 2019/5276; A61B 6/506; A61B 5/055; A61B 5/489; A61B 5/4893; A61B 18/14; A61N 7/02; A61N 7/00; A61N 2007/0026
USPC ........................................................ 601/2–4
See application file for complete search history.

(56) References Cited

U.S. PATENT DOCUMENTS 385,256 A 6/1888 Eggers
3,274,437 A 9/1966 Mastrup
(Continued)

FOREIGN PATENT DOCUMENTS

EP 0225120 A2 6/1987
EP 0420758 A1 4/1991
(Continued)

OTHER PUBLICATIONS

International Search Report and Written Opinion dated Jul. 27, 2011 for PCT/US2011/033337.

(Continued)

*Primary Examiner* — Mark Remaly
(74) *Attorney, Agent, or Firm* — Vista IP Law Group, LLP

(57) ABSTRACT

In some embodiments, nerves surrounding arteries or leading to organs are targeted with energy sources to correct or modulate physiologic processes. In some embodiments, different types of energy sources are utilized singly or combined with one another. In some embodiments, bioactive agents or devices activated by the energy sources are delivered to the region of interest and the energy is enhanced by such agents.

20 Claims, 27 Drawing Sheets

Related U.S. Application Data

(60) Provisional application No. 61/303,307, filed on Feb. 10, 2010, provisional application No. 61/256,983, filed on Oct. 31, 2009, provisional application No. 61/250,857, filed on Oct. 12, 2009, provisional application No. 61/261,741, filed on Nov. 16, 2009, provisional application No. 61/291,359, filed on Dec. 30, 2009, provisional application No. 61/256,983, filed on Oct. 31, 2009, provisional application No. 61/250,857, filed on Oct. 12, 2009, provisional application No. 61/261,741, filed on Nov. 16, 2009, provisional application No. 61/291,359, filed on Dec. 30, 2009.

(51) Int. Cl.
*A61B 8/08* (2006.01)
*A61B 19/00* (2006.01)
*A61N 7/00* (2006.01)
*A61B 18/00* (2006.01)
*A61B 6/00* (2006.01)
*A61B 8/00* (2006.01)

(52) U.S. Cl.
CPC ............... *A61N 2007/0039* (2013.01); *A61N 2007/0078* (2013.01); *A61N 2007/025* (2013.01)

(56) References Cited

U.S. PATENT DOCUMENTS

| | | |
|---|---|---|
| 3,499,437 A | 3/1970 | Balamuth |
| 3,552,382 A | 1/1971 | Mount |
| 3,847,016 A | 11/1974 | Ziedonis |
| 3,927,662 A | 12/1975 | Ziedonis |
| 4,059,098 A | 11/1977 | Murdock |
| 4,167,180 A | 9/1979 | Kossoff |
| 4,197,856 A | 4/1980 | Northrop |
| 4,206,763 A | 6/1980 | Pendersen |
| 4,237,901 A | 12/1980 | Taenzer |
| 4,273,127 A | 6/1981 | Auth et al. |
| 4,469,099 A | 9/1984 | McEwen |
| 4,479,494 A | 10/1984 | McEwen |
| 4,484,569 A | 11/1984 | Driller et al. |
| 4,545,386 A | 10/1985 | Hetz et al. |
| 4,601,296 A | 7/1986 | Yerushalmi |
| 4,605,010 A | 8/1986 | McEwen |
| 4,688,578 A | 8/1987 | Takano et al. |
| 4,702,732 A | 10/1987 | Powers et al. |
| 4,708,836 A | 11/1987 | Gain et al. |
| 4,748,985 A | 6/1988 | Nagasaki |
| 4,757,820 A | 7/1988 | Itoh |
| 4,770,175 A | 9/1988 | McEwen |
| 4,773,865 A | 9/1988 | Baldwin |
| 4,773,899 A | 9/1988 | Spears |
| 4,784,148 A | 11/1988 | Dow et al. |
| 4,841,979 A | 6/1989 | Dow et al. |
| 4,850,363 A | 7/1989 | Yanagawa |
| 4,858,613 A | 8/1989 | Fry et al. |
| 4,905,672 A | 3/1990 | Schwarze et al. |
| 4,913,155 A | 4/1990 | Dow et al. |
| 4,929,246 A | 5/1990 | Sinofsky |
| 4,931,047 A | 6/1990 | Broadwin et al. |
| 4,938,216 A | 7/1990 | Lele |
| 4,938,217 A | 7/1990 | Lele |
| 4,957,099 A | 9/1990 | Hassler |
| 4,957,481 A | 9/1990 | Gatenby |
| 5,005,579 A | 4/1991 | Wurster et al. |
| RE33,590 E | 5/1991 | Dory |
| 5,026,387 A | 6/1991 | Thomas |
| 5,036,855 A | 8/1991 | Fry et al. |
| 5,039,774 A | 8/1991 | Shikinami et al. |
| 5,042,486 A | 8/1991 | Pfeiler et al. |
| 5,065,742 A | 11/1991 | Belikan et al. |
| 5,080,101 A | 1/1992 | Dory |
| 5,080,102 A | 1/1992 | Dory |
| 5,150,712 A | 9/1992 | Dory |
| 5,170,790 A | 12/1992 | Lacoste et al. |
| 5,178,135 A | 1/1993 | Uchiyama et al. |
| 5,178,148 A | 1/1993 | Lacoste et al. |
| 5,181,522 A | 1/1993 | McEwen |
| 5,193,527 A | 3/1993 | Schaefer |
| 5,194,291 A | 3/1993 | D'Aoust et al. |
| 5,211,160 A | 5/1993 | Talish et al. |
| 5,215,680 A | 6/1993 | D'Arrigo |
| 5,219,401 A | 6/1993 | Cathignol et al. |
| 5,230,334 A | 7/1993 | Klopotek |
| 5,230,921 A | 7/1993 | Waltonen et al. |
| 5,233,994 A | 8/1993 | Shmulewitz |
| 5,243,988 A | 9/1993 | Sieben et al. |
| 5,254,087 A | 10/1993 | McEwen |
| 5,263,957 A | 11/1993 | Davison |
| 5,290,278 A | 3/1994 | Anderson |
| 5,311,869 A | 5/1994 | Okazaki |
| 5,312,431 A | 5/1994 | McEwen |
| 5,352,195 A | 10/1994 | McEwen |
| 5,364,389 A | 11/1994 | Anderson |
| 5,383,896 A | 1/1995 | Gershony et al. |
| 5,391,140 A | 2/1995 | Schaetzle et al. |
| 5,391,197 A | 2/1995 | Burdette et al. |
| 5,394,877 A | 3/1995 | Orr et al. |
| 5,413,550 A | 5/1995 | Castel |
| 5,415,657 A | 5/1995 | Taymor-Luria |
| 5,439,477 A | 8/1995 | McEwen |
| 5,445,608 A | 8/1995 | Chen et al. |
| 5,453,576 A | 9/1995 | Krivitski |
| 5,454,373 A | 10/1995 | Koger et al. |
| 5,454,831 A | 10/1995 | McEwen |
| 5,471,988 A | 12/1995 | Fujio et al. |
| 5,474,071 A | 12/1995 | Chapelon et al. |
| 5,492,126 A | 2/1996 | Hennige et al. |
| 5,501,655 A | 3/1996 | Rolt et al. |
| 5,503,152 A | 4/1996 | Oakley et al. |
| 5,507,744 A | 4/1996 | Tay et al. |
| 5,507,790 A | 4/1996 | Weiss |
| 5,515,853 A | 5/1996 | Smith et al. |
| 5,520,188 A | 5/1996 | Hennige et al. |
| 5,522,878 A | 6/1996 | Montecalvo et al. |
| 5,524,620 A | 6/1996 | Rosenschein |
| 5,526,815 A | 6/1996 | Granz et al. |
| 5,534,232 A | 7/1996 | Denes et al. |
| 5,536,489 A | 7/1996 | Lohrmann et al. |
| 5,553,618 A | 9/1996 | Suzuki et al. |
| 5,556,415 A | 9/1996 | McEwen et al. |
| 5,558,092 A | 9/1996 | Unger et al. |
| 5,573,497 A | 11/1996 | Chapelon |
| 5,578,055 A | 11/1996 | McEwen |
| 5,584,853 A | 12/1996 | McEwen |
| 5,598,845 A | 2/1997 | Chandraratna et al. |
| 5,601,526 A | 2/1997 | Chapelon et al. |
| 5,607,447 A | 3/1997 | McEwen et al. |
| 5,609,485 A | 3/1997 | Bergman et al. |
| 5,626,601 A | 5/1997 | Gershony et al. |
| 5,630,837 A | 5/1997 | Crowley |
| 5,638,823 A | 6/1997 | Akay et al. |
| 5,643,179 A | 7/1997 | Fujimoto |
| 5,649,954 A | 7/1997 | McEwen |
| 5,655,538 A | 8/1997 | Lorraine et al. |
| 5,657,760 A | 8/1997 | Ying et al. |
| 5,665,073 A | 9/1997 | Bulow et al. |
| 5,666,954 A | 9/1997 | Chapelon et al. |
| 5,681,339 A | 10/1997 | McEwen et al. |
| 5,685,307 A | 11/1997 | Holland et al. |
| 5,695,493 A | 12/1997 | Nakajima et al. |
| 5,697,897 A | 12/1997 | Buchholtz et al. |
| D389,574 S | 1/1998 | Emerson et al. |
| 5,711,058 A | 1/1998 | Frey et al. |
| 5,716,374 A | 2/1998 | Francese et al. |
| 5,720,286 A | 2/1998 | Chapelon et al. |
| 5,720,287 A | 2/1998 | Chapelon et al. |
| 5,722,411 A | 3/1998 | Suzuki |
| 5,726,066 A | 3/1998 | Choi |
| 5,735,796 A | 4/1998 | Granz et al. |
| 5,738,635 A | 4/1998 | Chapelon et al. |

(56) References Cited

U.S. PATENT DOCUMENTS

| | | |
|---|---|---|
| 5,741,295 A | 4/1998 | McEwen |
| 5,755,228 A | 5/1998 | Wilson et al. |
| 5,762,066 A | 6/1998 | Law et al. |
| 5,769,790 A | 6/1998 | Watkins et al. |
| 5,788,636 A | 8/1998 | Curley |
| 5,807,285 A | 9/1998 | Vaitekunas |
| 5,810,007 A | 9/1998 | Holupka et al. |
| 5,810,810 A | 9/1998 | Tay et al. |
| 5,817,021 A | 10/1998 | Reichenberger |
| 5,823,962 A | 10/1998 | Schaetzle et al. |
| 5,824,015 A | 10/1998 | Sawyer |
| 5,824,277 A | 10/1998 | Campos |
| 5,827,204 A | 10/1998 | Grandia et al. |
| 5,827,268 A | 10/1998 | Laufer |
| 5,833,647 A | 11/1998 | Edwards |
| 5,840,028 A | 11/1998 | Chubachi et al. |
| 5,846,517 A | 12/1998 | Unger |
| 5,852,860 A | 12/1998 | Lorraine et al. |
| 5,853,752 A | 12/1998 | Unger et al. |
| 5,855,589 A | 1/1999 | McEwen et al. |
| 5,873,828 A | 2/1999 | Fujio et al. |
| 5,873,845 A | 2/1999 | Cline et al. |
| 5,879,314 A | 3/1999 | Peterson et al. |
| 5,882,302 A | 3/1999 | Driscoll, Jr. et al. |
| 5,882,328 A | 3/1999 | Levy et al. |
| 5,895,356 A | 4/1999 | Andrus et al. |
| 5,904,659 A | 5/1999 | Duarte et al. |
| 5,906,580 A | 5/1999 | Kline-Schoder et al. |
| 5,911,735 A | 6/1999 | McEwen |
| 5,919,139 A | 7/1999 | Lin |
| 5,921,994 A | 7/1999 | Andreas et al. |
| 5,922,945 A | 7/1999 | Allmaras et al. |
| 5,931,786 A | 8/1999 | Whitmore, III et al. |
| 5,931,853 A | 8/1999 | McEwen |
| 5,935,144 A | 8/1999 | Estabrook |
| 5,935,146 A | 8/1999 | McEwen |
| 5,935,339 A | 8/1999 | Henderson et al. |
| 5,938,600 A | 8/1999 | Van Vaals et al. |
| 5,951,476 A | 9/1999 | Beach |
| 5,957,849 A | 9/1999 | Munro |
| 5,964,782 A | 10/1999 | Lafontaine et al. |
| 5,976,092 A | 11/1999 | Chinn |
| 5,979,453 A | 11/1999 | Savage et al. |
| 5,993,389 A | 11/1999 | Driscoll, Jr. et al. |
| 5,997,481 A | 12/1999 | Adams et al. |
| 6,007,499 A | 12/1999 | Martin et al. |
| 6,014,473 A | 1/2000 | Hossack et al. |
| 6,033,506 A | 3/2000 | Klett |
| 6,036,650 A | 3/2000 | Wu et al. |
| 6,037,032 A | 3/2000 | Klett et al. |
| 6,039,694 A | 3/2000 | Larson et al. |
| 6,050,943 A | 4/2000 | Slayton et al. |
| 6,067,371 A | 5/2000 | Gouge et al. |
| 6,068,596 A | 5/2000 | Weth et al. |
| 6,071,239 A | 6/2000 | Cribbs et al. |
| 6,071,277 A | 6/2000 | Farley et al. |
| 6,078,831 A | 6/2000 | Belef et al. |
| 6,083,159 A | 7/2000 | Driscoll, Jr. et al. |
| 6,087,761 A | 7/2000 | Lorraine et al. |
| 6,102,860 A | 8/2000 | Mooney |
| 6,106,463 A | 8/2000 | Wilk |
| 6,120,453 A | 9/2000 | Sharp |
| 6,128,522 A | 10/2000 | Acker et al. |
| 6,179,831 B1 | 1/2001 | Bliweis |
| 6,182,341 B1 | 2/2001 | Talbot et al. |
| 6,200,539 B1 | 3/2001 | Sherman et al. |
| 6,206,843 B1 | 3/2001 | Iger et al. |
| 6,213,939 B1 | 4/2001 | McEwen |
| 6,217,530 B1 | 4/2001 | Martin et al. |
| 6,221,015 B1 | 4/2001 | Yock |
| 6,231,507 B1 | 5/2001 | Zikorus et al. |
| 6,233,477 B1 | 5/2001 | Chia et al. |
| 6,246,156 B1 | 6/2001 | Takeuchi et al. |
| 6,254,601 B1 | 7/2001 | Burbank et al. |
| 6,259,945 B1 | 7/2001 | Epstein et al. |
| 6,263,551 B1 | 7/2001 | Lorraine et al. |
| 6,267,734 B1 | 7/2001 | Ishibashi et al. |
| 6,270,458 B1 | 8/2001 | Barnea |
| 6,277,077 B1 | 8/2001 | Brisken et al. |
| 6,315,441 B2 | 11/2001 | King |
| 6,332,089 B1 | 12/2001 | Acker et al. |
| 6,361,496 B1 | 3/2002 | Zikorus et al. |
| 6,361,548 B1 | 3/2002 | McEwen |
| 6,399,149 B1 | 6/2002 | Klett et al. |
| 6,406,759 B1 | 6/2002 | Roth |
| 6,409,720 B1 | 6/2002 | Hissong et al. |
| 6,419,669 B1 | 7/2002 | Frazier et al. |
| 6,425,867 B1 | 7/2002 | Vaezy et al. |
| 6,425,876 B1 | 7/2002 | Frangi et al. |
| 6,432,067 B1 | 8/2002 | Martin et al. |
| 6,443,894 B1 | 9/2002 | Sumanaweera et al. |
| 6,453,526 B2 | 9/2002 | Lorraine et al. |
| 6,488,639 B1 | 12/2002 | Ribault et al. |
| 6,491,672 B2 | 12/2002 | Slepian et al. |
| 6,494,848 B1 | 12/2002 | Sommercorn et al. |
| 6,500,133 B2 | 12/2002 | Martin et al. |
| 6,506,171 B1 | 1/2003 | Vitek et al. |
| 6,514,221 B2 | 2/2003 | Hynynen et al. |
| 6,520,915 B1 | 2/2003 | Lin et al. |
| 6,522,926 B1 | 2/2003 | Kieval et al. |
| 6,548,047 B1 | 4/2003 | Unger |
| 6,551,576 B1 | 4/2003 | Unger et al. |
| 6,559,644 B2 | 5/2003 | Froundlich et al. |
| 6,562,037 B2 | 5/2003 | Paton et al. |
| 6,565,557 B1 | 5/2003 | Sporri et al. |
| 6,576,168 B2 | 6/2003 | Hardcastle et al. |
| 6,584,360 B2 | 6/2003 | Francischelli et al. |
| 6,595,934 B1 | 7/2003 | Hissong et al. |
| 6,599,256 B1 | 7/2003 | Acker et al. |
| 6,599,288 B2 | 7/2003 | Maguire |
| 6,602,251 B2 | 8/2003 | Burbank et al. |
| 6,612,988 B2 | 9/2003 | Maor et al. |
| 6,616,624 B1 | 9/2003 | Kieval |
| 6,626,855 B1 | 9/2003 | Weng et al. |
| 6,633,658 B1 | 10/2003 | Dabney et al. |
| 6,652,461 B1 | 11/2003 | Levkovitz |
| 6,656,131 B2 | 12/2003 | Alster et al. |
| 6,656,136 B1 | 12/2003 | Weng et al. |
| 6,676,601 B1 | 1/2004 | Lacoste et al. |
| 6,682,483 B1 | 1/2004 | Abend et al. |
| 6,685,639 B1 | 2/2004 | Wang et al. |
| 6,706,892 B1 | 3/2004 | Ezrin et al. |
| 6,709,392 B1 | 3/2004 | Salgo et al. |
| 6,709,407 B2 | 3/2004 | Fatemi |
| 6,716,184 B2 | 4/2004 | Vaezy et al. |
| 6,719,694 B2 | 4/2004 | Weng et al. |
| 6,719,699 B2 | 4/2004 | Smith |
| 6,726,627 B1 | 4/2004 | Lizzi et al. |
| 6,728,566 B1 | 4/2004 | Subramanyan et al. |
| 6,735,461 B2 | 5/2004 | Vitek et al. |
| 6,755,789 B2 | 6/2004 | Stringer et al. |
| 6,764,488 B1 | 7/2004 | Burbank et al. |
| 6,846,291 B2 | 1/2005 | Smith et al. |
| 6,875,176 B2 | 4/2005 | Mourad et al. |
| 6,875,420 B1 | 4/2005 | Quay |
| 6,905,498 B2 | 6/2005 | Hooven |
| 6,932,771 B2 | 8/2005 | Whitmore et al. |
| 6,955,648 B2 | 10/2005 | Mozayeni et al. |
| 6,978,174 B2 | 12/2005 | Gelfand et al. |
| 7,022,077 B2 | 4/2006 | Mourad et al. |
| 7,052,463 B2 | 5/2006 | Peszynski et al. |
| 7,063,666 B2 | 6/2006 | Weng et al. |
| 7,128,711 B2 | 10/2006 | Medan et al. |
| 7,149,564 B2 | 12/2006 | Vining et al. |
| 7,162,303 B2 | 1/2007 | Levin et al. |
| 7,211,060 B1 | 5/2007 | Talish et al. |
| 7,260,250 B2 | 8/2007 | Summers et al. |
| 7,285,093 B2 | 10/2007 | Anisimov et al. |
| 7,374,538 B2 | 5/2008 | Nightingale et al. |
| 7,445,599 B2 | 11/2008 | Kelly et al. |
| 7,470,241 B2 | 12/2008 | Weng et al. |
| 7,499,748 B2 | 3/2009 | Moffitt et al. |
| 7,510,536 B2 | 3/2009 | Foley et al. |
| 7,530,958 B2 | 5/2009 | Slayton et al. |

(56) References Cited

U.S. PATENT DOCUMENTS

| | | | |
|---|---|---|---|
| 7,534,209 B2 | 5/2009 | Abend | |
| 7,553,284 B2 | 6/2009 | Vaitekunas | |
| 7,617,005 B2 | 11/2009 | Demarais et al. | |
| 7,620,451 B2 | 11/2009 | Demarais et al. | |
| 7,628,764 B2 | 12/2009 | Duarte et al. | |
| 7,684,865 B2 | 3/2010 | Aldrich et al. | |
| 7,697,972 B2 | 4/2010 | Verard et al. | |
| 7,698,947 B2 | 4/2010 | Sarr | |
| 7,783,358 B2 | 8/2010 | Aldrich et al. | |
| 8,295,912 B2 | 10/2012 | Gertner | |
| 8,347,891 B2 | 1/2013 | Demarais et al. | |
| 8,383,671 B1 | 2/2013 | Consigny | |
| 8,556,834 B2 | 10/2013 | Gertner | |
| 8,715,209 B2 | 5/2014 | Gertner | |
| 2001/0014775 A1 | 8/2001 | Koger et al. | |
| 2001/0014805 A1 | 8/2001 | Burbank et al. | |
| 2001/0032382 A1 | 10/2001 | Lorraine et al. | |
| 2001/0041910 A1 | 11/2001 | McEwen | |
| 2001/0044636 A1 | 11/2001 | Pedros et al. | |
| 2002/0055736 A1 | 5/2002 | Horn et al. | |
| 2002/0072672 A1 | 6/2002 | Roundhill et al. | |
| 2002/0095164 A1 | 7/2002 | Andreas et al. | |
| 2002/0193831 A1 | 12/2002 | Smith, III | |
| 2003/0009194 A1 | 1/2003 | Saker et al. | |
| 2003/0018255 A1 | 1/2003 | Martin et al. | |
| 2003/0036771 A1 | 2/2003 | McEwen | |
| 2003/0050665 A1 | 3/2003 | Ginn | |
| 2003/0060737 A1* | 3/2003 | Brisken | 601/2 |
| 2003/0069569 A1 | 4/2003 | Burdette et al. | |
| 2003/0114756 A1 | 6/2003 | Li | |
| 2003/0120204 A1 | 6/2003 | Unger et al. | |
| 2003/0149366 A1 | 8/2003 | Stringer et al. | |
| 2003/0153849 A1 | 8/2003 | Huckle et al. | |
| 2003/0187371 A1 | 10/2003 | Vortman et al. | |
| 2003/0195420 A1 | 10/2003 | Mendlein et al. | |
| 2003/0208101 A1 | 11/2003 | Cecchi | |
| 2003/0216792 A1 | 11/2003 | Levin et al. | |
| 2003/0225331 A1 | 12/2003 | Diederich et al. | |
| 2004/0002654 A1 | 1/2004 | Davidson et al. | |
| 2004/0030227 A1 | 2/2004 | Littrup et al. | |
| 2004/0030268 A1 | 2/2004 | Weng et al. | |
| 2004/0030269 A1 | 2/2004 | Horn et al. | |
| 2004/0039280 A1 | 2/2004 | Wu et al. | |
| 2004/0049105 A1 | 3/2004 | Crutchfield et al. | |
| 2004/0054287 A1 | 3/2004 | Stephens | |
| 2004/0054289 A1 | 3/2004 | Eberle et al. | |
| 2004/0071664 A1 | 4/2004 | McHale et al. | |
| 2004/0078034 A1 | 4/2004 | Acker et al. | |
| 2004/0078219 A1 | 4/2004 | Kaylor et al. | |
| 2004/0082978 A1 | 4/2004 | Harrison et al. | |
| 2004/0097805 A1 | 5/2004 | Verard et al. | |
| 2004/0097840 A1 | 5/2004 | Holmer | |
| 2004/0106880 A1 | 6/2004 | Weng et al. | |
| 2004/0113524 A1 | 6/2004 | Baumgartner et al. | |
| 2004/0122493 A1 | 6/2004 | Ishibashi et al. | |
| 2004/0127798 A1 | 7/2004 | Dala-Krishna et al. | |
| 2004/0153126 A1 | 8/2004 | Okai | |
| 2004/0158154 A1 | 8/2004 | Hanafy et al. | |
| 2004/0220167 A1 | 11/2004 | Samly | |
| 2004/0234453 A1 | 11/2004 | Smith | |
| 2004/0254620 A1 | 12/2004 | Lacoste et al. | |
| 2004/0267252 A1 | 12/2004 | Washington et al. | |
| 2005/0038339 A1 | 2/2005 | Chauhan et al. | |
| 2005/0038340 A1 | 2/2005 | Vaezy et al. | |
| 2005/0043625 A1 | 2/2005 | Oliver et al. | |
| 2005/0046311 A1 | 3/2005 | Baumgartner et al. | |
| 2005/0054955 A1* | 3/2005 | Lidgren | 601/2 |
| 2005/0065436 A1 | 3/2005 | Ho et al. | |
| 2005/0070790 A1 | 3/2005 | Niwa et al. | |
| 2005/0085793 A1 | 4/2005 | Glossop | |
| 2005/0090104 A1 | 4/2005 | Yang et al. | |
| 2005/0096538 A1 | 5/2005 | Chomas et al. | |
| 2005/0096542 A1 | 5/2005 | Weng et al. | |
| 2005/0119704 A1 | 6/2005 | Peters et al. | |
| 2005/0149126 A1 | 7/2005 | Libbus | |
| 2005/0154299 A1 | 7/2005 | Hoctor et al. | |
| 2005/0165298 A1 | 7/2005 | Larson et al. | |
| 2005/0182297 A1 | 8/2005 | Gravenstein et al. | |
| 2005/0182319 A1 | 8/2005 | Glossop | |
| 2005/0192638 A1* | 9/2005 | Gelfand et al. | 607/3 |
| 2005/0240102 A1 | 10/2005 | Rachlin et al. | |
| 2005/0240103 A1 | 10/2005 | Byrd et al. | |
| 2005/0240126 A1 | 10/2005 | Foley et al. | |
| 2005/0240127 A1 | 10/2005 | Seip et al. | |
| 2005/0240170 A1 | 10/2005 | Zhang et al. | |
| 2005/0240241 A1 | 10/2005 | Yun et al. | |
| 2005/0261672 A1 | 11/2005 | Deem et al. | |
| 2005/0277853 A1 | 12/2005 | Mast et al. | |
| 2005/0288730 A1 | 12/2005 | Deem et al. | |
| 2006/0025756 A1 | 2/2006 | Francischelli et al. | |
| 2006/0052701 A1 | 3/2006 | Carter et al. | |
| 2006/0058678 A1 | 3/2006 | Vitek et al. | |
| 2006/0058707 A1 | 3/2006 | Barthe et al. | |
| 2006/0082771 A1 | 4/2006 | Doerrmann et al. | |
| 2006/0084966 A1 | 4/2006 | Maguire et al. | |
| 2006/0122514 A1 | 6/2006 | Byrd et al. | |
| 2006/0184069 A1 | 8/2006 | Vaitekunas | |
| 2006/0235300 A1 | 10/2006 | Weng et al. | |
| 2006/0235303 A1 | 10/2006 | Vaezy et al. | |
| 2006/0293712 A1 | 12/2006 | Kieval et al. | |
| 2007/0004984 A1 | 1/2007 | Crum et al. | |
| 2007/0016274 A1 | 1/2007 | Boveja et al. | |
| 2007/0038115 A1 | 2/2007 | Quigley et al. | |
| 2007/0055155 A1 | 3/2007 | Owen et al. | |
| 2007/0055181 A1 | 3/2007 | Deem et al. | |
| 2007/0066957 A1 | 3/2007 | Demarais et al. | |
| 2007/0106339 A1 | 5/2007 | Errico et al. | |
| 2007/0112327 A1 | 5/2007 | Yun et al. | |
| 2007/0129720 A1 | 6/2007 | Demarais et al. | |
| 2007/0129761 A1 | 6/2007 | Demarais et al. | |
| 2007/0135875 A1* | 6/2007 | Demarais et al. | 607/96 |
| 2007/0142879 A1 | 6/2007 | Greenberg et al. | |
| 2007/0149880 A1 | 6/2007 | Willis | |
| 2007/0167806 A1 | 7/2007 | Wood et al. | |
| 2007/0179379 A1 | 8/2007 | Weng et al. | |
| 2007/0203527 A1 | 8/2007 | Ben-David et al. | |
| 2007/0213616 A1 | 9/2007 | Anderson et al. | |
| 2007/0233185 A1 | 10/2007 | Anderson et al. | |
| 2007/0239000 A1 | 10/2007 | Emery et al. | |
| 2007/0265687 A1* | 11/2007 | Deem et al. | 607/72 |
| 2007/0282407 A1 | 12/2007 | Demarais et al. | |
| 2008/0033292 A1 | 2/2008 | Shafran | |
| 2008/0033420 A1 | 2/2008 | Nields et al. | |
| 2008/0039746 A1 | 2/2008 | Hissong et al. | |
| 2008/0045864 A1 | 2/2008 | Candy et al. | |
| 2008/0045865 A1 | 2/2008 | Kislev | |
| 2008/0047325 A1 | 2/2008 | Bartlett | |
| 2008/0051767 A1 | 2/2008 | Rossing et al. | |
| 2008/0058683 A1 | 3/2008 | Gifford et al. | |
| 2008/0194954 A1 | 8/2008 | Unger et al. | |
| 2008/0200806 A1 | 8/2008 | Liu et al. | |
| 2008/0200815 A1 | 8/2008 | Van Der Steen et al. | |
| 2008/0234569 A1 | 9/2008 | Tidhar et al. | |
| 2008/0255498 A1 | 10/2008 | Houle | |
| 2008/0255642 A1 | 10/2008 | Zarins et al. | |
| 2008/0312561 A1 | 12/2008 | Chauhan | |
| 2008/0312562 A1 | 12/2008 | Routh et al. | |
| 2008/0317204 A1 | 12/2008 | Sumanaweera et al. | |
| 2008/0319375 A1 | 12/2008 | Hardy | |
| 2009/0012098 A1 | 1/2009 | Jordan et al. | |
| 2009/0036948 A1 | 2/2009 | Levin et al. | |
| 2009/0054770 A1 | 2/2009 | Daigle | |
| 2009/0062697 A1 | 3/2009 | Zhang et al. | |
| 2009/0062873 A1 | 3/2009 | Wu et al. | |
| 2009/0076409 A1 | 3/2009 | Wu et al. | |
| 2009/0088623 A1 | 4/2009 | Vortman et al. | |
| 2009/0112095 A1 | 4/2009 | Daigle | |
| 2009/0112133 A1 | 4/2009 | Deisseroth et al. | |
| 2009/0163982 A1 | 6/2009 | Decharms | |
| 2009/0221908 A1 | 9/2009 | Glossop | |
| 2009/0221939 A1 | 9/2009 | Demarais et al. | |
| 2009/0247911 A1 | 10/2009 | Novak et al. | |
| 2009/0264755 A1 | 10/2009 | Chen et al. | |
| 2009/0306644 A1 | 12/2009 | Mayse et al. | |

(56) References Cited

U.S. PATENT DOCUMENTS

| | | | |
|---|---|---|---|
| 2010/0010393 | A1 | 1/2010 | Duffy et al. |
| 2010/0022921 | A1 | 1/2010 | Seip et al. |
| 2010/0023088 | A1 | 1/2010 | Stack et al. |
| 2010/0042020 | A1 | 2/2010 | Ben-Ezra |
| 2010/0081971 | A1 | 4/2010 | Allison |
| 2010/0092424 | A1 | 4/2010 | Sanghvi et al. |
| 2010/0125269 | A1 | 5/2010 | Emmons et al. |
| 2010/0160781 | A1 | 6/2010 | Carter et al. |
| 2010/0174188 | A1 | 7/2010 | Wang et al. |
| 2011/0021913 | A1 | 1/2011 | Weng et al. |
| 2011/0028867 | A1 | 2/2011 | Choo et al. |
| 2011/0112400 | A1 | 5/2011 | Emery et al. |
| 2011/0124976 | A1 | 5/2011 | Sabczynski et al. |
| 2011/0251489 | A1 | 10/2011 | Zhang et al. |
| 2011/0257561 | A1 | 10/2011 | Gertner et al. |
| 2012/0065492 | A1 | 3/2012 | Gertner et al. |
| 2012/0109018 | A1 | 5/2012 | Gertner et al. |

FOREIGN PATENT DOCUMENTS

| | | | |
|---|---|---|---|
| EP | 0679371 | A1 | 11/1995 |
| EP | 1265223 | A2 | 12/2002 |
| EP | 1579889 | | 9/2005 |
| EP | 1847294 | A1 | 10/2007 |
| JP | H05-220152 | | 8/1993 |
| JP | 2007000218 | | 1/2007 |
| WO | WO 9502361 | | 1/1995 |
| WO | WO 9731364 | A1 | 8/1997 |
| WO | WO 9948621 | A2 | 9/1999 |
| WO | WO 0134018 | A2 | 5/2001 |
| WO | WO 02069805 | A2 | 9/2002 |
| WO | WO 2005030295 | A2 | 4/2005 |
| WO | WO 2006003606 | | 1/2006 |
| WO | WO 2006121447 | A2 | 11/2006 |
| WO | WO 2006129099 | | 12/2006 |
| WO | WO 2008144274 | | 11/2008 |
| WO | WO 2009003138 | | 12/2008 |
| WO | WO 2009018351 | | 2/2009 |
| WO | WO 2009018394 | A1 | 2/2009 |
| WO | WO 2009081339 | | 7/2009 |
| WO | WO 2011053757 | A1 | 5/2011 |
| WO | WO 2011053772 | A1 | 5/2011 |

OTHER PUBLICATIONS

European Search Report & Search Opinion dated Nov. 25, 2011 for European Application No. 10810835.8.
Non-Final Office Action dated Nov. 28, 2011 for U.S. Appl. No. 13/246,763.
Non-Final Office Action dated Mar. 20, 2012 for U.S. Appl. No. 13/246,775.
Final Office Action dated Apr. 25, 2012 for U.S. Appl. No. 13/246,763.
International Preliminary Report on Patentability dated Apr. 17, 2012 for PCT Appln. No. PCT/US10/52193.
International Preliminary Report on Patentability dated Apr. 17, 2012 for PCT Appln. No. PCT/US10/52197.
Non-Final Office Action dated Apr. 10, 2012 for U.S. Appl. No. 12/725,450.
Non-Final Office Action dated Apr. 6, 2012 for U.S. Appl. No. 12/685,655.
Final Office Action dated Jun. 6, 2012 for U.S. Appl. No. 12/725,450.
Non-Final Office Action dated Jun. 8, 2012 for U.S. Appl. No. 13/019,273.
Non-Final Office Action dated Jun. 18, 2012 for U.S. Appl. No. 12/966,954.
Non-Final Office Action dated Jun. 18, 2012 for U.S. Appl. No. 12/966,962.
Final Office Action dated Jun. 26, 2012 for U.S. Appl. No. 12/685,655.
Non-Final Office Action dated Jun. 22, 2012 for U.S. Appl. No. 12/966,943.
Advisory Action dated Jun. 29, 2012 for U.S. Appl. No. 13/246,763.
Non-Final Office Action dated Jul. 3, 2012 for U.S. Appl. No. 12/902,133.
Advisory Action dated Jul. 9, 2012 for U.S. Appl. No. 12/685,655.
Non-Final Office Action dated Jul. 27, 2012 for U.S. Appl. No. 13/487,135.
Non-Final Office Action dated Jul. 30, 2012 for U.S. Appl. No. 13/445,903.
Advisory Action dated Aug. 15, 2012 for U.S. Appl. No. 12/725,450.
Notice of Allowance dated Aug. 27, 2012 for U.S. Appl. No. 12/685,655.
Final Office Action dated Aug. 29, 2012 for U.S. Appl. No. 12/966,954.
Non-Final Office Action dated Aug. 29, 2012 for U.S. Appl. No. 13/487,118.
Non-Final Office Action dated Aug. 29, 2012 for U.S. Appl. No. 13/487,121.
Non-Final Office Action dated Sep. 7, 2012 for U.S. Appl. No. 13/048,837.
Non-Final Office Action dated Sep. 10, 2012 for U.S. Appl. No. 13/523,835.
Non-Final Office Action dated Sep. 21, 2012 for U.S. Appl. No. 13/535,070.
Non-Final Office Action dated Sep. 24, 2012 for U.S. Appl. No. 13/048,830.
Non-Final Office Action dated Sep. 24, 2012 for U.S. Appl. No. 13/246,763.
Non-Final Office Action dated Sep. 25, 2012 for U.S. Appl. No. 13/111,837.
Non-Final Office Action dated Oct. 4, 2012 for U.S. Appl. No. 13/091,116.
Non-Final Office Action dated Oct. 10, 2012 for U.S. Appl. No. 13/048,844.
Non-Final Office Action dated Oct. 15, 2012 for U.S. Appl. No. 13/048,842.
Final Office Action dated Oct. 16, 2012 for U.S. Appl. No. 13/246,775.
Extended European Search Report dated Oct. 22, 2012 for European Appln. No. 10823909.6.
European Examination Report dated Oct. 22, 2012 for EP Appln. No. 10810835.8.
Final Office Action dated Oct. 23, 2012 for U.S. Appl. No. 13/019,273.
Notice of Allowance dated Nov. 9, 2012 for U.S. Appl. No. 13/019,273.
Final Office Action dated Dec. 4, 2012 for U.S. Appl. No. 13/487,135.
Final Office Action dated Dec. 5, 2012 for U.S Appl. No. 12/966,943.
European Search Report & Search Opinion dated Dec. 7, 2012 for European Application No. 11758075.3.
Final Office Action dated Dec. 10, 2012 for U.S. Appl. No. 12/966,962.
Advisory Action dated Dec. 28, 2012 for U.S. Appl. No. 13/246,775.
Non-Final Office Action dated Jan. 2, 2013 for U.S. Appl. No. 13/545,944.
Final Office Action dated Jan. 15, 2013 for U.S. Appl. No. 13/487,121.
Final Office Action dated Jan. 17, 2013 for U.S. Appl. No. 13/487,118.
Final Office Action dated Jan. 29, 2013 for U.S. Appl. No. 13/048,837.
Final Office Action dated Jan. 31, 2013 for U.S. Appl. No. 13/535,070.
Final Office Action dated Feb. 1, 2013 for U.S. Appl. No. 13/523,835.
Foreign Office Action dated Feb. 14, 2013 for Australian Appln. No. 2010307029.
Final Office Action dated Feb. 15, 2013 for U.S. Appl. No. 13/445,903.
Final Office Action dated Feb. 15, 2013 for U.S. Appl. No. 13/048,830.
Advisory Action dated Feb. 25, 2013 for U.S. Appl. No. 13/487,135.
Final Office Action dated Feb. 25, 2013 for U.S. Appl. No. 13/048,842.

(56) References Cited

OTHER PUBLICATIONS

Final Office Action dated Mar. 14, 2013 for U.S. Appl. No. 13/091,116.
Final Office Action dated Mar. 15, 2013 for U.S. Appl. No. 13/111,837.
Advisory Action dated Apr. 11, 2013 for U.S. Appl. No. 13/048,837.
Non-Final Office Action dated Apr. 15, 2013 for U.S. Appl. No. 13/246,775.
Final Office Action dated Apr. 19, 2013 for U.S. 2013 for U.S. Appl. No. 13/545,944.
Notice of Allowance dated Apr. 29, 2013 for U.S. Appl. No. 13/048,830.
Final Office Action dated Apr. 29, 2013 for U.S. Appl. No. 13/048,844.
Notice of Allowanced dated Apr. 30, 2013 for U.S. Appl. No. 13/048,842.
Notice of Allowance dated May 15, 2013 for U.S. Appl. No. 13/535,070.
Advisory Action dated Jun. 18, 2013 for U.S. Appl. No. 12/902,133.
Advisory Action dated Jun. 18, 2013 for U.S. Appl. No. 13/523,835.
Examination Report dated Jun. 24, 2013 for EP Appln. No. 10823909.6.
Notice of Allowance dated Jun. 24, 2013 for U.S. Appl. No. 12/966,962.
European Examination Report dated Jun. 24, 2013 for EP Appln. No. 10810835.8.
M. William Apoutou N'dijin: "Transducteur torique a Ultrasons Focalises de Haute Intensite pour generer des ablations volumineuses", Dec. 17, 2008, XP055009820, URL: http://u556.lyon.inserm.fr/theses/pdf/ndjin.pdf.
Final Office Action dated Jul. 1, 2013 for U.S. Appl. No. 13/246,763.
Advisory Action dated Jul. 25, 2013 for U.S. Appl. No. 13/545,944.
Advisory Action dated Aug. 15, 2013 for U.S. Appl. No. 13/048,844.
Non-Final Office Action dated Aug. 20, 2013 for U.S. Appl. No. 13/545,944.
Office Action dated Aug. 20, 2013 for Russian Appln. No. 2012119540.
Advisory Action dated Sep. 3, 2013 for U.S. Appl. No. 13/111,837.
Notice of Allowance dated Sep. 13, 2013 for U.S. Appl. No. 13/111,837.
Notice of Allowance dated Oct. 8, 2013 for U.S. Appl. No. 13/523,835.
Non-Final Office Action dated Oct. 10, 2013 for U.S. Appl. No. 13/657,725.
International Search Report and Written Opinion dated Nov. 26, 2013 for PCT Appln. No. PCT/US2013/057624.
Final Office Action dated Dec. 27, 2013 for U.S. Appl. No. 13/545,944.
Final Office Action dated Jan. 13, 2014 for U.S. Appl. No. 13/246,775.
Foreign Office Action for CN Patent Application No. 201110378545.2 dated Jan. 13, 2014.
Notice of Allowance dated Jan. 14, 2014 for U.S. Appl. No. 13/445,903.
Foreign Office Action dated Mar. 14, 2014 for Australian Appln. No. 2010307029.
Non-Final Office Action dated Apr. 1, 2014 for U.S. Appl. No. 12/902,135.
Foreign Office Action dated Apr. 8, 2014 for Japanese Patent Appln. No. 2012-533385.
Advisory Action dated Apr. 21, 2014 for U.S. Appl. No. 13/246,775.
Non-Final Office Action dated Jun. 9, 2014 for U.S. Appl. No. 12/725,450.
Non-Final Office Action dated Jun. 26, 2014 for U.S. Appl. No. 12/966,954.
Final Office Action dated Jan. 12, 2015 for U.S. Appl. No. 12/725,450.
"The Journal of Allergy and Clinical Immunology" vol. 63, No. 3, 1979.

Accord et al., "The Issue of Transmurality in Surgical Ablation for Atrial Fibrillation." *Cardiothoracic Surgery Network*: 3pp, Aug. 8, 2005.
Amenta et al., "A New Voronoi-Based Surface Reconstruction Algorithm." *Computer Graphics*: 7pp, 1998.
American Red Cross., "Blood 101." 4pp., Dec. 11, 2007.
Anand et al., "Monitoring formation of high intensity focused ultrasound (HIFU) induced lesions using backscattered ultrasound." *Acoustical Society of America*; Mar. 10, 2004.
Anand et al., "Using the ATL 1000 to Collect Demodulated RF Data for Monitoring HIFU Lesion Formation." Presented at *SPIE Medical Imaging 2003*. 11pp, 2003.
Aurenhammer, F. "Voronoi diagrams—A Survey of a Fundamental Geometric Data Structure." *ACM Computing Surveys*, vol. 23, No. 3: 345-405, Sep. 1991.
Bachmann, et al. "Targeting Mucosal Addressin Cellular Adhesion Molecule (MAdCAM)-1 to Noninvasively Image Experimental Crohn's Disease." Gastroenterology 2006; 130: 8-16.
Barthe et al. "Efficient Wideband Linear Arrays for Imaging and Therapy" IEEE Ultrasonics Symposium. pp. 1249-1252 (1999).
Bauer et al., "Ultrasound Imaging with SonoVue: Low Mechanical Index Real-Time Imaging." *Acad. Radiol.*; vol. 9, Suppl. 2: S282-S284, 2002.
Beard et al., "An Annular Focus Ultrasonic Lens for Local Hyperthermia Treatment of Small Tumors." *Ultrasound in Medicine & Biology*; vol. 8, No. 2: 177-184, 1982.
Bokarewa et al., "Tissue factor as a proinflammatory agent." *Arthritis Research*, vol. 4: 190-195, Jan. 10, 2002.
Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.
Brayman et al., "Erosion of Artificial Endothelia In Vitro by Pulsed Ultrasound: Acoustic Pressure, Frequency, Membrane Orientation and Microbubble Contrast Agent Dependence." *Ultrasound in Medicine & Biology*; vol. 25, No. 8: 1305-1320, 1999.
Buller et al., "Accurate Three-dimensional Wall Thickness Measurement From Multi-Slice Short-Axis MR Imaging." *Computers in Cardiology*, 245-248, 1995.
Byram et al., "3-D Phantom and In Vivo Cardiac Speckle Tracking Using a Matrix Array and Raw Echo Data." IEEE Transactions on Ultrasonics, Ferroelectrics, and Frequency Control, vol. 57, No. 4; 839-854, Apr. 2010.
Campese, V., Krol, E. Neurogenic Factors in Renal Hypertension. Current Hypertension Reports 2002, 4:256-260.
Canadian Examination Report dated Nov. 14, 2007 in CA Patent Application 2,387,127, filed Oct. 25, 2000.
Chao et al., "Aspheric lens design." *Ultrasonics Symposium, 2000 IEEE*, vol. 2: Abstract Only, Oct. 2000.
Chelule, K. et al., Fabrication of medical models from scan data via rapid prototyping techniques, Proceedings of the 2000 Conference on Time Compression Technologies, Cardiff International Arena, UK; 2000.
Chen et al., "A comparison of the fragmentation thresholds and inertial cavitation doses of different ultrasound contrast agents." *Journal of the Acoustical Society of America*, vol. 113, No. 1: 643-665, Jan. 2003.
Chen et al., "Inertial Cavitation Dose and Hemolysis Produced In Vitro With or Without Optison." *Ultrasound in Medicine & Biology*, vol. 29, No. 5: 725-737, 2003.
Chen, Jie, and T. R. Gururaja. "DC-biased electrostrictive materials and transducers for medical imaging." Ultrasonics Symposium, 1997. Proceedings., 1997 IEEE. vol. 2. IEEE, 1997.
Chong et al., "Tissue Factor and Thrombin Mediate Myocardial Ischemia-Reperfusion Injury." *The Society of Thoracic Surgeons*, vol. 75: S649-655, 2003.
Damianou, C., K. Hynynen, and X. Fan. "Application of the thermal dose concept for predicting the necrosed tissue volume during ultrasound surgery."Ultrasonics Symposium, 1993. Proceedings., IEEE 1993. IEEE, 1993.
Dayton et al., "The magnitude of radiation force on ultrasound contrast agents." *Journal of the Acoustical Society of America*, vol. 112, No. 5, Part 1: 2183-2192, Nov. 2002.

(56) References Cited

OTHER PUBLICATIONS

Dempsey et al., "Thickness of Carotid Artery Atherosclerotic Plaque and Ischemic Risk." *Neurosurgery*, vol. 27, No. 3: 343-348, 1990.
Dewhisrt et al., "Basic principles of thermal dosimetry and thermal threshold for tissue damage from hyperthermia" 2003.
Dibona, G. F., "Neural control of the kidney: functionally specific renal sympathetic nerve fibers." Am J Physiol Regulatory Integrative Comp Physiol. pp. 1517-1524, 2000.
Dibona, G. F., et al., Chaotic behavior of renal sympathetic nerve activity: effect of baroreceptor denervation and cardiac failure, Am J Physiol Renal Physiol, 279:F491-501, 2000.
Dibona, GF. Functionally Specific Renal Sympathetic Nerve Fibers: Role in Cardiovascular Regulation. American Journal of Hypertension. 2001 vol. 14(6) 163S-170S.
Doumas, M., et al., Renal Sympathetic Denervation: The Jury is Still Out, The Lancet, Nov. 2010, vol. 376, Issue 9756, pp. 1878-1880.
Ebbini et al., "Image-guided noninvasive surgery with ultrasound phased arrays." *SPIE*, vol. 3249: 230-239, Apr. 2, 1998.
Edelsbrunner, Herbert. "Geometry and Topology for Mesh Generation." *Cambridge University Press*: 68pp, 2001.
Esler, et al.. "Renal sympathetic denervation in patients with treatment-resistant hypertension (The Symplicity HTN-2 Trials): a randomised controlled trial." The Lancet: vol. 376, Issue 9756, pp. 1903-1909. Dec. 4, 2010.
European Examination Report dated Mar. 7, 2008 in EP Patent Application 989717.4, filed Oct. 25, 2000.
Everbach et al., "Cavitational Mechanisms in Ultrasound-Accelerated Thrombolysis at 1 MHz." *Ultrasound in Medicine & Biology*, vol. 26, No. 7: 1153-1160, 2000.
Ewert, et al. "Anti-myeloperoxidase antibodies stimulate neutrophils to damage human endothelial cells." Kidney International, vol. 4, pp. 375-383. 1992.
Fjield, T., et al., A parametric study of the concentric-ring transducer design for MRI guided ultrasound surgery, J. Acoust. Soc. Am. vol. 100, Issue 2, pp. 1220-1230 (1996); (11 pages).
Fowlkes, J. Brian, and Christy K. Holland. "Mechanical bioeffects from diagnostic ultrasound: AIUM consensus statements. American Institute of Ultrasound in Medicine." Journal of ultrasound in medicine: official journal of the American Institute of Ultrasound in Medicine 19.2 (2000): 69-72.
Ganapathy et al., "A New General Triangulation Method for Planar Contours." *Computer Graphics* vol. 16, No. 3:69-75, 1982.
Grassi, G. "Role of the sympathetic nervous system in human hypertension." Journals of Hypertension 1998, vol. 16. No. 12.
Gray, Henry. "The Skull." *Anatomy of the Human Body*: 7pp., 1918.
Guzman et al., "Ultrasound—Mediated Disruption of Cell Membranes. I. Quantification of Molecular uptake and Cell Viability. / II. Heterogeneous effects on cells." *Journal of the Acoustical Society of America*, vol. 110, No. 1: 588-606, Jul. 2001.
Hachimine, et al. "Sonoynamic therapy of cancer using a novel porphyrin deriative, DCPH-P-Na(I), which is devoid of photosensitivity." Japanese Cancer Association pp. 916-920. Apr. 4, 2007.
Hadimioglu et al., "High-Efficiency Fresnel Acoustic Lenses." *Ultrasonics Symposium* 1993 IEEE: 579-582, 1993.
Han et al., "A Fast Minimal Path Active Contour Model." IEEE Transactions on Image Processing, vol. 10, No. 6: 865-873, Jun. 2001.
Hatangadi, Ram. "A Novel Dual Axis Multiplanar Transesophageal Ultrasound Probe for Three-Dimensional Echocardiograph."_*University of Washington, Department of Sciences and Engineering*, vol. 55-11B: Abstract 1pg, 1994.
Henry Gray, "The Skull" 1918.
Holt et al., "Bubbles and Hifu: the Good, the Bad and the Ugly." *Boston University, Department of Aerospace and Mechanical Engineering*: 120-131, 2002.
Hubka et al., "Three-dimensional echocardiographic measurement of left ventricular wall thickness: In vitro and in vivo validation." *Journal of the American Society of Echocardiography*, vol. 15, No. 2: 129-135, 2002.
Hutchinson et al. "Intracavitary Ultrasound Phased Arrays for Noninvasive Prostate Surgery." IEEE Transactions on Ultrasonics. Ferroelectrics, and Frequency Control. 43(6):1032-1042 (1996).
Hwang et al., "Vascular Effects Induced by Combined 1-MHz Ultrasound and Microbubble Contrast Agent Treatments In Vivo." *Ultrasound in Medicine & Biology*, vol. 31, No. 4: 553-564, 2005.
Hynynen et al., "Potential Adverse Effects of High-Intensity Focused Ultrasound Exposure on Blood Vessels In Vivo." *Ultrasound in Medicine & Biology*, vol. 22, No. 2: 193-201, 1996.
Iannuzzi, et al. "Ultrasonographic Correlates of Carotid Atherosclerosis in Transient Ischemic Attack and Stroke." The American Heart Association. 1995; 26: 614-619.
Idell et al., "Fibrin Turnover in Lung Inflammation and Neoplasia." *American Journal of Respiratory and Critical Care Medicine*, vol. 163: 578-584, 2001.
Indman, P. "Advanced Gynecology Solutions." Dec. 10, 2010. <http://www.gynalternatives.com/hsc.htm>.
International Search Report and Written Opinion dated Dec. 6, 2010 for PCT Application No. PCT/US2010/052193.
International Search Report and Written Opinion dated Jun. 6, 2011 for PCT/US2010/052197.
International Search Report and Written Opinion dated May 18, 2001 in PCT/US2000/041606.
Janssen, B. J., and J. F. Smits. "Renal nerves in hypertension." Mineral and electrolyte metabolism 15.1-2 (1988): 74-82.
Janssen, et al. "Renal Nerves in Hypertension." S.Karger AG, Basell, 1989.
Jolesz, F. MRI-Guided Focused Ultrasound Surgery. Annual Review of Medicine. 2009 60:417-30.
Kaczkowski et al., "Development of a High Intensity Focused Ultrasound System for Image-Guided Ultrasonic Surgery." *Ultrasound for Surgery*, 2001. <http://cimu.apl.washington.edu/hifusurgerysystem.html>.
Kang et al., "Analysis of the Measurement Precision of Arterial Lumen and Wall Areas Using High-Resolution MRI." *Magnetic Resonance in Medicine*, vol. 44: 968-972, 2000.
Kirk Shung, K., et al. "Ultrasonic characterization of blood during coagulation." Journal of clinical ultrasound 12.3 (1984): 147-153.
Klibanov et al., "Detection of Individual Microbubbles of an Ultrasound contrast Agent: Fundamental and Pulse Inversion Imaging." *Academy of Radiology*, vol. 9, Suppl. 2: S279-S281, 2002.
Kojima, T., Matrix Array Transducer and Flexible Matrix Arry Transducer,Proceedings of the Ultrasonics Symposium, vol. 2:649-653 (1986).
Krum, et al. "Pharmacologic Mangement of the Cardiorenal Syndrome in Heart Failure." Current heart Failure Reports pp. 105-111, 2009.
Krum, H et. al., "Catheter-Based Renal Sympathetic Denervation for Resistant Hypertension: a Multicentre Safety and Proof-of-Principle Cohort Study," Lancet 2009 373; 1275-1281.
Kudo et al., "Study on Mechanism of Cell Damage Caused by Microbubbles Exposed to Ultrasound." *Ultrasound in Medicine & Biology*, vol. 29, Supplement: 4pp, 2003.
Lalonde et al., "Field conjugate acoustic lenses for ultrasound hyperthermia." *Ultrasonics, Ferroelectrics and Frequency Control, IEEE Transactions*, vol. 40, Issue 5: Abstract 1pg., Sep. 1993.
Martin et al., Hemostasis of Punctured Vessels Using Doppler-Guided High Intensity Ultrasound,• Ultrasound in Med.& Biol., vol. 25, pp. 985-990, 1999, USA.
MDE et al., Renal sympathetic denervation in patients with treatment resistant hypertension (The Symplicity HTN-2 Trial): a randomised controlled trial, Nov. 2010, The Lancet, vol. 376, Issue 9756, pp. 1903-1909.
Meyers, D. "Multiresolution tiling." *Computer Graphics*, No. 5: 325-340, 1994.
Miller et al., "A Review of In Vitro Bioeffects of Inertial Ultrasonic Cavitation From a Mechanistic Perspective." *Ultrasound in Medicine & Biology*, vol. 22, No. 9: 1131-1154, 1996.
Miller, et al. "Diagnostic ultrasound activation of contrast agent gas bodies induces capillary rupture in mice." National Academy of Sciences, vol. 97, No. 18: 10179-10184, 2000.

(56) References Cited

OTHER PUBLICATIONS

Moss, N. G. Renal Function and Renal Afferent and Efferent Nerve Activity. American Journal Physiology. 243 (Renal Fluid Electrolyte Physiology) 12: F425-F433, 1982.
N. F. Sheahan et al., "Observing the brachial artery through a pressure cuff", 1993.
n.a., "Breast Cancer—Insightec: focused ultrasound for non invasive treatment." FAQ, 2000. <http://www.exablate2000.com/physicians_faq.html>.
n.a., "Cavitation." Ultrasound TIP—U.S. Database: Dec. 12, 2007.
n.a., "Mechanical Bioeffects in the Presence of Gas-Carrier Ultrasound Contrast Agents." *Journal of Ultrasound & Medicine*, vol. 19: 120-142, 2000.
Ng et al., "Therapeutic Ultrasound: Its Application in Drug Delivery." *Medicinal Research Reviews*, vol. 22, No. 2: 204-233, 2002.
Notice of Allowance dated Mar. 25, 2003 from U.S. Appl. No. 09/696,076, filed Oct. 25, 2000.
Office Action dated Aug. 17, 2006 from U.S. Appl. No. 10/671,417, filed Sep. 24, 2003.
Office Action dated Jul. 31, 2007 from U.S. Appl. No. 10/671,417, filed Sep. 24, 2003.
Office Action dated Jul. 5, 2006 from U.S. Appl. No. 10/616,831, filed Jul. 10, 2003.
Office Action dated Nov. 29, 2002 from U.S. Appl. No. 09/696,076, filed Oct. 25, 2000.
O'Leary, et al. "Carotid-Artery Intima and Media Thickness as a Risk Factor for Myocardial Infarction and Stroke in Older Adults." Cardiovascular Health Study Collaborative Research Group. New England Journal of Medicine, vol. 340, No. 1: 14-22, Jan. 7, 1999.
Ostensen et al., "Characterization and Use of Ultrasound Contrast Agents." *Academy of Radiology*, vol. 9, Suppl. 2: S276-S278, 2002.
Owaki et al., "The Ultrasonic Coagulating and Cutting System Injuries Nerve Function." *Endoscopy*, vol. 34, No. 7: 575-579, 2002.
Paul D. Indman, "What is Hysteroscopy" http://www.gynalternatives.com/hsc.htm, accessed on 2010.
Pernot, Mathieu, et al. "Temperature estimation using ultrasonic spatial compound imaging." Ultrasonics, Ferroelectrics and Frequency Control, IEEE Transactions on 51.5 (2004): 606-615.
Pignoli, P., et al., Intimal plus medial thickness of the arterial wall: a direct measurement with ultrasound imaging, Circulation 1986;74;1399-1406.
Poliachik et al., "Activation, Aggregation and Adhesion of Platelets Exposed to High-Intensity Focused Ultrasound." *Ultrasound in Medicine & Biology*, vol. 27, No. 11: 1567-1576, 2001.
Poliachik et al., "Effect of High-Intensity Focused Ultrasound on Whole Blood With or Without Microbubble Contrast Agent." *Ultrasound in Medicine & Biology*, vol. 25, No. 6: 991-998, 1999.
Porter et al., "Ultrasound, Microbubbles and Thrombolysis." *Progress in Cardiovascular Diseases*, vol. 44, No. 2: 101-110, Oct. 2001.
Recchia et al., "Ultrasonic tissue characterization of blood during stasis and thrombosis with a real-time linear-array backscatter imaging system", Coronary Artery Disease, 1993.
Rivens et al., "Vascular Occlusion Using Focused Ultrasound Surgery for Use in Fetal Medicine." *European Journal of Ultrasound*, vol. 9: 89-97, 1999.
Rose, J.L., "Ultrasonic Waves in Solid Media", 1999.
Rosen et al., "Vascular Occlusive Diseases." 37pp., revised 2002.
Rosenschein et al., "Shock-Wave Thrombus Ablation, A New Method for Noninvasive Mechanical Thrombolysis." *The American Journal of Cardiology*, vol. 70, Issue 15: Abstract, Nov. 15, 1992.
Rosenschein, U., et al., Ultrasound Imaging—Guided Noninvasive Ultrasound Thrombolysis : Preclinical Results, Circulation, 2000;102;238-245.
Sanghvi et al. "High-Intensity Focused Ultrasounds." Experimental and Investigational Endoscopy. 4(2):383-395 (1994).
Schlaich, et al. "Sympathetic Activation in Chronic Renal Failure." J Am Soc Nephrol. pp. 933-939, 2009.
Schulte-Altedorneburg, et al. "Accuracy of In Vivo Carotid B-Mode Ultrasound Compared with Pathological Analysis: Intima-Media Thickening, Lumen Diameter, and Cross-Sectional Area." American Stroke Association, vol. 32, No. 7: 1520-1524, 2001.
Sherrit, S., G. Catoiu, and B. K. Mukherjee. "The characterisation and modelling of electrostrictive ceramics for transducers." Ferroelectrics 228.1 (1999): 167-196.
Shrout, T. R., et al. "Classification of Electrostrictive Based Materials for Transducers." Proceedings of the 6th US—Japan Seminar on Dielectric and Piezoelectric Ceramics. 1993.
Simon, Claudio, Philip VanBaren, and Emad S. Ebbini. "Two-dimensional temperature estimation using diagnostic ultrasound." Ultrasonics, Ferroelectrics and Frequency Control, IEEE Transactions on 45.4 (1998): 1088-1099.
Tachibana et al. "Albumin Microbubble Echo-Contrast Material as Enhancer for Ultrasound Accelerated Thrombolysis." American Heart Association. vol. 92: 1148-1150, 1995.
Tachibana et al., "The Use of Ultrasound for Drug Delivery." *Echocardiography*, vol. 18, No. 4: 323-328, May 2001.
Tardy et al., "In Vivo Ultrasound Imaging of Thrombi Using a Target-specific Contrast Agent." *Academy of Radiology*, vol. 9, Suppl. 2: S294-S296, 2002.
ter Haar. G. Ultrasound Focal Beam Surgery. Ultrasound in Medicine and Biology. 21(9):1089-1100 (1995).
Vaezy et al., "Acoustic surgery." *Physics World*: 35-39, Aug. 2001.
Vaezy et al., "Hemostasis and Tumor Treatment using High Intensity Focused Ultrasound: Experimental Investigations and Device Development." *First International Workshop on the Application of HIFU in Medicine*: 46-49, 2001.
Vaezy et al., "Hemostasis using high intensity focused ultrasound." *European Journal of Ultrasound*, vol. 9: 79-87, 1999.
Vaezy et al., "Intra-operative acoustic hemostasis of liver: production of a homogenate for effective treatment." *Ultrasonics*, vol. 43: 265-269, 2005.
Vaezy, S. et al., Hemostasis of Punctured Blood Vessels Using High-Intensity Focused Ultrasound, Ultrasound in Medicine and Biology, 1998, vol. 24; No. 6, pp. 903-910.
Valente, et al. "Laparoscopic renal denervation for intractable ADPKD-related pain." Nephrol Dial Transplant. pp. 160. 2001.
Von Land et al., "Development of an Improved Centreline Wall Motion Model." *IEEE*: 687-690, 1991.
Watkin et al., "Multi-Modal Contrast Agents: A First Step." *Academy of Radiology*, vol. 9, Suppl. 2: S285-S287, 2002.
Wickline et al., "Blood Contrast Enhancement with a Novel, Non-Gaseous Nanoparticle Contrast Agent." *Academy of Radiology*, vol. 9, Suppl. 2: S290-S293, 2002.
Williamson et al., "Color Doppler Ultrasound Imaging of the Eye and Orbit." *Survey of Ophthalmology*, vol. 40, No. 4: 255-267, 1996.
Yu et al., "A microbubble agent improves the therapeutic efficiency of high intensity focused ultrasound: a rabbit kidney study." *Urological Research*, PubMed: Abstract, 2004.
Foreign Office Action dated Feb. 26, 2014 for Korean Application No. 10-2012-701259.
Notice of Allowance dated Mar. 6, 2014 for U.S. Appl. No. 13/523,835.
Foreign Office Action dated May 6, 2014 for Canadian Patent Appln. No. 2777228.
Examination Report dated Jun. 16, 2014 for European Application No. 11758075.3.
Foreign Office Action dated Jun. 17, 2014 for European Appln. No. 10823909.6.
European Examination Report dated Jun. 18, 2014 for EP Appln. No. 10810835.8.
International Search Report and Written Opinion for PCT/US14/22141 dated Jul. 9, 2014.
Foreign Office Action dated Jul. 21, 2014 for Israeli Application No. 219083.
Non-Final Office Action dated Aug. 1, 2014 for U.S. Appl. No. 12/902,133.
Notice of Allowance dated Aug. 19, 2014 for U.S. Appl. No. 13/048,837.
Non-Final Office Action dated Sep. 11, 2014 for U.S. Appl. No. 12/966,943.
Non-Final Office Action dated Sep. 11, 2014 for U.S. Appl. No. 13/487,121.

(56) References Cited

OTHER PUBLICATIONS

Non-Final Office Action dated Sep. 12, 2014 for U.S. Appl. No. 13/487,135.
Non-Final Office Action dated Sep. 17, 2014 for U.S. Appl. No. 13/246,775.
Non-Final Office Action dated Oct. 3, 2014 for U.S. Appl. No. 14/207,511.
Non-Final Office Action dated Oct. 3, 2014 for U.S. Appl. No. 14/207,516.
Rabkin et al. "Biology and Physical Mechanisms of HIFU-Induced Hyperecho in Ultrasound Images" 2006 Ultrasound in Med. & Biol. 32:1721-1729.
Singh et al. "Ultrasonic Hyperthermia for Cancer Treatment" 1993 Defence Science J. 43:235-241.
Vaezy et al. "Hemorrhage control using high intensity focused ultrasound" 2007 Int.J.Hyperthermia 23:203-211.
Non-Final Office Action dated Oct. 8, 2014 for U.S. Appl. No. 13/487,118.
Notice of Allowance dated Oct. 27, 2014 for U.S. Appl. No. 13/523,835.
Non-Final Office Action dated Nov. 6, 2014.
Notice of Allowance dated Nov. 7, 2014 for U.S. Appl. No. 13/048,837.
Notice of Allowance dated Nov. 7, 2014 for U.S. Appl. No. 13/523,835.
Foreign Office Action dated Nov. 20, 2014 for Korean Application No. 10-2012-701259.
Non-Final Office Action dated Nov. 24, 2014 for U.S. Appl. No. 13/091,116.
Notice of Allowance dated Nov. 26, 2014 for U.S. Appl. No. 13/048,844.
Foreign Office Action dated Nov. 27, 2014 for Indonesian Appln. No. W00201201713.
Notice of Allowance dated Nov. 28, 2014 for U.S. Appl. No. 13/111,837.
Foreign Office Action dated Dec. 16, 2014 for Japanese Patent Appln. No. 2012-533385.
Non-Final Office Action dated Dec. 23, 2014 for U.S. Appl. No. 13/545,944.
Final Office Action dated Jan. 13, 2015 for U.S. Appl. No. 12/966,943.
Final Office Action dated Jan. 14, 2015 for U.S. Appl. No. 13/487,121.
Final Office Action dated Jan. 15, 2015 for U.S. Appl. No. 12/966,954.
Notice of Allowance dated Jan. 20, 2015 for U.S. Appl. No. 12/902,133.
Advisory Action dated Jan. 22, 2015 for U.S. Appl. No. 13/487,121.
Final Office Action dated Jan. 26, 2015 for U.S. Appl. No. 12/902,135.
Non-Final Office Action dated Jan. 28, 2015 for U.S. Appl. No. 13/246,763.
Final Office Action dated Feb. 24, 2015 for U.S. Appl. No. 13/487,135.
Non-Final Office Action dated Mar. 12, 2015 for U.S. Appl. No. 13/228,366.
Non-Final Office Action dated Mar. 23, 2015 for U.S. Appl. No. 14/015,331.
Foreign Office Action dated Apr. 17, 2015 for Canadian Appln. No. 2,777,228.
Non-Final Office Action dated Apr. 20, 2015 for U.S. Appl. No. 13/960,743.
Eckberg Physiological basis for human autonomic rhythms. 2000 Ann.Med. 32:341-349.
Liedtke et al. Total systemic autoregulation in the dog and its inhibition by baroreceptor reflexes. 1973 Cir. Res. 32:673-677.
Lohmeier et al. Prolonged activation of the baroreflex abolishes obesity-induced hypertension. 2007 Hypertension 49:1307-1314.
Lohmeier et al. Prolonged Activation of the Baroreflex Produces Sustained Hypotension. 2004 Hypertension 43:306-311.
Non-Final Office Action dated Apr. 22, 2015 for U.S. Appl. No. 13/717,401.
Non-Final Office Action dated Apr. 24, 2015 for U.S. Appl. No. 14/207,526.
Non-Final Office Action dated Apr. 28, 2015 for U.S. Appl. No. 14/207,642.
Final Office Action dated May 22, 2014 for U.S. Appl. No. 13/487,118.
Final Office Action dated Jun. 5, 2015 for U.S. Appl. No. 14/207,511.
Final Office Action dated Jun. 5, 2015 for U.S. Appl. No. 14/207,516.
Non-Final Office Action dated Jun. 5, 2015 for U.S. Appln. No.
Ebbini et al. A spherical-section ultrasound phased array applicator for deep localized hyperthermia. 1991 IEEE Trans. Biom. Eng. 38:634-643.
Karmakar. Thoracic paravertebral block. 2001 Anesth. 95:771-780.
Kostreva et al. Reflex effects of hepatic baroreceptors on renal and cardiac sympathetic nerve activity. 1980 Am. J. Physiol. 238:R390-R394.
Liu et al. a fast and conformal heating scheme for producing large thermal lesions using a 20 ultrasound phased array. 2007 Int. J. Hyperthermia 23:69-82.
Pernot et al. 3-D Real-time motion correction in high-intensity focused ultrasound therapy. 2004 Ultrasound Med. Biol. 30:1239-1249.
Ralls. Color doppler sonography of the hepatic artery and portal venous system. 1990 Am. J. Roentgenology 155:517-525.
Shanta. Unilateral bronchospasm after interpleural analgesia. 1992 Anesth. Analg. 74:291-293.
Final Office Action dated Jun. 8, 2015 for U.S. Appl. No. 13/657,725.
Notice of Allowance dated Jun. 5, 2015 for U.S. Appl. No. 13/091,116.

* cited by examiner

EXTERNAL AUTONOMIC MODULATION

RELATED APPLICATION DATA

This application is a continuation of U.S. patent application Ser. No. 12/725,450, filed on Mar. 16, 2010, pending, which claims priority to and the benefit of U.S. Provisional Patent Application No. 61/303,307 filed Feb. 10, 2010, U.S. Provisional Patent Application No. 61/256,983 filed Oct. 31, 2009, U.S. Provisional Patent Application No. 61/250,857 filed Oct. 12, 2009, U.S. Provisional Patent Application No. 61/261,741 filed Nov. 16, 2009, and U.S. Provisional Patent Application No. 61/291,359 filed Dec. 30, 2009, and is a continuation-in-part of U.S. patent application Ser. No. 12/685,655, filed Jan. 11, 2010, now U.S. Pat. No. 8,295,912, which claims priority to and the benefit of U.S. Provisional Patent Application No. 61/256,983 filed Oct. 31, 2009, U.S. Provisional Patent Application No. 61/250,857 filed Oct. 12, 2009, U.S. Provisional Patent Application No. 61/261,741 filed Nov. 16, 2009, and U.S. Provisional Patent Application No. 61/291,359 filed Dec. 30, 2009, the entire disclosures of all of which are expressly incorporated by reference herein. This application is also related to U.S. patent application Ser. No. 13/111,837, filed on May 19, 2011, pending.

BACKGROUND

Energy delivery from a distance involves transmission of energy waves to affect a target some distance away. It allows for more efficient delivery of energy to targets and greater cost efficiency and technologic flexibility on the generating side. For example, cellular phones receive targets from towers close to the user and the towers communicate with one another over a long range; this way, the cell phones can be low powered and communicate over a relatively small range yet the network can quickly communicate across the world. Similarly, electricity distribution from large generation stations to the users is more efficient than the users themselves looking for solutions.

In terms of treating a patient, delivering energy over a distance affords great advantages as far as targeting accuracy, technologic flexibility, and importantly, limited invasiveness into the patient. In a simple form, laparoscopic surgery has replaced much of the previous open surgical procedures and lead to creation of new procedures and devices as well as a more efficient procedural flow for disease treatment. Laparoscopic tools deliver the surgeon's energy to the tissues of the patient from a distance and results in improved imaging of the region being treated as well as the ability for many surgeons to visualize the region at the same time. Perhaps most important is the fact that patients have much less pain, fewer complications, and the overall costs of the procedures are lower.

Continued advances in computing, miniaturization and economization of energy delivery technologies, and improved imaging will lead to still greater opportunities to apply energy from a distance into the patient and treat disease.

SUMMARY OF INVENTION

What is described herein are procedures and devices which advance the art of medical procedures involving transmitted energy to treat disease. That is, the procedures and devices described below follow along the lines of: 1) transmitting energy to produce an effect in a patient from a distance; 2) allowing for improved imaging or targeting at the site of treatment; 3) creating efficiencies through utilization of larger and more powerful devices from a position of distance from the patient as opposed to attempting to be directly in contact with the target.

In some embodiments, an imaging system is provided, as is a therapeutic delivery system.

In some embodiments, regions of the eye other than the retina are targeted with ablative or sub-ablative energy from outside the eye.

In some embodiments, the ciliary muscles are targeted and in some embodiments, the zonules surrounding the lens are targeted. In certain embodiments related to the eye, presbyopia is treated and in certain embodiments, elevated intraocular pressure is treated.

In some embodiments, the macula is targeted with non-ablative focused energy. Non-ablative focused or unfocused energy can be utilized to assist in the transscleral or intravitreal release of bioactive agents into the eye.

In some embodiments, non-focal, non-ablative energy is applied to the sclera to assist in the transscleral migration of bioactive materials to the choroidal space below the retina.

In some embodiments, ducts such as the fallopian tubes or the vas deferens are targeted for permanent or semi-permanent sterilization using ablative energy.

In some embodiments, vascular structures such as the saphenous vein, femoral vein, and iliac veins are directly targeted to treat venous diseases such as occlusions or faulty venous valves.

In some embodiments, intra-vascular clots, devices, or other vascular abnormalities such as aneurysms or arterial-venous malformations, are targeted.

In some embodiments, sympathetic nerves surrounding arteries are targeted for ablation or sub-ablative interruption. In some embodiments, the renal nerves which surround the pedicles of the kidneys are targeted. In some embodiments, circles or elliptical rings are created around the renal arteries and in some embodiments, the circles or rings are created closer to the bifurcation of the renal arteries as they reach the kidneys. In other embodiments, nerves running down the aorta are targeted as they branch off to the renal arteries. In some embodiments, the nerves are targeted at the dorsal or ventral roots as they leave the spinal canal.

In some embodiments, ultrasonic or ionizing energy is passed through the blood vessel to affect a change in the walls or the surroundings of the vessel.

In some embodiments, whole or partial sympathetic ganglia positioned close to blood vessels are targeted. In some embodiments, ganglia along the sympathetic chain along the spine are targeted as entire structures to target and alter physiologic processes. In other embodiments, the dorsal roots of the spinal cord are targeted with energy to partially or fully ablate the renal afferent nerves traveling through them.

In some embodiments, nerves to joints are targeted with ablative or non-ablative energy such as for example, the spine, the knee, or the hip.

In some embodiments, vessels are detected and placed in a coordinate frame to be treated with the focused energy system but regions (for example, nerves) just outside the vessels are treated. For example, the carotid artery, superior mesenteric artery, aorta, vena cava, renal veins, iliac arteries, ophthalmic artery, and ciliary arteries are all arteries which are potential targets for interruption of surrounding nerves, particularly autonomic nerves. The vessels, however, are the targets localized by the external imaging and energy delivery systems.

In some embodiments, a device and method to interrupt nerve fibers, at least partially, from a position external to a patient is described.

The embodiment involves the application of energy from a region external to the patient to the region of the nerve fibers. In some embodiments, energy is delivered from multiple directions and meet at the region of the nerve so as to deliver the effect.

In some embodiments, an external energy source delivers energy from two difference positions to focus energy on a region of interest (for example, the sympathetic nerve regions of the renal arteries).

In another embodiment, image detectors are embedded in the devices delivering the energy so that the imaging of the region of interest is also determined from two different angles to determine the location of the target in three dimensions.

In another embodiment, range finders (e.g. acoustic or sonar) are used to detect distances or positions of structures. Time of flight type analysis is the technical term to determined the distance and orientation of the blood vessel (e.g. Oraya).

In some embodiments, a renal artery is detected using doppler ultrasound technology. By detecting the position of the renal arteries from more than one angle via doppler triangulation, a three dimensional map can be created and the renal artery can be mapped into a coordinate reference frame. A pattern of energy can be applied to the renal artery based on the knowledge of the coordinate reference frame. Once the renal artery is placed in the coordinate frame, an algorithm is utilized to localize the delivery of focused ultrasound to heat the adventitia of the artery which contains the sympathetic nerves to the kidney and thereby decreasing the sympathetic stimulus to the kidney to potentially control hypertension, renal disease, and heart disease.

In one embodiment, ultrasound is passed through the posterior of a patient, avoiding the ribs and passing the ultrasound to the region of the renal arteries.

In other embodiments, vessels are detected via doppler ultrasound and placed in a coordinate frame to be treated with the focused energy system. For example, the carotid artery, superior mesenteric artery, aorta, vena cava, renal veins, iliac arteries, ophthalmic artery, and ciliary arteries are all arteries which are potential targets of sympathetic nerve interruption. In some embodiments, the techniques described can be applied to any other blood vessel adventitia or nerve plexus surrounding any blood vessel in the body.

In some embodiments, the location of the stomach is utilized because of its position overlying the celiac plexus and its position partially overlying the abdominal aorta. In this embodiment, a nasogastric tube is placed inside the stomach and can be utilized to stimulate or inhibit the celiac axis through the stomach wall using focused or non-focused energy sources.

In some embodiments, the celiac axis or associated nerves can also be directly ablated using energy based transducers through the stomach or through the aorta or from an external position.

In another embodiment, ionizing radiation is used and generated from equipment such as a megavoltage linear accelerator, proton beam accelerator, or orthovoltage X-ray generator.

In some embodiments, CT scan imaging or other imaging systems (for example, ultrasound), such as MRI can be used to target the region around the renal arteries where the sympathetic nerves sit.

In some embodiments, the ionizing radiation sources may also be coupled to CT or MRI scanners which can further aid in the identification of the region of the sympathetic nerve plexus.

In some embodiments, the ultrasound transducers are placed externally and the renal arteries are located in more than one axis using a doppler signal detected from the renal artery blood flow.

In some embodiments, an arrangement of the ultrasound transducers is such that each transducer has the ability to be moved relative to one another and with respect to the target (e.g. renal blood vessels, aorta, femoral arteries, veins etc.). Such movement allows for adjustment of focal distance and position in the X-Y plan which may change with position.

In some embodiments, a kidney and a renal artery, or just a kidney, is targeted with the ultrasound transducers.

In some embodiments, ultrasound transducers are used to detect Doppler blood flow and simulate the position of the heating spot at the focal region of the transducers. Focused ultrasound energy is then applied to the region surrounding the blood flow, utilizing the Doppler signal as the position to target.

In some embodiments, a three dimensional view of the renal arteries and renal pedicle is obtained using the ultrasonic images so that the heated region is simulated in three dimensions so as to avoid the critical structures around the renal pedicle such as the renal vein, adrenal artery, and the adrenal gland itself. In some embodiments, the ultrasound transducer scans the region to be treated to create a three dimensional image coordinate reference for the artery and arterial region. In some embodiments, heating of the renal vein is in fact permissible.

In some embodiments, a three-dimensional image of a renal artery enables precise placement of the heat generating spot because there are nerves proximal to the generated spot. In some embodiments, coupling of the renal artery doppler signal using two separate detectors allows the three dimensional coordinates of the renal artery to be determined in real space. In some embodiments, once the renal artery position is determined in real space, the 3D location of the heating via the therapeutic ultrasound transducers can be determined, in theory, quite quickly. Heating damage to organs surrounding the renal arteries can also be determined, modeled, and minimized.

In some embodiments, a puncture in the skin may be needed so as to take advantage of additional refinements in technology or to treat patients (e.g. obese patients) who are not amenable to completely external therapy. In this embodiment, the puncture in the skin may enable a catheter to be passed into an artery or vein and to the renal artery or vein. In some embodiments, a catheter is placed percutaneously, directly to the nerve region surrounding the vessels; that is, not transvascularly but through the skin into the retroperitoneum and to the region of the renal nerves.

In other embodiments, catheters may be placed through the subcutaneous tissues and into the space around the renal artery or vein. In either of these embodiments, the sympathetic nerves can be ablated or the nerve conduction pathways can otherwise be interrupted to result in a decrease in neurotransmitter release from the sympathetic terminals at the level of the kidney.

In addition to, or in place of, the renal sympathetic nerves, in some embodiments, it may be desirable to ablate or partially inhibit nerves which relate to the carotid or aortic baroreceptors. For example, cardiac afferent nerves have been known to dampen the carotid body response when activated which results in a loss of the parasympathetic response to elevated blood pressure. In such a scenario, the cardiac afferent nerves can be ablated so that the baroreceptor response remains sensitive to increased blood pressure and can stimulate the parasympathetic system to decrease adrenergic drive in the face of elevated blood pressure.

In some embodiments, the sympathetic or parasympathetic nerves leading to the eye are ablated, stimulated, partially ablated, or partially stimulated so as to control intraocular hypertension or other physiologic processes. These sympathetic nerves are well known as being causative for increases in intraocular pressure. Indeed, a best selling pharmaceutical, tenoptic, acts against the adrenergic response in the eye and so ablating the sympathetic nerves would offer a more permanent fix to the elevated intraocular blood pressure.

In one embodiment, the ultrasound transducers used for ablation also contain at least one imaging transducer. The imaging transducer can be utilized for quick imaging and registration with the MRI or the transducer can be utilized for detection of fiducials within the treatment region. Such fiducials can be placed in the field or may be naturally present such as for example, a Doppler flow signal in a renal artery. In one embodiment, an intravascular catheter is placed with a recognizeable beacon to indicate the position of the catheter, artery, and hence the nerves surrounding the artery.

In another embodiment, radiation (e.g. ionizing radiation) is applied to the region outside the artery to prevent re-growth of the sympathetic nerves after ablation.

In another embodiment, ablative energy is applied to a region of a fallopian tube to close the tube and prevent ovulation and transfer of ovum to a uterus.

In one embodiment, a method of inhibiting the function of a nerve traveling with an artery comprises; providing an external imaging modality to determine the location of the artery through the skin of a patient; placing the artery in a three dimensional coordinate reference based on the imaging; placing a therapeutic energy generation source in a three dimensional coordinate reference frame; coupling the three dimensional coordinate frame of the energy source and the artery; modeling the delivery of energy to the adventitial region of the artery or a region adjacent to the artery where a nerve travels; delivering therapeutic energy from the therapeutic energy source, from at least two different angles, through the skin of a patient, to intersect at an artery or the region adjacent to the artery to at least partially inhibit the function of a nerve.

In some embodiments, the imaging source is one of: ultrasound, MRI, and CT.

In some embodiments, the therapeutic energy is ultrasound. In some embodiments, the energy delivered to the region of the nerves is at the level of 10-100 watts/cm2 or 100-400 watts/cm2, 400-800 watts/cm2, 800-2 kW/cm2, 2-50 kW/cm2, 51-200 kW cm/2. In some instances the level is up to and exceeding 1 MW/cm2. In some embodiments, a duty cycle of 100% is utilized by the system and in some embodiments, the duty cycle is 50-99% or lower, for example, 1-49%.

In some embodiments, intensity is important and the dose is delivered over a period less than 2 seconds or less than 30 seconds or less than a minute. In some embodiments, energy delivered is not heat but vibratory energy with minimal heating.

In some embodiments, the artery is a renal artery.

In some embodiments the involve placing the artery in a three dimensional reference frame involving locating the artery using a doppler ultrasound signal.

In some embodiments, the fiducial is placed internal to the patient.

In some embodiments, the fiducial is temporarily placed in a position internal to the patient.

In some embodiments the fiducial is a catheter placed in the artery of the patient.

In some embodiments the catheter is detectable using an acoustic signal and said imaging modality is ultrasound.

In some embodiments, the method involves therapeutic energy from the energy source which is delivered in a distribution along the length of the artery.

In some embodiments the therapeutic energy is ionizing radiation.

In some embodiments, a system to inhibit the function of a nerve traveling with a renal artery comprises a detector to determine the location of the renal artery and renal nerve through the skin of a patient; an ultrasound component to deliver therapeutic energy through the skin from at least two directions to the nerve surrounding the renal artery; a modeling algorithm comprising an input and an output said input to the modeling algorithm comprising a three dimensional coordinate space containing a therapeutic energy source and the position of the renal artery; and, the output from the modeling algorithm comprises: the direction and energy level of the ultrasound component; a locateable fiducial, adapted to be temporarily placed in the artery of a patient and communicate with the detector to determine the location of the renal artery in a three dimensional reference, the information regarding the location transmittable as the input to the model.

In some embodiments, the fiducial is a passive reflector of ultrasound placed inside the artery.

In some embodiments, the fiducial has an air interface inside a balloon. In some embodiments, the fiducial is an intravascular balloon with air inside which can be detected from outside the patient.

In some embodiments, the system fiducial generates radiofrequency energy which is detectable outside the patient by a detector.

In some embodiments, the system fiducial is activated to transmit energy based on a signal from an ultrasound generator.

In some embodiments, the system output from the model instructs the ultrasound component to deliver a lesion on the artery in which the major axis of the lesion is longitudinal along the length of the artery.

In some embodiments, the system output from the model instructs the ultrasound component to deliver multiple lesions around an artery simultaneously. In some embodiments, the energy is delivered across the kidney with the energy crossing the kidney not affecting the kidney in any way.

In some embodiments, the system output from the model instructs the ultrasound component to deliver a circumferential lesion around the artery in which the HIFU overlap reaches across the artery and/or vein. In some embodiments, the ultrasound overlap has a maximal diameter of about 1 cm and covering the renal artery, the renal vein, and the renal nerves. Such energy can be applied within 30 s, 1 minute, or within 3-5 minutes.

In some embodiments, a lesion is placed around the renal artery just proximal to the bifurcation of the artery at the hilum of the kidney.

In some embodiments, a lesion is placed around the artery by targeting approximately the center of the artery.

In some embodiments, outflow restrictions are created in the kidney or in the renal vein (for example) to indicate a high pressure state to the kidney which will lead to the kidney autoregulating system blood pressure lower.

In some embodiments, a clinical feedback loop is utilized in which application of energy to control hypertension is followed by an assay for the effect, the assay might include one of: ultrasound of the kidneys, assessment of microneurometry in the periphery, biopsy of the kidney, evaluation of the concentration of norepinephrine in the blood.

In one embodiment, a skin patch acts as a detector of sympathetic activity, the sympathetic activity being altered by heat applied to one or more regions of the autonomic nervous system.

DETAILED DESCRIPTION OF THE INVENTION

Figure 1A:
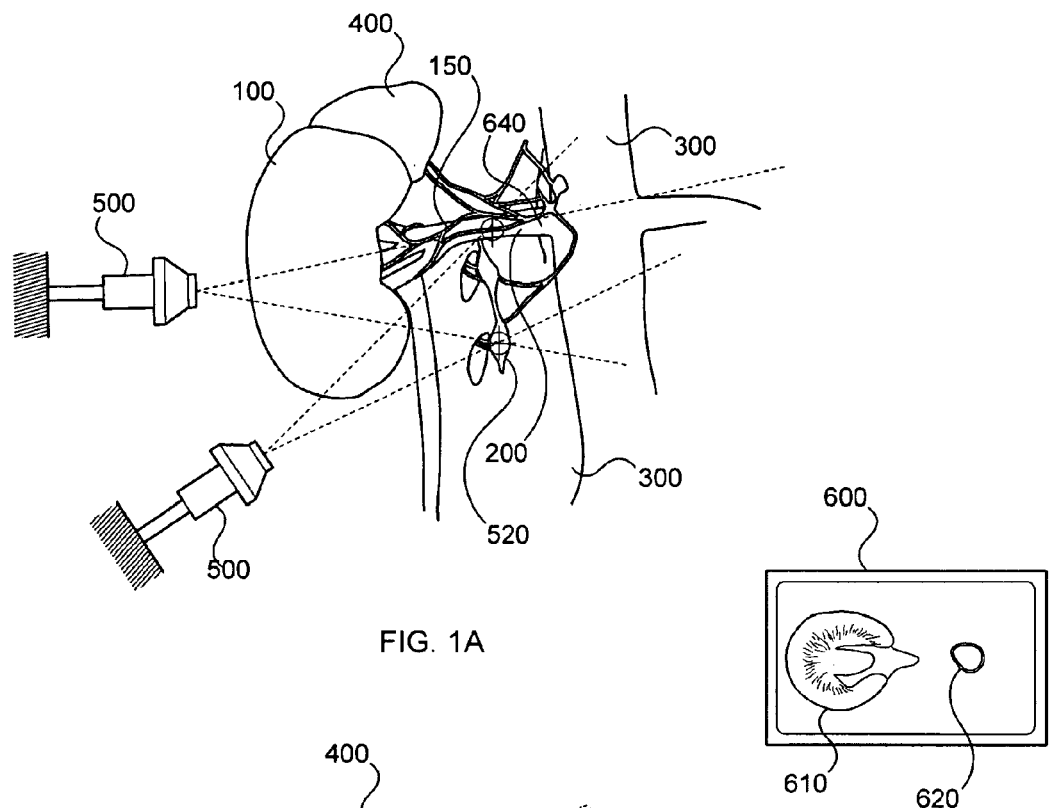
FIGS. 1a-1b depict the focusing of energy sources on nerves of the autonomic nervous system.
Figure 1C:
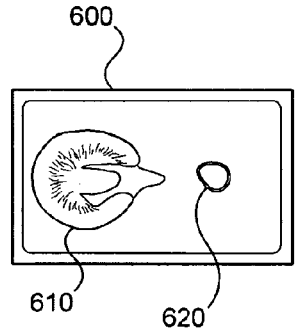
FIG. 1c depicts an imaging system.

Hypertension is a disease of extreme national and international importance. There are 80 million patients in the US alone who have hypertension and over 200 million in developed countries worldwide. In the United States, there are 60 million patients who have uncontrolled hypertension meaning that they are either non-compliant or cannot take the medication because of the side effect profile. Up to 10 million people might have completely resistant hypertension in which they do not reach target levels no matter what the medication regimen. The morbidities associated with uncontrolled hypertension are profound, including stroke, heart attack, kidney failure, peripheral arterial disease, etc. A convenient and straightforward minimally invasive procedure to treat hypertension would be a very welcome advance in the treatment of this disease.

Congestive Heart Failure ("CHF") is a condition which occurs when the heart becomes damaged and blood flow is reduced to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. For example, as the heart struggles to pump blood, the cardiac output is maintained or decreased and the kidneys conserve fluid and electrolytes to maintain the stroke volume of the heart. The resulting increase in pressure further overloads the cardiac muscle such that the cardiac muscle has to work harder to pump against a higher pressure. The already damaged cardiac muscle is then further stressed and damaged by the increased pressure. Moreover, the fluid overload and associated clinical symptoms resulting from these physiologic changes result in additional hospital admissions, poor quality of life, and additional costs to the health care system. In addition to exacerbating heart failure, kidney failure can lead to a downward spiral and further worsening kidney function. For example, in the forward flow heart failure described above, (systolic heart failure) the kidney becomes ischemic. In backward heart failure (diastolic heart failure), the kidneys become congested vis-à-vis renal vein hypertension. Therefore, the kidney can contribute to its own worsening failure.

The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys. The resulting hypertension also has dramatic influence on the progression of cerebrovascular disease and stroke.

The autonomic nervous system is a network of nerves which affect almost every organ and physiologic system to a variable degree. Generally, the system is composed of sympathetic and parasympathetic nerves. For example, the sympathetic nerves to the kidney traverse the sympathetic chain along the spine and synapse within the ganglia of the chain or within the celiac ganglia, then proceeding to innervate the kidney via post-ganglionic fibers inside the "renal nerves." Within the renal nerves, which travel along the renal hila (artery and to some extent the vein), are the post-ganglionic sympathetic nerves and the afferent nerves from the kidney. The afferent nerves from the kidney travel within the dorsal root (if they are pain fibers) and into the anterior root if they are sensory fibers, then into the spinal cord and ultimately to specialized regions of the brain. The afferent nerves deliver information from the kidneys back to the sympathetic nervous system via the brain; their ablation or inhibition is at least partially responsible for the improvement seen in blood pressure after renal nerve ablation, or dennervation, or partial disruption. It has also been suggested and partially proven experimentally that the baroreceptor response at the level of the carotid sinus is mediated by the renal artery afferent nerves such that loss of the renal artery afferent nerve response blunts the response of the carotid baroreceptors to changes in arterial blood pressure.

It has been established in animal models that the heart failure condition results in abnormally high sympathetic activation of the kidneys. An increase in renal sympathetic nerve activity leads to decreased removal of water and sodium from the body, as well as increased renin secretion which stimulates aldosterone secretion from the adrenal gland. Increased renin secretion can lead to vasoconstriction of blood vessels supplying the kidneys, which leads to a decrease in renal blood flow. Reduction in sympathetic renal nerve activity, e.g., via de-innervation, may reverse these processes. Similarly, in obese patients, the sympathetic drive is very high and is felt to be one of the causes of hypertension in obese patients.

Recent clinical work has shown that de-innervation of the renal sympathetic chain and other nerves which enter the kidney through the hilum can lead to profound systemic effects in patients with hypertension, heart failure, and other organ system diseases. Such treatment can lead to long term reduction in the need for blood pressure medications and improvements in blood pressure (O'Brien Lancet 2009 373; 9681 incorporated by reference). The devices used in this trial were highly localized radiofrequency (RF) ablation to ablate the renal artery adventitia with the presumption that the nerves surrounding the renal artery are being inhibited in the heating zone as well. The procedure is performed in essentially a blind fashion in that the exact location of the nerve plexus is not known prior to, during, or after the procedure. In addition, the wall of the renal artery is invariably damaged by the RF probe and patients whose vessels have a great deal of atherosclerosis cannot be treated safely. In addition, depending on the distance of the nerves from the vessel wall, the energy may not consistently lead to ablation or interruption. Finally, the use of internal catheters may not allow for treatment inside the kidney or inside the aorta if more selective or less selective blockade of the renal sympathetic nerves is desired.

Ultrasound is a cyclically generated sound pressure wave with a frequency greater than the upper limit of human hearing . . . 20 kilohertz (kHz). In medicine, ultrasound is widely utilized because of its ability to penetrate tissues. Reflection of the sound waves reveals a signature of the underlying tissues and as such, ultrasound can be used extensively for diagnostics and potentially therapeutics as well in the medical field. As a therapy, ultrasound has the ability to both penetrate tissues and can be focused to create ablation zones. Because of its simultaneous ability to image, ultrasound can be utilized for precise targeting of lesions inside the body. Ultrasound intensity is measured by the power per $cm^2$. Generally, high intensity refers to intensities over $1$ $kW/cm^2$. Low intensity ultrasound encompasses the rage up to $1$ $kW/cm^2$ from about 1 or 10 Watts per cm2.

Ultrasound can be utilized for its forward propagating waves and resulting reflected waves or where energy deposition in the tissue and either heating or slight disruption of the tissues is desired. For example, rather than relying on reflections for imaging, lower frequency ultrasonic beams (e.g. <1 MHz) can be focused at a depth within tissue, creating a heating zone or a defined region of cavitation in which microbubbles are created, cell membranes are opened to admit bioactive molecules, or damage is otherwise created in the tissue. These features of ultrasound generally utilize frequencies in the 0.25 Megahertz (MHz) to 10 MHz range depending on the depth required for effect. Focusing is or may be required so that the surface of the tissue is not excessively injured or heated by single beams. In other words, many single beams can be propagated through the tissue at different angles to decrease the energy deposition along any single path yet allow the beams to converge at a focal spot deep within the tissue. In addition, reflected beams from multiple angles may be utilized in order to create a three dimensional representation of the region to be treated in a coordinate space.

Time of flight measurements with ultrasound can be used to range find, or find distances between objects in tissues. Such measurements can be utilized to place objects such as vessels into three dimensional coordinate reference frames so that energy can be utilized to target the tissues. SONAR is the acronym for sound navigation and ranging and is a method of acoustic localization. Sound waves are transmitted through a medium and the time for the sound to reflect back to the transmitter is indicative of the position of the object of interest. Doppler signals are generated by a moving object. The change in the forward and reflected wave results in a velocity for the object.

Lithotripsy was introduced in the early part of the 1980's. Lithotripsy utilizes shockwaves to treat stones in the kidney. The Dournier lithotripsy system was the first system produced for this purpose. The lithotripsy system sends ultrasonic waves through the patient's body to the kidney to selectively heat and vibrate the kidney stones; that is, selectively over the adjacent tissue.

Histotripsy is a term given to a technique in which tissue is essentially vaporized using cavitation rather than heating (transcutaneous non-thermal mechanical tissue fractionation). These mini explosions do not require high temperature and can occur in less than a second. The generated pressure wave is in the range of megapascals (MPa) and even up to or exceeding 100 MPa. To treat small regions of tissue very quickly, this technique can be very effective. The border of the viable and non-viable tissue is typically very sharp and the mechanism of action has been shown to be cellular disruption.

Cross-sectional imaging is utilized to visualize the internal anatomy of patients via radiation (CT) or magnetic fields (MRI). Ultrasound can also be utilized to obtain cross-sections of specific regions but only at high frequencies; therefore, ultrasound is typically limited to imaging superficial body regions. CT and MRI are often more amenable to cross sectional imaging because the radiation penetrates well into tissues. In addition, the scale of the body regions is maintained such that the anatomy within the coordinate references remains intact relative to one another; that is, distances between structures can be measured.

With ultrasound, scaling can be more difficult because of unequal penetration as the waves propagate deeper through the tissue. CT scans and MRIs and even ultrasound devices can be utilized to create three dimensional representations and reconstructed cross-sectional images of patients; anatomy can be placed in a coordinate reference frame using a three dimensional representation. Once in the reference frame, energy devices (transducers) can be placed in positions and energy emitting devices directed such that specific regions of the body are targeted. Once knowledge of the transducer position is known relative to the position of the target in the patient body, energy can be delivered to the target.

In one embodiment, ultrasound is focused on the region of the renal arteries or veins from outside the patient; the ultrasound is delivered from multiple angles to the target, allowing the current invention to overcome many of the deficiencies in previous methods and devices put forward to ablate renal sympathetic nerves which surround the renal arteries.

Specifically, one embodiment of this invention allows for precise visualization of the ablation zone so that the operator can be confident that the correct region is ablated and that the incorrect region is not ablated. Because some embodiments do not require a puncture in the skin, they are considerably less invasive, which is more palatable and safer from the patient standpoint. Moreover, unusual anatomies and atherosclerotic vessels can be treated using external energy triangulated on the renal arteries to affect the sympathetic and afferent nerves to and from the kidney respectively.

With reference to FIG. 1A, the human renal anatomy includes the kidneys 100 which are supplied with oxygenated blood by the renal arteries 200 and are connected to the heart via the abdominal aorta 300. Deoxygenated blood flows from the kidneys to the heart via the renal veins (not shown) and thence the inferior vena cava (not shown). The renal anatomy includes the cortex, the medulla, and the hilum. Blood is delivered to the cortex where it filters through the glomeruli and is then delivered to the medulla where it is further filtered through a series of reabsorption and filtration steps in the loops of henle and individual nephrons; the ultrafiltrate then percolates to the ureteral collecting system and is delivered to the ureters and bladder for ultimate excretion.

The hila is the region where the major vessels (renal artery and renal vein) and nerves 150 (efferent sympathetic, afferent sensory, and parasympathetic nerves) travel to and from the kidneys. The renal nerves 150 contain post-ganglionic efferent nerves which supply sympathetic innervation to the kidneys.

Energy transducers 500 (FIG. 1a) deliver energy transcutaneously to the region of the sympathetic ganglia 520 or the post-ganglionic renal nerves 150 or the nerves leading to the adrenal gland 400. The energy is generated from outside the patient, from multiple directions, and through the skin to the region of the renal nerves 150 which surround the renal artery 640. The energy can be focused or non-focused but in one preferred embodiment, the energy is focused with high intensity focused ultrasound (HIFU). Focusing with low intensity focused ultrasound (LIFU) may also occur. Focusing occurs by delivering energy from at least two different angles through the skin to meet at a focal point where the highest energy intensity and density occurs. At this spot, a therapy is delivered and the therapy can be sub-threshold nerve interruption (partial ablation), ablation (complete interruption) of the nerves, controlled interruption of the nerve conduction apparatus, partial ablation, or targeted drug delivery. The region can be heated to a temperature of less than 60 degrees for non-ablative therapy or can be heated greater than 60 degrees for heat based destruction (abalation). To ablate the nerves, even temperatures in the 40 degree range can be used and if generated for a time period greater than several minutes, will result in ablation. Heating aside, a vibratory effect for a much shorter period of time at temperatures below 60 degrees Celsius can result in partial or complete paralysis of destruction of the nerves. If the temperature is increased beyond 50-60 degrees, the time required for heating is decreased considerably to affect the nerve via the sole mechanism of heating. In some embodiments, an imaging modality is included as well in the system. The imaging modality can be ultrasound based, MRI based, CT (Xray) based. The imaging modality can be utilized to target the region of ablation and determined the distances to the target.

The delivered energy can be ionizing or non-ionizing energy. Forms of non-ionizing energy can include electromagnetic energy (e.g. a magnetic field, light, an electric field), radiofrequency energy, and light based energy. Forms of ionizing energy include x-ray, proton beam, gamma rays, electron beams, and alpha rays. In some embodiments, the energy modalities are combined. For example, heat ablation of the nerves is performed and then ionizing radiation is delivered to the region to prevent re-growth of the nerves.

Alternatively, ionizing radiation is applied first as an ablation modality and then heat applied afterward in the case of re-growth of the tissue as re-radiation may not be possible (complement energy utilization). Ionizing radiation may prevent or inhibit the re-growth of the nervous tissue around the vessel if there is indeed re-growth of the nervous tissue. Therefore, another method of treating the nerves is to first heat the nerves and then apply ionizing radiation to prevent re-growth.

In some embodiments, external neuromodulation is performed in which low energy ultrasound is applied to the nerve region to modulate the nerves. For example, it has been shown in the past that low intensity (e.g. non-thermal) ultrasound can affect nerves at powers which range from 30-500 mW/Cm$^2$ whereas HIFU (thermal modulation), by definition generates heat at a focus, requires power levels exceeding 1000 W/Cm$^2$. The actual power flux to the region to be ablated is dependent on the environment including surrounding blood flow and other structures. With low intensity ultrasound, the energy does not have to be so strictly focused to the target because it's a non-ablative energy; that is, the vibration or mechanical pressure may be the effector energy and the target may have a different threshold for effect depending on the tissue. However, even low energy ultrasound may require focusing if excessive heat to the skin is a worry or if there are other susceptible structures in the path and only a pinpoint region of therapy is desired. Nonetheless, transducers 500 in FIG. 1*a* provide the ability to apply a range of different energy and power levels as well as modeling capability to target different regions and predict the response.

In FIG. 1*a*, and in one embodiment, a renal artery is detected 640 with the assistance of imaging techniques 600 such as Doppler ultrasound, B-mode ultrasound, MRI, or a CT scan. With an image of the region to be treated, measurements in multiple directions on a series of slices can be performed so as to create a three-dimensional representation of the area of interest. By detecting the position of the renal arteries from more than one angle via Doppler triangulation (for example) or another triangulation technique, a three dimensional positional map can be created and the renal artery can be mapped into a coordinate reference frame. In this respect, given that the renal nerves surround the renal blood vessels in the hilum, locating the direction and lengths of the blood vessels in three dimensional coordinate reference is the predominant component of the procedure to target the sympathetic nerves. Within the three dimensional reference frame, a pattern of energy can be applied to the vicinity of the renal artery from a device well outside the vicinity (and outside of the patient altogether) based on knowledge of the coordinate reference frame.

For example, once the renal artery is placed in the coordinate reference frame with the origin of the energy delivery device, an algorithm is utilized to localize the delivery of focused ultrasound to heat or apply mechanical energy to the adventitia and surrounding regions of the artery which contain sympathetic nerves to the kidney and afferent nerves from the kidney, thereby decreasing the sympathetic stimulus to the kidney and its afferent signaling back to the autonomic nervous system; affecting these targets will modulate the propensity toward hypertension which would otherwise occur. The ultrasonic energy delivery can be modeled mathematically by predicting the wave dissipation using the distances and measurements taken with the imaging modalities of the tissues and path lengths.

In one embodiment of an algorithm, the Doppler signal from the artery is identified from at least two different directions and the direction of the artery is reconstructed in three dimensional space. With two points in space, a line is created and with knowledge of the thickness of the vessel, a tube, or cylinder, can be created to represent the blood vessel as a virtual model. The tube is represented in three dimensional space over time and its coordinates are known relative to the therapeutic transducers outside of the skin of the patient. Therapeutic energy can be applied from more than one direction as well and can focus on the cylinder (blood anterior vessel wall, central axis, or posterior wall.

Focused energy (e.g. ultrasound) can be applied to the center of the vessel (within the flow), on the posterior wall of the vessel, in between (e.g. when there is a back to back artery and vein next to one another) the artery vessel and a venous vessel, etc.

Imaging 600 of the sympathetic nerves or the sympathetic region (the target) is also utilized so as to assess the direction and orientation of the transducers relative to the target 620. Continuous feedback of the position of the transducers 500 relative to the target 620 is provided by the imaging system in which the coordinate space of the imaging system. The imaging may be a cross-sectional imaging technology such as CT or MRI or it may be an ultrasound imaging technology which yields faster real time imaging. In some embodiments, the imaging may be a combination of technologies such as the fusion of MRI/CT and ultrasound. The imaging system can detect the position of the target in real time at frequencies ranging from 1 hz to thousands and tens of thousands of images per second.

In the example of fusion, cross-sectional imaging (e.g. MRI/CT) is utilized to place the body of the patient in a three dimensional coordinate frame and then ultrasound is linked to the three dimensional reference frame and utilized to track the patient's body in real time under the ultrasound linked to the cross-sectional imaging. The lack of resolution provided by the ultrasound is made up for by the cross-sectional imaging since only a few consistent anatomic landmarks are required for an ultrasound image to be linked to the MRI image. As the body moves under the ultrasound, the progressively new ultrasound images are linked to the MRI images and therefore MRI "movement" can be seen at a frequency not otherwise available to an MRI series.

In one embodiment, ultrasound is the energy used to inhibit nerve conduction in the sympathetic nerves. In one embodiment, focused ultrasound (HIFU) from outside the body through the skin is the energy used to inhibit sympathetic stimulation of the kidney by delivering waves from a position external to the body of a patient and focusing the waves on the sympathetic nerves on the inside of the patient and which surround the renal artery of the patient.

Figure 3A:
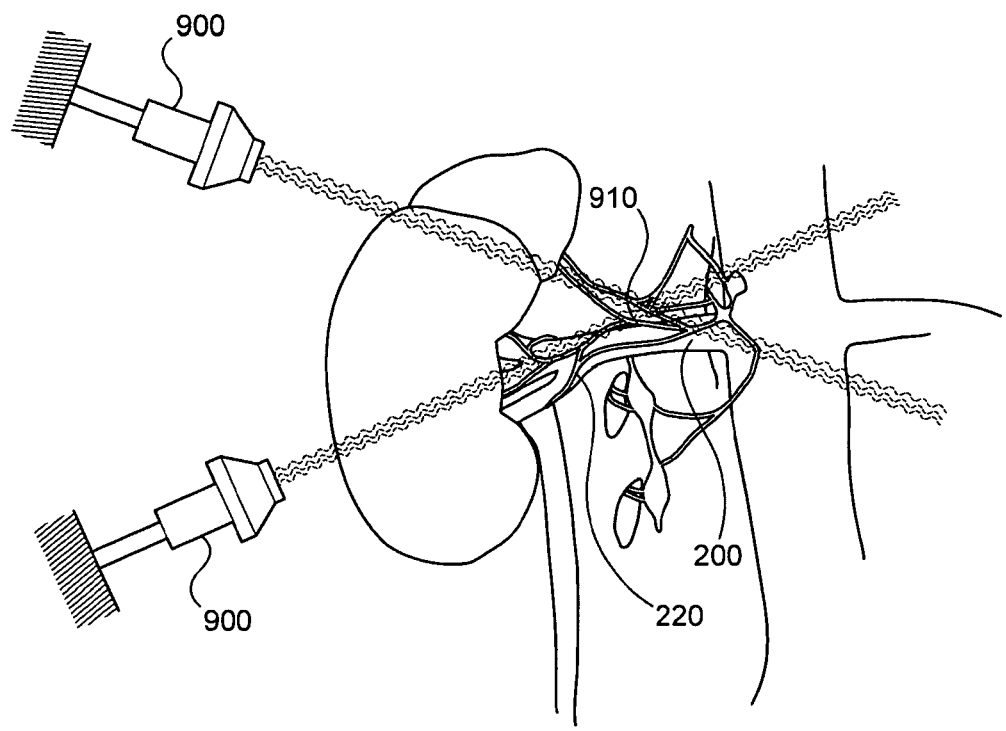
FIG. 3a depicts focusing of energy waves on the renal nerves
Figure 3B:
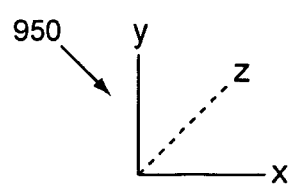
FIG. 3b depicts a coordinate reference frame

As is depicted in FIG. 3, transducers 900 can emit ultrasound energy to the region of the renal sympathetic nerves at the renal pedicle. As shown in FIG. 1*a*, an image of the renal artery 620 using an ultrasound, MRI, or CT scan can be utilized to determine the position of the kidney 610 and the renal artery 620 target. Doppler ultrasound can be used to determine the location and direction of a Doppler signal from an artery and therefore enable the arteries 200 and hence the sympathetic nerves 220 (FIG. 3*a*) around the artery to be much more visible so as to process the images and then utilize focused external energy to pinpoint the location and therapy of the sympathetic nerves. In this embodiment, ultrasound is likely the most appropriate imaging modality.

FIG. 1*a* also depicts the delivery of focused energy to the sympathetic nerve trunks which run along the vertebral column; the renal artery efferent nerves travel in these trunks and synapse to ganglia within the trunks. In another embodiment, ablation of the dorsal roots at the level of the ganglia or dorsal root nerves at T9-T11 (through which the afferent renal nerves travel) would produce the same or similar effect to ablation at the level of the renal arteries.

Figure 1B:
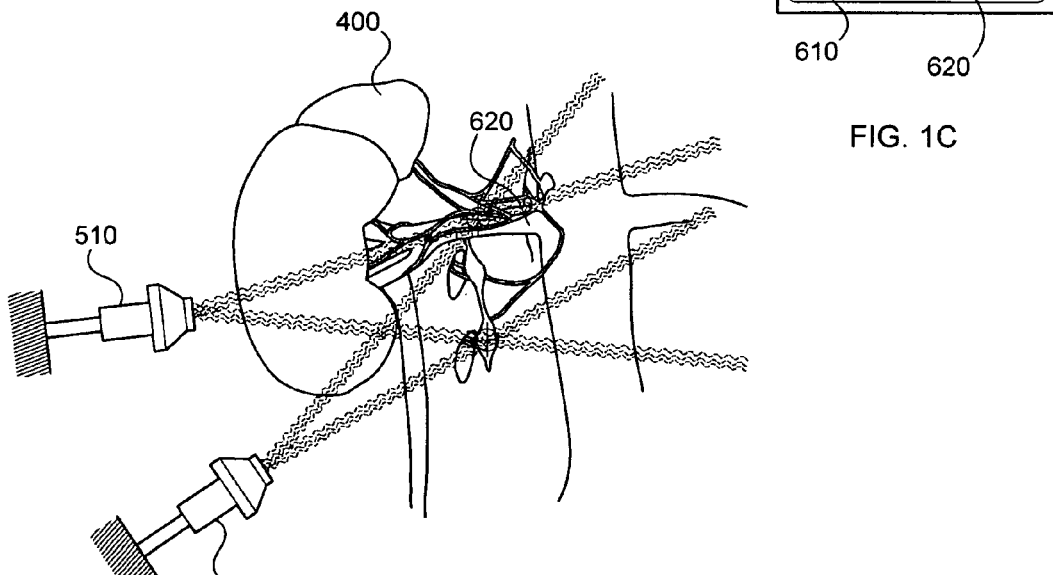

FIG. 1*b* illustrates the application of ionizing energy to the region of the sympathetic nerves on the renal arteries 620 or renal veins. In general, energy levels of greater than 20 Gy (Gray) are required for linear accelerators or low energy x-ray machines to ablate nervous tissue using ionizing energy; however, lower energy is required to stun, inhibit nervous tissue, or prevent re-growth of nervous tissue; in some embodiment, energy levels as low as 2-5 Gy or 5-10 Gy or 10-15 Gy are delivered in a single or fractionated doses.

Combinations of ionizing energy and other forms of energy can be utilized in this embodiment as well so as to prevent re-growth of the nervous tissue. For example, a combination of heat and/or vibration and/or cavitation and/or ionizing radiation might be utilized to prevent re-growth of nervous tissue after the partial or full ablation of the nervous tissue surrounding the renal artery.

Figure 2:
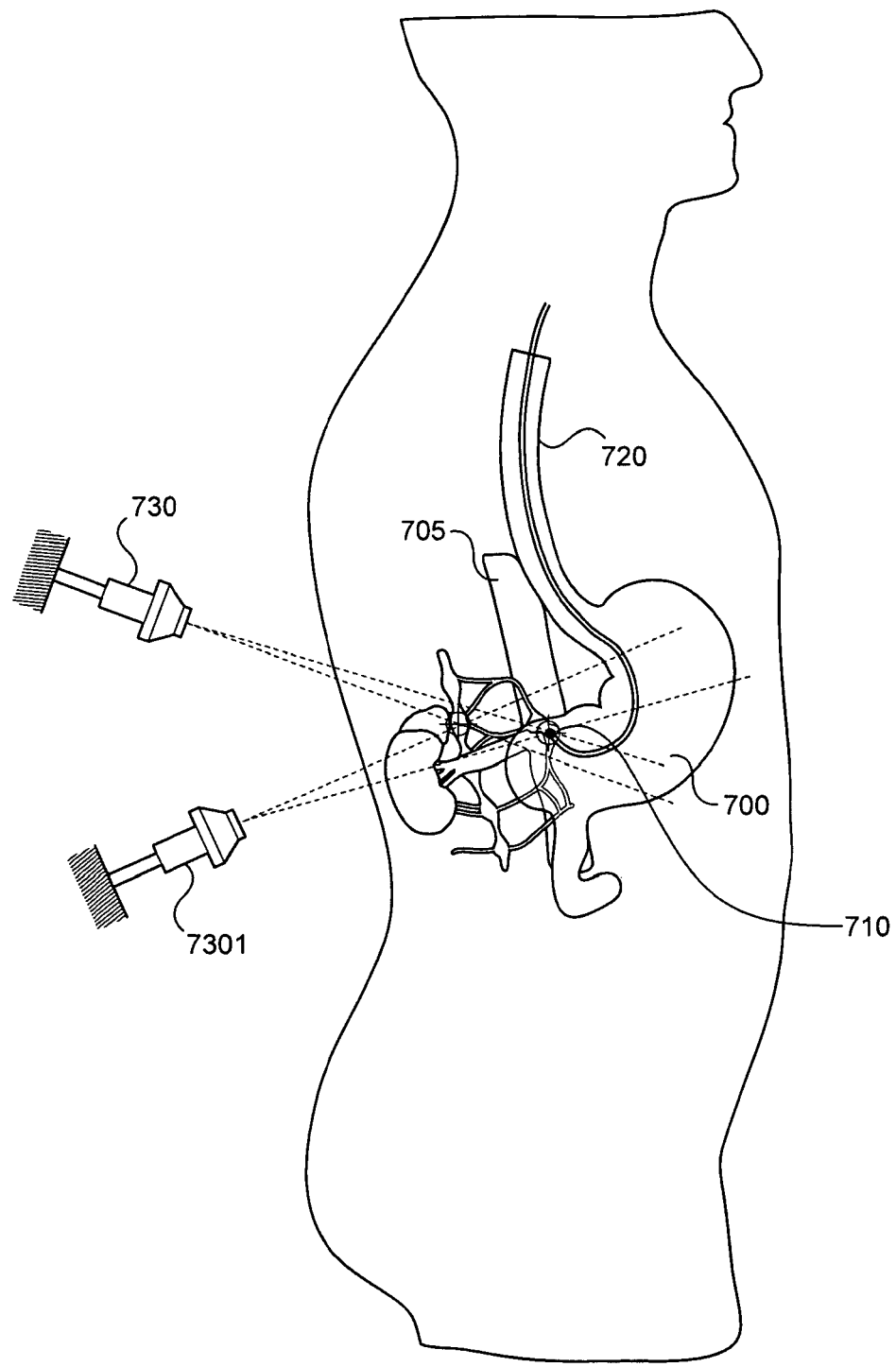
FIG. 2 depicts targeting and/or therapeutic ultrasound delivered through the stomach to the autonomic nervous system posterior to the stomach.

FIG. 2 illustrates the renal anatomy and surrounding anatomy with greater detail in that organs such as the stomach are shown in its anatomic position overlying the abdominal aorta and renal arteries. In this embodiment, energy is delivered through the stomach to reach an area behind the stomach. In this embodiment, the stomach is utilized as a conduit to access the celiac ganglion, a region which would otherwise be difficult to reach. The aorta 705 is shown underneath the stomach and the celiac ganglion 710 is depicted surrounding the superior mesenteric artery and aorta. A transorally placed tube 720 is placed through the esophagus and into the stomach. The tube overlies the celiac ganglion when placed in the stomach and can therefore be used to deliver sympatholytic devices or pharmaceuticals which inhibit or stimulate the autonomic celiac ganglia behind the stomach; these therapies would be delivered via transabdominal ultrasound or fluoroscopic guidance (for imaging) through the stomach. Similar therapies can be delivered to the inferior mesenteric ganglion, renal nerves, or sympathetic nerves traveling along the aorta through the stomach or other portion of the gastrointestinal tract. The energy delivery transducers 730,731 are depicted external to the patient and can be utilized to augment the therapy being delivered through the stomach to the celiac ganglion.

Temporary neurostimulators can also be placed through the tube, such as, for example, in an ICU setting where temporary blockage of the autonomic ganglia may be required. Temporary neurostimulators can be used to over pace the celiac ganglion nerve fibers and inhibit their function as a nerve synapse. Inhibition of the celiac ganglion may achieve a similar function as ablation or modulation of the sympathetic nerves around the renal arteries. That is, the decrease in the sympathetic activity to the kidneys (now obtained with a more proximal inhibition) leads to the lowering of blood pressure in the patient by decreasing the degree of sympathetic outflow from the sympathetic nerve terminals. In the celiac ganglia, the blood pressure lowering effect is more profound given that the celiac ganglia are pre-ganglionic and have more nerve fibers to a greater number of regions than each renal nerve. The effect is also likely more permanent than the effect on the post-ganglionic nerve fibers.

FIG. 3a illustrates the renal anatomy more specifically in that the renal nerves 220 extending longitudinally along the renal artery 200, are located generally within, or just outside the adventitia, of the outer portion of the artery. Arteries are typically composed of three layers: the first is the intimal, the second is the media, and the third is the adventitia. The outer layer, the adventitia, is a fibrous tissue which contains blood vessels and nerves. The renal nerves are generally postganglionic sympathetic nerves although there are some ganglia which exist distal to the takeoff from the aorta such that some of the nerve fibers along the renal artery are in fact pre-ganglionic. By the time the fibers reach the kidney, the majority of the fibers are post-ganglionic.

Energy generators 900 deliver energy to the renal nerves accompanying the renal artery, depositing energy from multiple directions to target inhibition of the renal nerve complex. The energy generators can deliver ultrasound energy, ionizing radiation, light (photon) therapy, or microwave energy to the region. The energy can be non-focused in the case where a pharmaceutical agent is targeted to the region to be ablated or modulated. Preferably, however, the energy is focused, being applied from multiple angles from outside the body of the patient to reach the region of interest (e.g. sympathetic nerves surrounding blood vessels). The energy transducers 900 are placed in an X-Y-Z coordinate reference frame 950, as are the organs such as the kidneys. Once in the coordinate reference frame, cross-sectional imaging using MRI, CT scan, and/or ultrasound is utilized to couple the internal anatomy to the energy transducers. The transducers 900 in this embodiment are focused on the region of the renal nerves at the level of the renal blood vessels, the arteries and veins.

When applying ultrasonic energy across the skin to the renal artery region, energy densities of potentially over 1 $MW/cm^2$ might be required so as to reach the region of interest. The energy may be pulsed across the skin in an unfocused manner; however, for application of heat, the transducers must be focused otherwise the skin and underlying tissues will receive too much heat. Under imaging with MRI, temperature can be measured with the MRI image. When low energy ultrasound is applied to the region, energy densities in the range of 50 $mW/cm^2$ to 500 $mW/cm^2$ may be applied. Low energy ultrasound may be enough to stun or partially inhibit the renal nerves. High intensity ultrasound applied to the region with only a few degrees of temperature rise may have the same effect and this energy range may be in the 0.5 kW/cm2 to the 500 kW/cm2 range. In some of the embodiments, cooling may be applied to the skin if the temperature rise is deemed too large to be acceptable. Alternatively, the ultrasound transducers can be pulsed or can be alternated with another set of transducers to effectively spread the heat across the surface of the skin.

In one method of altering the physiologic process of renal sympathetic excitation, the region around the renal arteries is imaged using CT scan, MRI, thermography, infrared imaging, optical coherence tomography (OCT), photoacoustic imaging, pet imaging, SPECT imaging, or ultrasound, and the images are placed into a three dimensional coordinate reference frame. Energy transducers which can deliver ultrasound, light, radiation, ionizing radiation, or microwave energy are placed in the same three-dimensional reference frame as the renal arteries at which time an algorithm can determine how to direct the transducers to deliver energy to the region of the nerves. The algorithm consists of a targeting feature (planning feature) which allows for prediction of the position and energy deposition of the energy leaving the transducer. Once the three dimensional coordinate reference frames are linked or coupled, the planning and prediction algorithm can be used to precisely position the energy beams at a target in the body.

The original imaging utilized to locate the renal sympathetic region can be used to track the motion of the region during treatment. For example, the imaging technology used at time zero is taken as the baseline scan and subsequent scans at time t1 are compared to the baseline scan. The frequency of updates can range from a single scan every few seconds to many scans per second. With ultrasound as the imaging technology, the location might be updated at a frame rate greater than 50 Hz and up to several hundred Hz or thousand Hz. With MRI as the imaging modality, the imaging refresh rate might be closer to 30 Hz. In other embodiments, internally placed fiducials transmit positional information at a high frequency and this information is utilized to fuse the target with an initial external imaging apparatus. Internal fiducials might be one more imageable elements including doppler signal, regions of blood vessels, ribs, kidneys, blood vessels other than the target (e.g. vena cava). These fiducials can be used to track the region being treated and/or to triangulate to the region to be treated.

A test dose of energy can be applied to the renal sympathetic region and then a test performed to determine if an effect was created. For example, a small amount of heat can be delivered to the region of the sympathetic nerves and then a test of sympathetic activity such as microneurometry (detection of sympathetic nerve activity around muscles and nerves which correlate with the beating heart) can be performed. Past research and current clinical data have shown that the sympathetic nerves to the peripheral muscles are affected by interruption of the renal afferent nerves. The temperature rise with the small degree of heat can be determined through the use of MRI thermometry and the temperature rise can be determined or limited to an amount which is reversible.

Alternatively, ultrasonic imaging can be utilized to determine the approximate temperature rise of the tissue region. The speed of ultrasonic waves is dependent on temperature and therefore the relative speed of the ultrasound transmission from a region being heated will depend on the temperature, therefore providing measureable variables to monitor. In some embodiments, microbubbles are utilized to determine the rise in temperature. Microbubbles expand and then degrade when exposed to increasing temperature so that they can then predict the temperature of the region being heated. A technique called ultrasound elastography an also be utilized. In this embodiment, the elastic properties of tissue are dependent on temperature and therefore the elastography may be utilized to track features of temperature change. The microbubbles can also be utilized to augment the therapeutic effect of the region being targeted. For example, the microbubbles can be utilized to release a pharmaceutical when the ultrasound reaches them.

In another embodiment, a test may be performed on the baroreceptor complex at the region of the carotid artery bifurcation. After the test dose of energy is applied to the renal artery complex, pressure can be applied to the carotid artery complex; typically, with an intact baroreceptor complex, the systemic blood pressure would decrease after application of pressure to the carotid artery. However, with renal afferent nerves which have been inhibited, the baroreceptors will not be sensitive to changes in blood pressure and therefore the efficacy of the application of the energy to the renal nerves can be determined.

Figure 4:
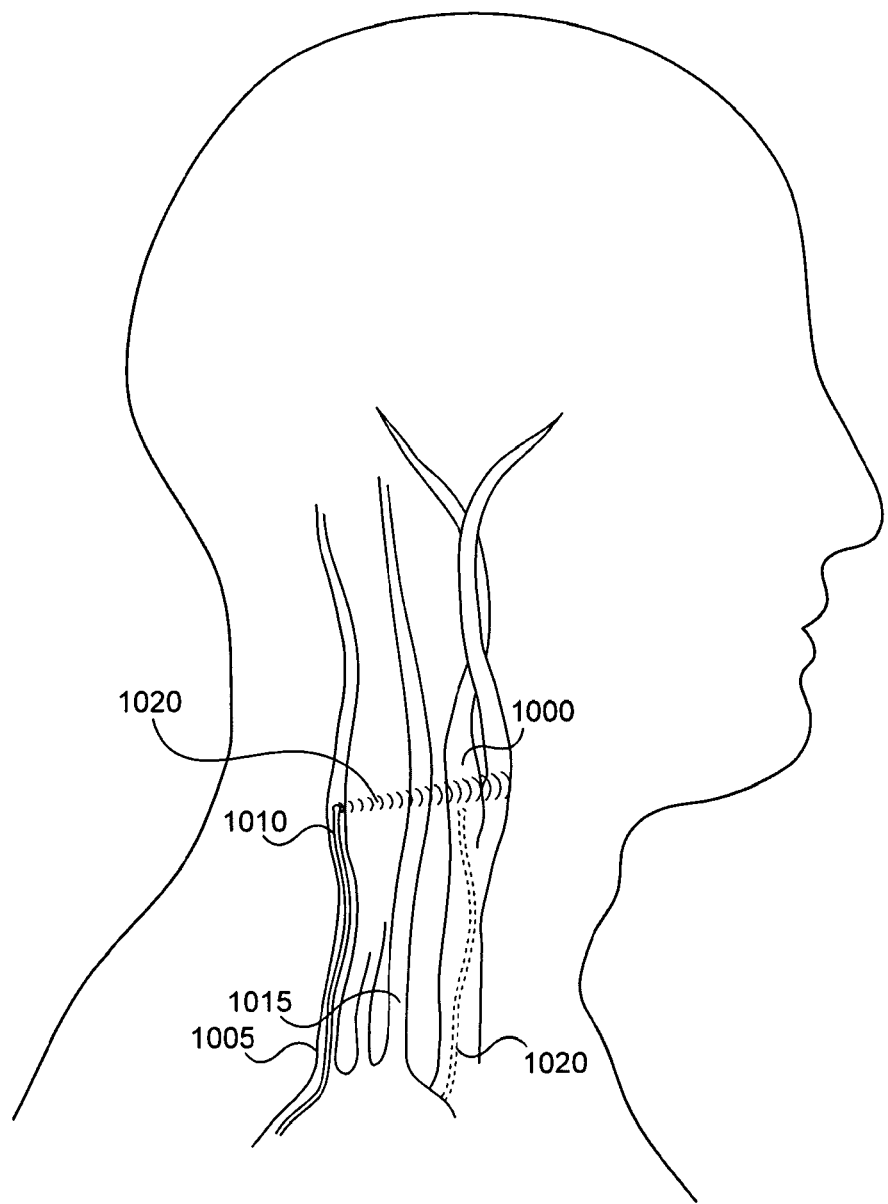
FIG. 4 depicts the application of energy to the autonomic nervous system surrounding the carotid arteries

Other regions of the autonomic nervous system can also be affected directly by the technology in this invention by applying energy from one region to another. For example, FIG. 4 illustrates a system in which external energy 1020 is applied to a portion of the autonomic nervous system, the carotid body complex 1000, through the internal jugular vein 1005, and to the carotid body 1000 and/or vagus nerve 1020 region. Ablative energy or electrical stimulation energy can be utilized to affect the transmission of signals to and from these nerves. The transmission in this complex can be augmented, interrupted, inhibited with over-stimulation, or a combination of these effects via energy (e.g. ultrasound, electrical stimulation, etc.)

A catheter 1010 is advanced into the internal jugular vein 1005 and when in position, stimulation or ablative energy 1020 is directed toward the autonomic nerves, the vagus nerve, and the carotid sinus from the catheter positioned in the venous system. A similar type of catheter can be inserted into the region of the renal arteries or renal veins to stimulate or inhibit the renal nerves from the inside of the vessel. For example, a catheter delivering unfocused ultrasound energy in the range of 50 mW/cm$^2$ to 50 W/cm$^2$ can be placed into the renal artery and the energy transmitted radially around the artery to the nerves.

This therapy can be delivered on an acute basis such as for example in an ICU or critical care setting. In such a case, the therapy would be acute and intermittent, with the source outside the patient and the catheter within the patient as shown in FIG. 4. The therapy can be utilized during times of stress for the patient such that the sympathetic system is slowed down. After the intensive care admission is nearing a close, the catheter and unit can be removed from the patient.

Figure 5A:
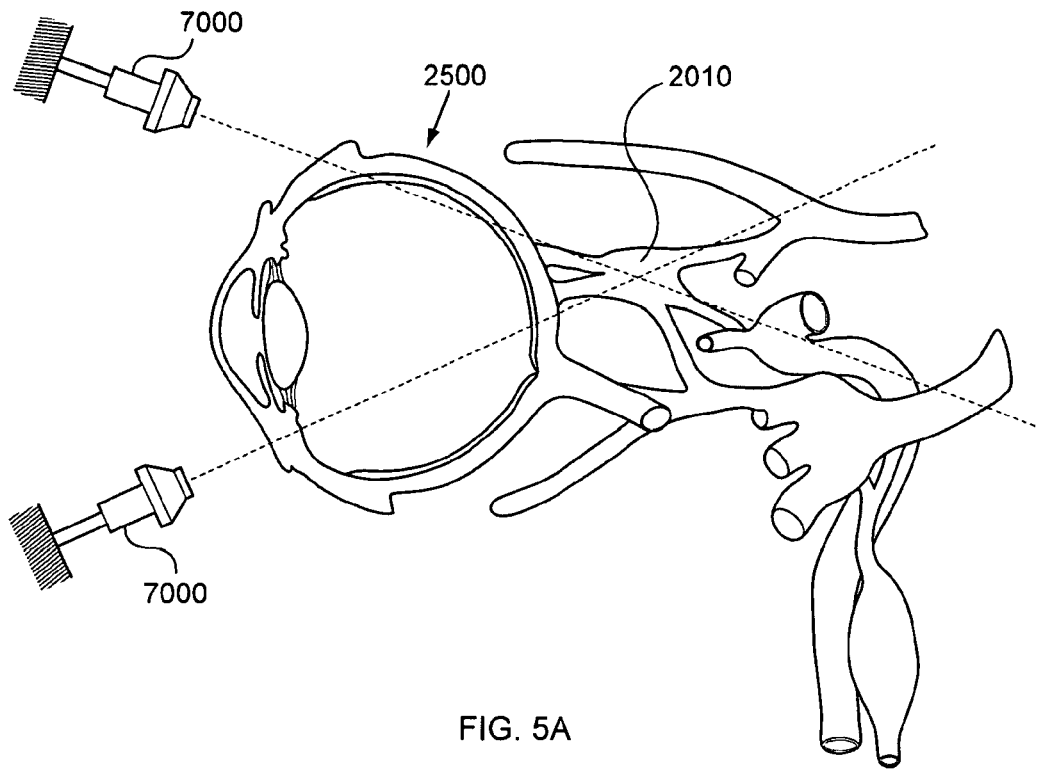
FIGS. 5a-5b depict the application of focused energy to the autonomic nervous system of the eye.
Figure 5B:
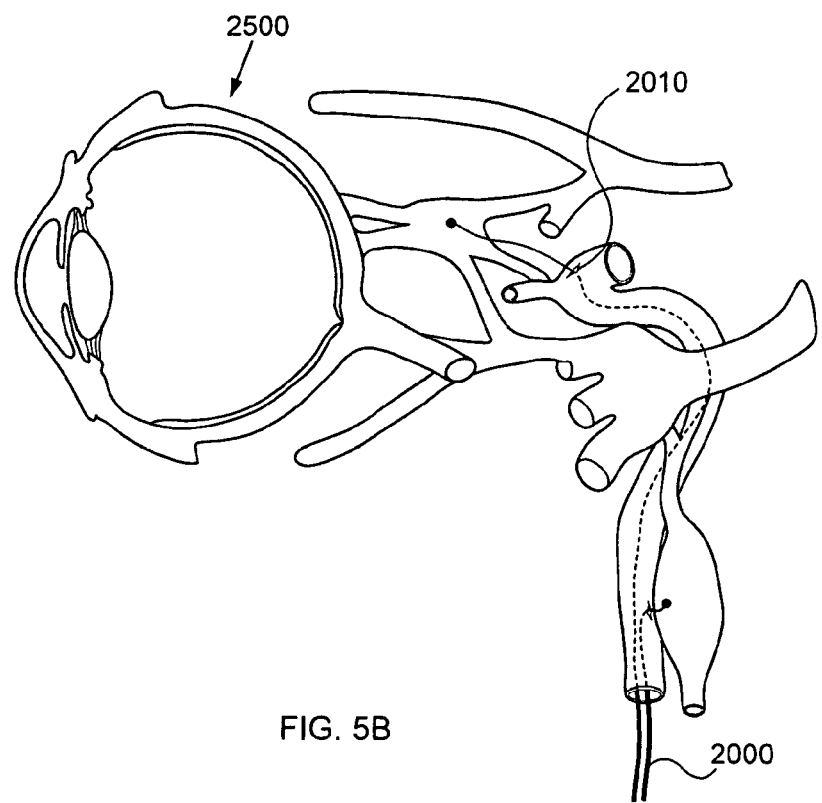

FIGS. 5a-b illustrates the eye in close up detail with sympathetic nerves surrounding the posterior of the eye. In the eye, glaucoma is a problem of world-wide importance. The most commonly prescribed medication to treat glaucoma is timoptic, which is a non-selective β1 and β2 (adrenergic) antagonist. Compliance with this pharmaceutical is a major problem and limits its effectiveness in preventing the complications of glaucoma, the major complication being progression of visual dysfunction.

Ultrasound, or other energy transducers 7000, can be applied to focus energy from an external region (e.g. a distance from the eye in an external location) anterior to the eye or to a region posteriorly behind the eye 2500 on the sympathetic 2010 or parasympathetic ganglia, all of which will affect lowering of intra-ocular pressure. The energy transducers 700 apply ablative or near ablative energy to the adventitia of the blood vessel. In some embodiments, the energy is not ablative but vibratory at frequencies and penetration depths sufficient to inhibit the function of the nerves which are responsible for intra-ocular pressure.

FIG. 5b depicts the anatomy behind the eye. In this illustration, a catheter 2000 is tunneled through the vasculature to the region of the sympathetic nerves surrounding the arteries of the eye 2010 and utilized to ablate, stun, or otherwise modulate the efferent and/or afferent nerves through the wall of the vasculature.

Figure 6:
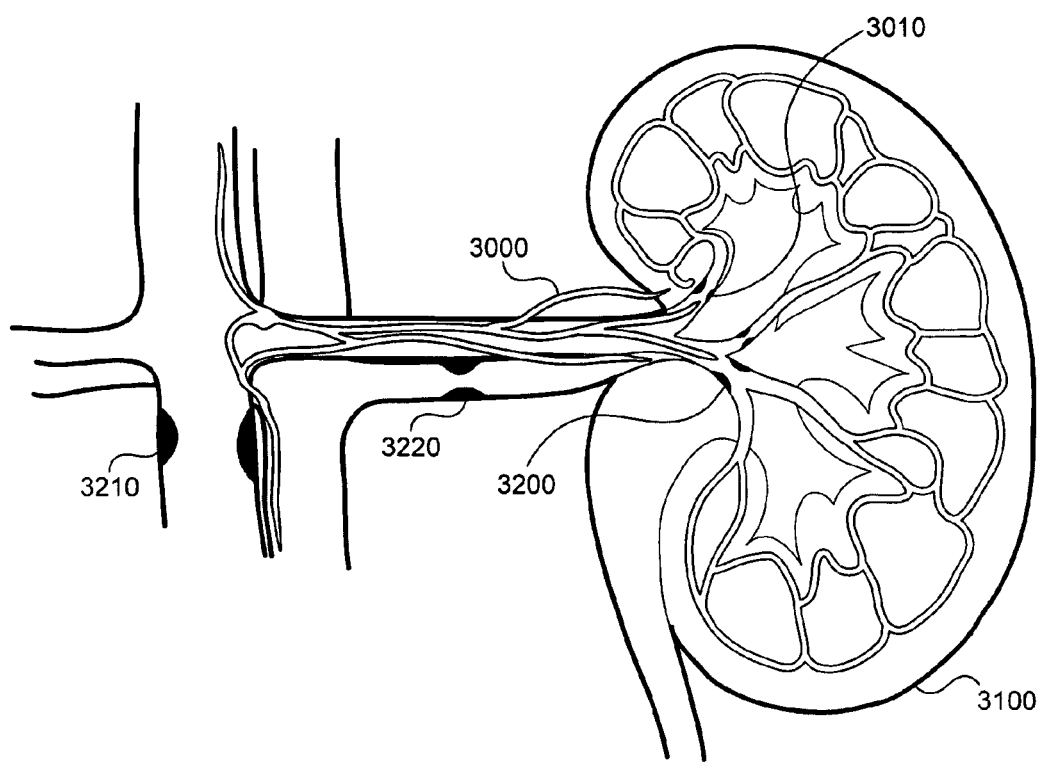
FIG. 6 depict the application of lesions to the kidney deep inside the calyces.

FIG. 6 illustrates an overall schematic of the renal artery, renal vein, the collecting system, and the more distal vessels and collecting system within the renal parenchyma. The individual nerves of the autonomic nervous system typically follow the body vasculature and they are shown in close proximity 3000 to the renal artery as the artery enters the kidney 3100 proper. Any one or multiple of these structures can influence the function of the kidney. Ablative or non-ablative energy can be applied to the renal vein, the renal artery, the aorta or the vena cava, the renal hilum, the renal parenchyma, the renal medulla, the renal cortex, etc.

In one embodiment, selective lesions, constrictions or implants 3200 are placed in the calyces of the kidney to control or impede blood flow to specific regions of the kidney. Such lesions or implants can be placed on the arterial 3010 or venous sides 3220 of the kidney. In some embodiments, the lesions/implants are created so as to selectively block certain portions of the sympathetic nerves within the kidney. The lesions also may be positioned so as to ablate regions of the kidney which produce hormones, such as renin, which can be detrimental to a patient in excess. The implants or constrictions can be placed in the aorta 3210 or the renal vein 3220. The implants can be active implants, generating stimulating energy chronically or multiple ablative or inhibitory doses discretely over time.

In the renal vein, the implants might cause an increase in the pressure within the kidney which will prevent the downward spiral of systolic heart failure described above. That is, once the pressure in the kidney is restored or artificially elevated by increased venous pressure, the relative renal hypotension signaling to retain electrolytes and water will not be present any longer and the kidney will "feel" full and the renal sympathetic stimulation will be turned off. In one embodiment, a stent which creates a stenosis is implanted using a catheter delivery system 3000. In another embodiment, a stricture is created using heat delivered either externally or internally. In one embodiment, an implant is placed between girota's fascia and the cortex of the kidney.

Figure 7A:
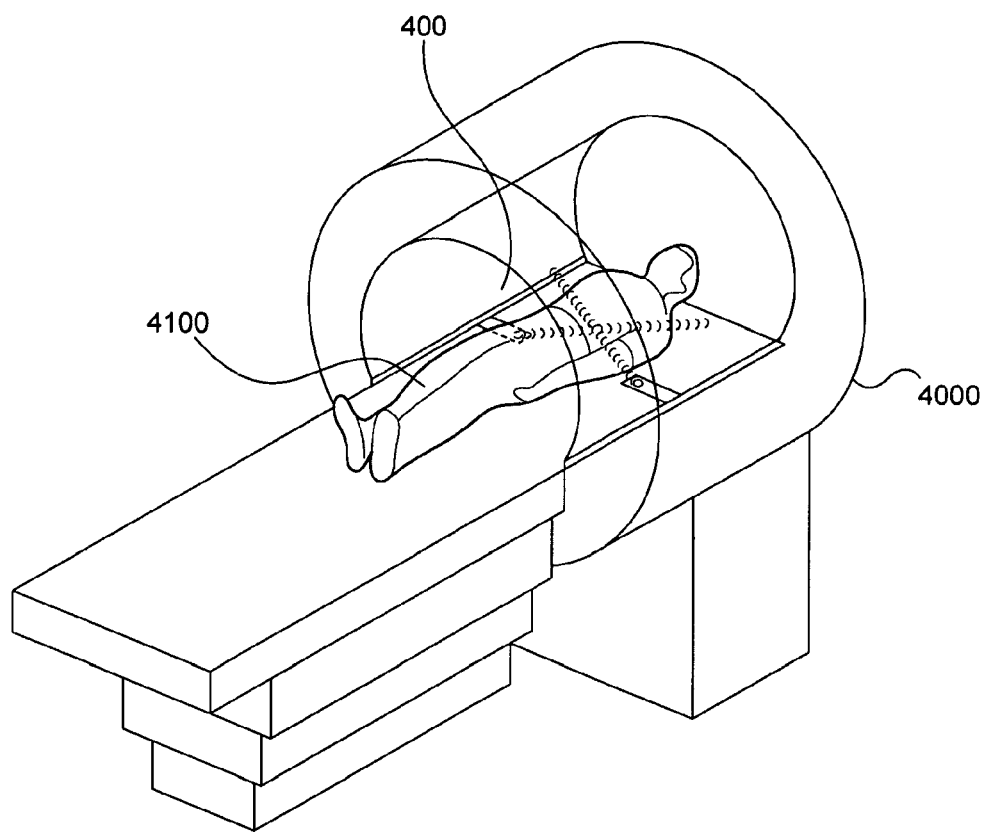
FIG. 7a depicts a patient in an imaging system receiving treating with focused energy waves.

FIG. 7a depicts at least partial ablation of the renal sympathetic nerves 4400 to the kidney using an imaging system such as an MRI machine or CT scanner 4000. The MRI/CT scan can be linked to a focused ultrasound (HIFU) machine to perform the ablations of the sympathetic nerves 4400 around the region of the renal artery 4500. The MRI/CT scan performs the imaging 4010 and transmits data (e.g. three dimensional representations of the regions of interest) to the ultrasound controller which then directs the ultrasound to target the region of interest with low intensity ultrasound (50-1000 mW/cm2) heat (>1000 mW/cm2), cavitation, or a combination of these modalities and/or including introduction of enhancing agents locally or systemically (sonodynamic therapy). Optionally, a doppler ultrasound or other 3D/4D ultrasound is performed and the data pushed to the MRI system to assist with localization of the pathology; alternatively, the ultrasound data are utilized to directly control the direction of the energy being used to target the physiologic processes and CT/MRI is not obtained. Using this imaging and ablation system from a position external to a patient, many regions of the kidney can be treated such as the internal calyces, the cortex, the medulla, the hilum and the region near to the aorta.

Further parameters which can be measured include temperature via thermal spectroscopy using MRI or ultrasound thermometry/elastography; thermal imaging is a well-known feature of MRI scanners; the data for thermal spectroscopy exists within the MRI scan and can be extrapolated from the recorded data in real time by comparing regions of interest before and after or during treatment. Temperature data overlaid on the MRI scan enables the operator of the machine to visualize the increase in temperature and therefore the location of the heating to insure that the correct region has indeed been ablated and that excessive energy is not applied to the region. Having temperature data also enables control of the ablation field as far as applying the correct temperature for ablation to the nerves. Furthermore, other spectroscopic parameters can be determined using the MRI scan such as oxygenation, blood flow, or other physiologic and functional parameters. In one embodiment, an alternating magnetic field is used to over-stimulate or inhibit an autonomic nerve (e.g. to or from the kidney).

Elastography is a technique in which the shear waves of the ultrasound beam and reflectance are detected. The tissue characteristics change as the tissue is heated and the tissue properties change. An approximate temperature can be assigned to the tissue based on elastography and the progress of the heating can be monitored.

MRI scanners 4000 generally consist of a magnet and an RF coil. The magnet might be an electromagnet or a permanent magnet. The coil is typically a copper coil which generates a radiofrequency field. Recently, permanent magnets have been utilized to create scanners which are able to be used in almost any setting, for example a private office setting. Office based MRI scanners enable imaging to be performed quickly in the convenience of a physicians offices as well as requiring less magnetic force (less than 0.5 Tesla) and as a consequence, less shielding. The lower tesla magnets also provides for special advantages as far as diversity of imaging and resolution of certain features. Importantly, the permanent magnet MRI scanners are open scanners and do not encapsulate the patient during the scan.

In one embodiment, a permanent magnet MRI is utilized to obtain an MRI image of the region of interest 4010. High intensity focused 4100 ultrasound is used to target the region of interest 4600 identified using the MRI.

Image 4010 is monitored by a health care professional to ensure that the region of interest is being treated and can stop the therapy if the region is not being treated. Alternatively, an imaging algorithm can be initiated in which the region of interest is identified and then subsequent images are compared to the initial demarcated region of interest.

Perhaps, most importantly, with MRI, the region around the renal arteries can be easily imaged as can any other region such as the eye, brain, prostate, breast, liver, colon, spleen, aorta, hip, knee, spine, venous tree, and pancreas. The imaging from the MRI can be utilized to precisely focus the ultrasound beam to the region of interest around the renal arteries or elsewhere in the body. With MRI, the actual nerves to be modified or modulated can be directly visualized and targeted with the energy delivered through the body from the ultrasound transducers. One disadvantage of MRI can be the frame acquisition (difficulty in tracking the target) rate as well as the cost of introducing an MRI machine into the treatment paradigm.

Figures 7B, 7C:
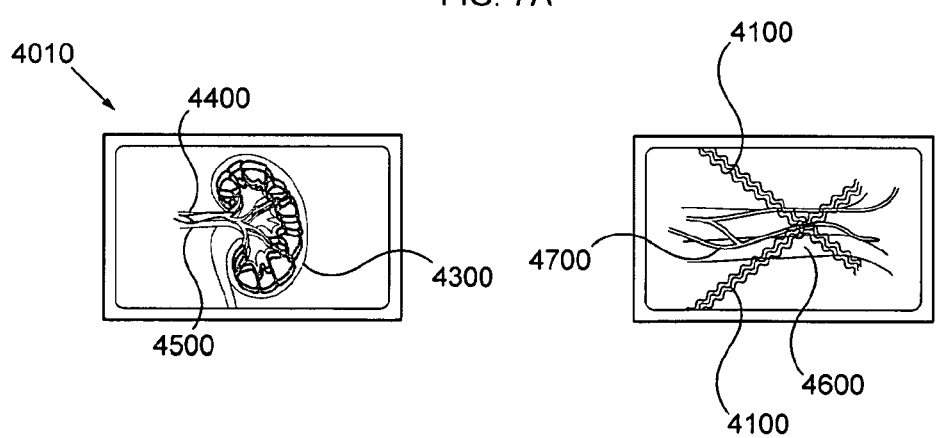
FIG. 7b depicts visualization of a kidney being treated.
FIG. 7c depicts a close up view of the renal nerve region of the kidney being treated.
Figure 7D:
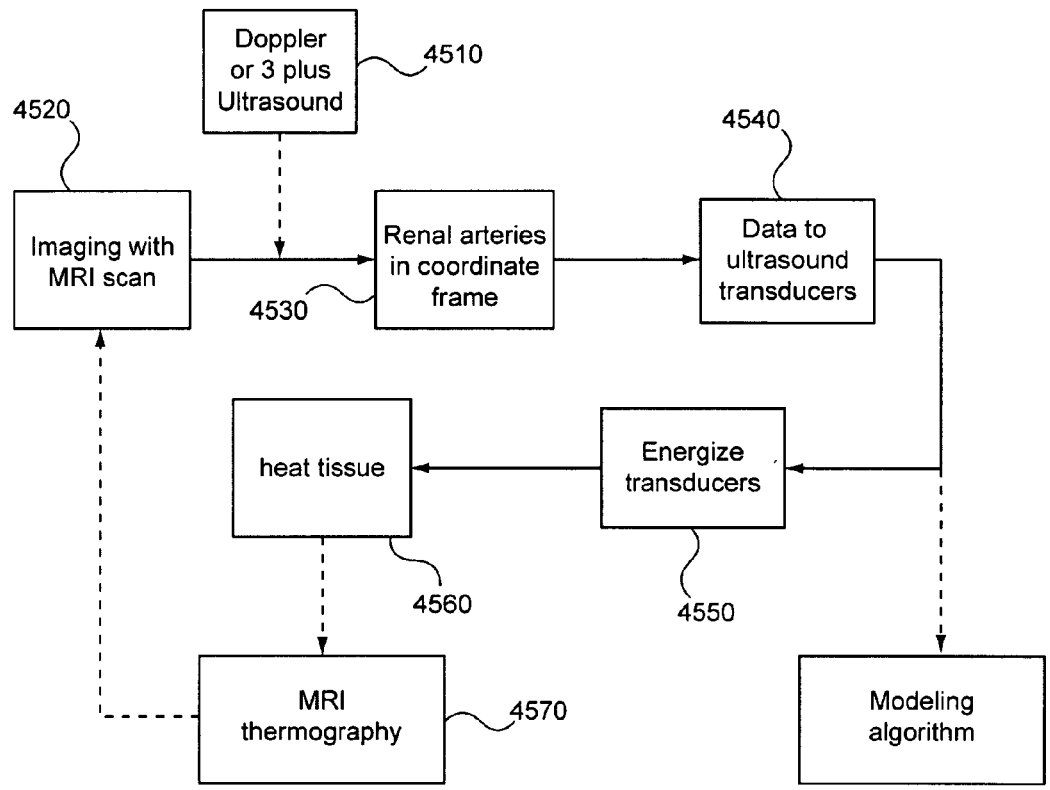
FIG. 7d depicts a method to treat the autonomic nervous system using MRI and energy transducers.

FIG. 7b depicts a method of treating a region with high intensity focused ultrasound (HIFU). Imaging with an MRI 4520 or Doppler ultrasound 4510 (or preferably both) is performed. MRI can be used to directly or indirectly (e.g. using functional MRI or spectroscopy) to visualize the sympathetic nerves. T1 weighted or T2 weighted images can be obtained using the MRI scanner. In addition to anatomic imaging, the MRI scanner can also obtain temperature data regarding the effectiveness of the ablation zone as well as the degree to which the zone is being heated and which parts of the zones are being heated. Other spectroscopic parameters can be added as well such as blood flow and even nerve activity. Ultrasound can be used to add blood flow to the images using Doppler imaging. The spectroscopic data can be augmented by imaging moieties such as particles, imaging agents, or particles coupled to imaging agents which are injected into the patient intravenously, or locally, and proximal to the region of the renal arteries; these imaging moieties may be visualized on MRI, ultrasound, or CT scan. Ultrasound can also be utilized to determine information regarding heating. The reflectance of the ultrasonic waves changes as the temperature of the tissue changes. By comparing the initial images with the subsequent images after heating, the temperature changes can be determined.

In one embodiment, the kidneys are detected by a cross-sectional imaging modality such as MRI, ultrasound, or CT scan. Next, the imaging data is placed into a three dimensional coordinate system which is linked to one or more ultrasound (e.g. HIFU) transducers which focus ultrasound onto the region of the renal arteries in the coordinate frame. The linking, or coupling, of the imaging to the therapeutic transducers is accomplished by determining the 3 dimensional position of the target by creating an anatomic model. The transducers are placed in a relative three dimensional coordinate frame as well. For example, the transducers can be placed in the imaging field during the MRI or CT scan such that the cross-sectional pictures include the transducers.

Alternatively, in another embodiment, ultrasound is utilized and the ultrasound image can be directly correlated to the origin of the imaging transducer. The therapeutic transducer in some embodiments is the same as the imaging transducer and therefore the therapeutic transducer is by definition coupled in a coordinate reference once the imaging transducer coordinates are known. If the therapeutic transducer and the imaging transducer are different devices, then they can be coupled by knowledge of the relative position of the two devices. The region of interest (ROI) is highlighted in a software algorithm . . . for example, the renal arteries, the calyces, the medullary region, the cortex, the renal hila, the celiac ganglia, the aorta, or any of the veins of the venous system as well. In another embodiment, the adrenal gland, the vessels traveling to the adrenal gland, or the autonomic nerves traveling to the adrenal gland are targeted with focused ultrasound and then either the medulla or the cortex of the adrenal gland or the nerves and arteries leading to the gland are partially or fully ablated with ultrasonic energy.

The targeting region or focus of the ultrasound is the point of maximal intensity. In some embodiments, targeting focus is placed in the center of the artery such that the walls on either side receive equivalent amounts of energy or power and can be heated more evenly than if one wall of the blood vessel is targeted. In some embodiments in which a blood vessel is targeted which has a closely surrounding vein (e.g. the renal artery/vein pedicle), the center of the focus might be placed at the boundary of the vein and the artery.

Once the transducers are energized after the region is targeted, the tissue is heated 4560 and a technique such as MRI thermography 4570 or ultrasound thermography is utilized to determine the tissue temperature. During the assessment of temperature, the anatomic data from the MRI scan or the Doppler ultrasound is then referenced to ensure the proper degree of positioning and the degree of energy transduction is again further assessed by the modeling algorithm 4545 to set the parameters for the energy transducers 4550. If there is movement of the target, the transducers may have to be turned off and the patient repositioned.

Ablation can also be augmented using agents such as magnetic nanoparticles or liposomal nanoparticles which are responsive to a radiofrequency field generated by a magnet. These particles can be selectively heated by the magnetic field. The particles can also be enhanced such that they will target specific organs and tissues using targeting moieties such as antibodies, peptides, etc. In addition to the delivery of heat, the particles can be activated to deliver drugs, bioactive agents, or imaging agents at the region at which action is desired (e.g. the renal artery). The particles can be introduced via an intravenous route, a subcutaneous route, or a percutaneous route.

The addition of Doppler ultrasound 4510 may be provided as well. The renal arteries are (if renal arteries or regions surrounding the arteries are the target) placed in a 3D coordinate reference frame 4530 using a software algorithm with or without the help of fiducial markers. Data is supplied to ultrasound transducers 4540 from a heat modeling algorithm 4545 and the transducers are energized with the appropriate phase and power to heat the region of the renal artery to between 40 degrees C. and 90 degrees C. within a time span of several minutes. The position within the 3D coordinate reference is also integrated into the treatment algorithm so that the ultrasound transducers can be moved into the appropriate position. The ultrasound transducers may have frequencies below 1 megahertz (MHz), from 1-20 MHz, or above 30 Mhz. The transducers may be in the form of a phased array, either linear or curved, or the transducers may be mechanically moved so as to focus ultrasound to the target of interest. In addition, MRI thermography 4570 can be utilized so as to obtain the actual temperature of the tissue being heated. These data can be further fed back to the system to slow down or speed up the process of ablation 4560 via the transducers 4550.

Aside from focused ultrasound, ultrasonic waves can be utilized directly to either heat an area or to activate pharmaceuticals in the region of interest. There are several methodologies to enhance drug delivery using focused ultrasound. For example, particles can release pharmaceutical when they are heated by the magnetic field. Liposomes can release a payload when they are activated with focused ultrasound. Ultrasound waves have a natural focusing ability if a transducer is placed in the vicinity of the target and the target contains an activateable moiety such as a bioactive drug or material (e.g. a nanoparticle sensitive to acoustic waves). Examples of sonodynamically activated moieties include some porphyrin derivatives.

So as to test the region of interest and the potential physiologic effect of ablation in that region, the region can be partially heated with the focused ultrasound to stun or partially ablate the nerves. Next, a physiologic test such as the testing of blood pressure or measuring norepinephrine levels in the blood can be performed to ensure that the correct region was indeed targeted for ablation. Depending on the parameter, additional treatments may be performed.

In another embodiment, a fiducial is utilized to demarcate the region of interest. A fiducial can be intrinsic (e.g. part of the anatomy) or the fiducial can be extrinsic (e.g. placed in position). For example, the fiducial can be an implanted fiducial, a fiducial or device placed in the blood vessels, or a device placed percutaneously through a catheterization or other procedure. The fiducial can also be a bone, such as a rib, or another internal organ, for example, the liver. In one embodiment, the fiducial is a beacon or balloon or balloon with a beacon which is detectable via ultrasound. In one embodiment, the blood flow in the renal arteries, detected via Doppler or B-mode imaging, is the fiducial and its relative direction is determined via Doppler analysis. Next, the renal arteries, and specifically, the region around the renal arteries are placed into a three dimensional coordinate frame utilizing the internal fiducials. A variant of global positioning system technology can be utilized to track the fiducials within the artery or around the arteries. The three dimensional coordinate frame is transmitted to the therapeutic ultrasound transducers and then the transducers and anatomy are coupled to the same coordinate frame. At this point, the HIFU is delivered from the transducers, calculating the position of the transducers based on the position of the target in the reference frame.

In one embodiment, a virtual fiducial is created via an imaging system. For example, in the case of a blood vessel such as the renal artery, an image of the blood vessel using B-mode ultrasound can be obtained which correlates to the blood vessel being viewed in direct cross section (1700; FIG. 17C). When the vessel is viewed in this type of view, the center of the vessel can be aligned with, the center of an ultrasound array (e.g. HIFU array 1600) and the transducers can be focused and applied to the vessel, applying heat to regions around the vessels 1680. With different positions of the transducers 1610 along a circumference or hemisphere 1650, varying focal points can be created 1620, 1630, 1640. The directionality of the transducers allows for a lesion which runs lengthwise along the vessel 1620, 1630, 1640. Thus, a longitudinal lesion can be produced along the artery to insure maximal inhibition of nerve function. In some embodiments, the center of the therapeutic ultrasound transducer is off center relative to the center of the vessel so that the energy is applied across the vessel wall at an angle.

In this method of treatment, an artery such as a renal artery is viewed in cross-section or close to a cross-section under ultrasound guidance. In this position, the blood vessel is substantially parallel to the axis of the spherical transducer so as to facilitate lesion production. The setup of the ultrasound transducers 1600 has previously been calibrated to create multiple focal lesions 1620, 1630, 1640 along the artery if the artery is in cross-section 1680.

In one embodiment, the fiducial is an intravascular fiducial such as a balloon or a hermetically sealed transmitting device. The balloon is detectable via radiotransmitter within the balloon which is detectable by the external therapeutic transducers. The balloon can have three transducers, each capable of relaying their position so that the balloon can be placed in a three dimensional coordinate reference. Once the balloon is placed into the same coordinate frame as the external transducers using the transmitting beacon, the energy transducing devices can deliver energy (e.g. focused ultrasound) to the blood vessel (e.g. the renal arteries) or the region surrounding the blood vessels (e.g. the renal nerves). The balloon and transmitters also enable the ability to definitively track the vasculature in the case of movement (e.g. the renal arteries). In another embodiment, the balloon measures temperature or is a conduit for coolant applied during the heating of the artery or nerves.

Delivery of therapeutic ultrasound energy to the tissue inside the body is accomplished via the ultrasound transducers which are directed to deliver the energy to the target in the coordinate frame.

Once the target is placed in the coordinate frame and the energy delivery is begun, it is important to maintain targeting of the position, particularly when the target is a small region such as the sympathetic nerves. To this end, the position of the region of ablation is compared to its baseline position, both in a three dimensional coordinate reference frame. The ongoing positional monitoring and information is fed into an algorithm which determines the new targeting direction of the energy waves toward the target. In one embodiment, if the position is too far from the original position (e.g. the patient moves), then the energy delivery is stopped and the patient repositioned. If the position is not too far from the original position, then the energy transducers can be repositioned either mechanically (e.g. through physical movement) or electrically via phased array (e.g. by changing the relative phase of the waves emanating from the transducers). In another embodiment, multiple transducers are placed on the patient in different positions and each is turned on or off to result in the necessary energy delivery. With a multitude of transducers placed on the patient, a greater territory can be covered with the therapeutic ultrasound. The therapeutic positions can also serve as imaging positions for intrinsic and/or extrinsic fiducials.

In addition to heat delivery, ultrasound can be utilized to deliver cavitating energy which may enable drug delivery at certain frequencies. Cavitating energy can also lead to ablation of tissue at the area of the focus. A systemic dose of a drug can be delivered to the region of interest and the region targeted with the cavitating or other forms of ultrasonic energy. Other types of therapeutic delivery modalities include ultrasound sensitive bubbles or radiation sensitive nanoparticles, all of which enhance the effect of the energy at the target of interest.

Ultrasound may also be utilized to create tumor vaccines in vivo. In this embodiment, sub-ablative doses of energy is applied to a tumor to induce a stress response or to heat shock response to increase the anti-tumor or immune response to the tumor. The energy can be applied from an external position to and internal position or from an internal position to an external position.

Figure 8A:
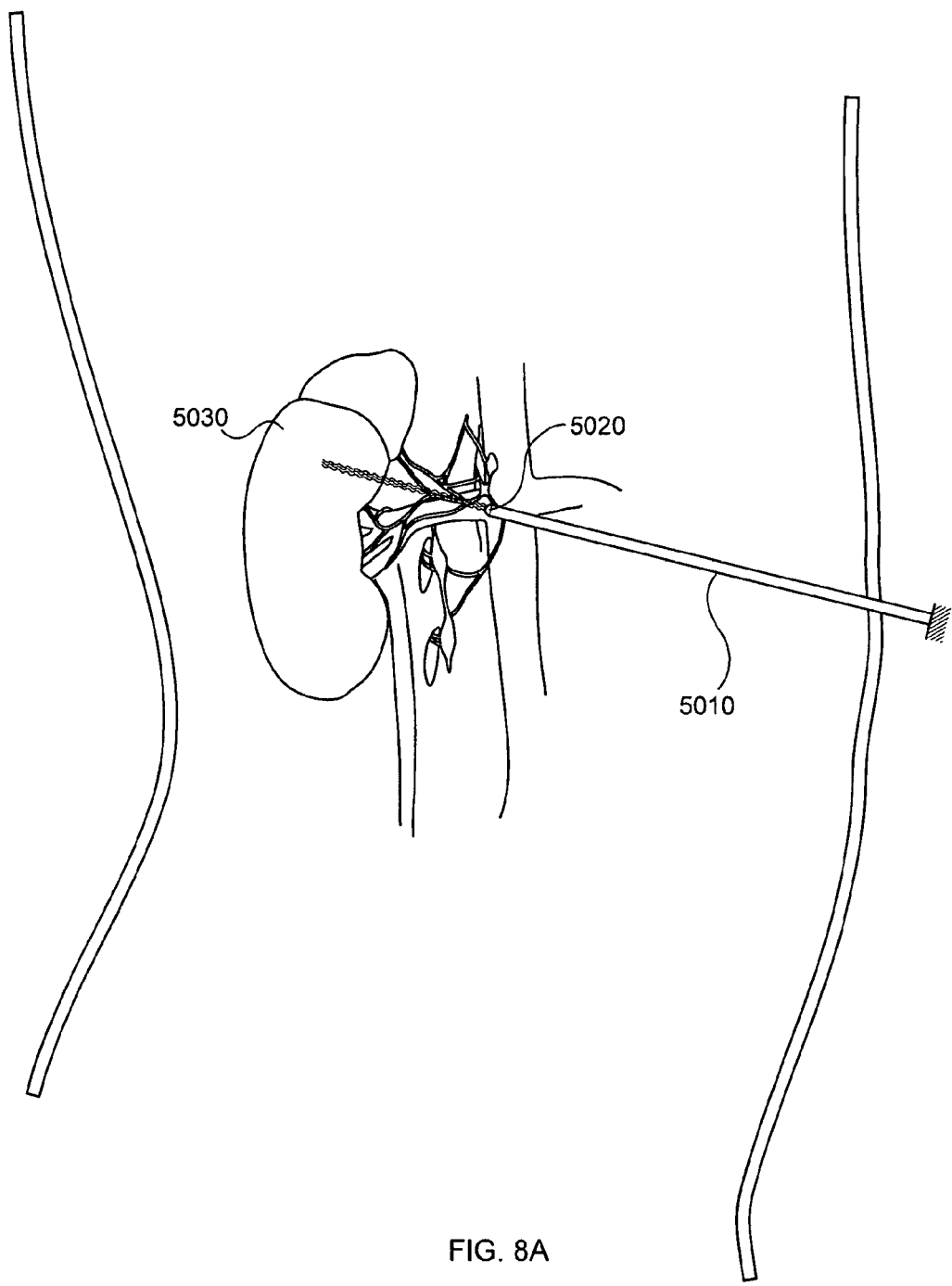
FIG. 8a depicts a percutaneous approach to treating the autonomic nervous system surrounding the kidneys.

FIG. 8a depicts a percutaneous procedure 5000 and device 5010 in which the region around the renal artery 5030 is directly approached through the skin from an external position. A combination of imaging and ablation may be performed to ablate the region around the renal artery to treat hypertension, end stage renal disease, and heart failure. Probe 5010 is positioned through the skin and in proximity to the kidney 5030. The probe may include sensors which detect heat or temperature or may enable augmentation of the therapeutic energy delivery. Ablative, ionizing energy, heat, or light may be applied to the region to inhibit the sympathetic nerves around the renal artery using the probe 510. Ultrasound, radiofrequency, microwave, direct heating elements, and balloons with heat or energy sources may be applied to the region of the sympathetic nerves.

In one embodiment, the percutaneous procedure is performed under MRI, CT, or ultrasound guidance to obtain localization or information about the degree of heat being applied. In one embodiment, ultrasound is applied but at a sub-ablative dose. That is, the energy level is enough to damage or inhibit the nerves but the temperature is such that the nerves are not ablated but paralyzed or partially inhibited by the energy. A particularly preferred embodiment would be to perform the procedure under guidance from an MRI scanner because the region being heated can be determined anatomically in real time as well via temperature maps. As described above the images after heating can be compared to those at baseline and the signals are compared at the different temperatures.

In one embodiment, selective regions of the kidney are ablated through the percutaneous access route; for example, regions which secrete hormones which are detrimental to a patient or to the kidneys or other organs. Using energy applied external to the patient through the skin and from different angles affords the ability to target any region in or on the kidney or along the renal nerves or at the region of the adrenal gland, aorta, or sympathetic chain. This greater breadth in the number of regions to be targeted is enabled by the combination of external imaging and external delivery of the energy from a multitude of angles through the skin of the patient to the target. The renal nerves can be targeted at their takeoff from the aorta onto the renal artery, at their synapses at the celiac ganglia, or at their bifurcation point along the renal artery.

In a further embodiment, probe 5010 can be utilized to detect temperature or motion of the region while the ultrasound transducers are applying the energy to the region. A motion sensor, position beacon, or accelerometer can be used to provide feedback for the HIFU transducers. In addition, an optional temperature or imaging modality may be placed on the probe 5010. The probe 5010 can also be used to locate the position within the laparoscopic field for the ablations to be performed.

Figure 8B:
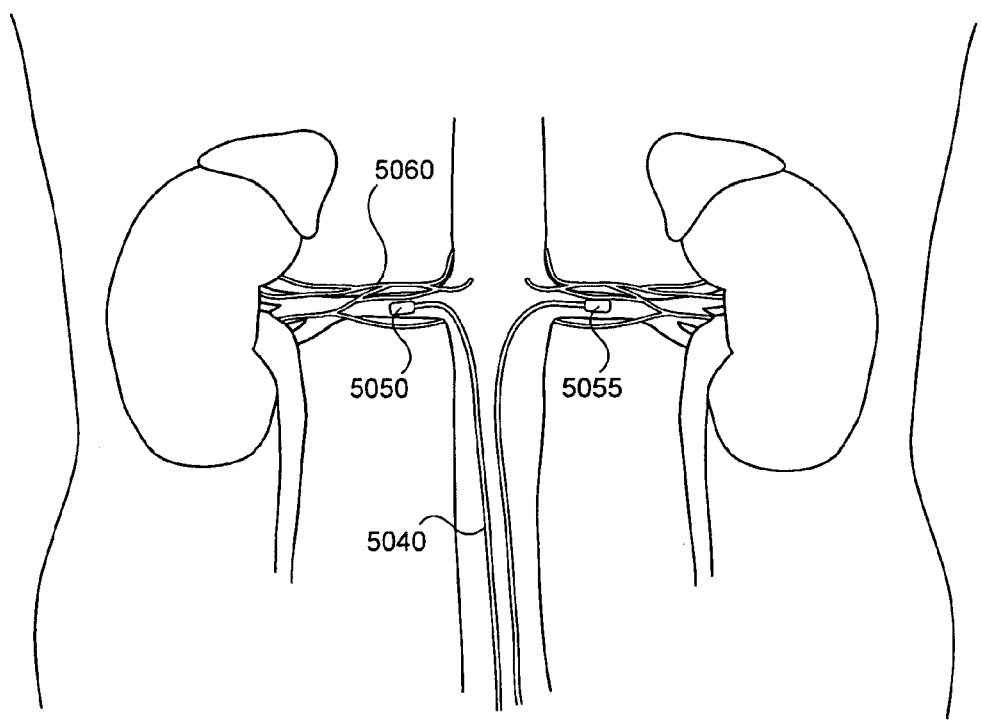
FIG. 8b depicts an intravascular approach to treating the autonomic nervous system.

In FIG. 8b, intravascular devices 5050, 5055 are depicted which apply energy to the region around the renal arteries 5065. The intravascular devices can be utilized to apply radiofrequency, ionizing radiation, and/or ultrasound (either focused or unfocused) energy to the renal artery and surrounding regions. MRI or ultrasound or direct thermometry can be further utilized to detect the region where the heat is being applied while the intravascular catheter is in place.

In one embodiment, devices 5050, 5055 apply ultrasound energy which inhibits nerve function not by heating, but by mechanisms such as periodic pressure changes, radiation pressure, streaming or flow in viscous media, and pressures associated with cavitation, defined as the formation of holes in liquid media. Heat can selectively be added to these energies but not to create a temperature which ablates the nerves, only facilitates the mechanism of vibration and pressure. In this embodiment, the ultrasound is not focused but radiates outward from the source to essentially create a cylinder of ultrasonic waves that intersect with the wall of the blood vessel. An interfacial material between the ultrasound transducer and the wall of the artery may be provided such that the ultrasound is efficiently transduced through the arterial wall to the region of the nerves around the artery. In another embodiment, the ultrasound directly enters the blood and propagates through the ultrasound wall to affect the nerves. In some embodiments, cooling is provided around the ultrasound catheter which protects the inside of the vessel yet allows the ultrasound to penetrate through the wall to the regions outside the artery. A stabilization method for the ultrasound probe is also included in such a procedure. The stabilization method might include a stabilizing component added to the probe and may include a range finding element component of the ultrasound. Imaging can be performed externally or internally in this embodiment in which a catheter is placed inside the renal arteries.

Alternatively, in another embodiment, the devices 5050, 5055 can be utilized to direct externally applied energy (e.g. ultrasound) to the correct place around the artery as the HIFU transducers deliver the energy to the region. For example, the intravascular probe 5050 can be utilized as a homing beacon for the imaging technology utilized for the externally delivered HIFU.

Figure 9A:
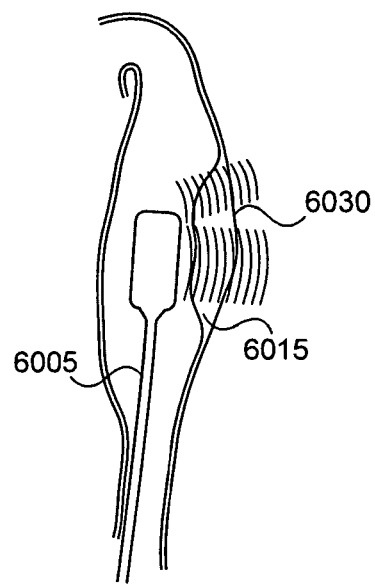
FIGS. 9a-9c depict the application of energy from inside the aorta to regions outside the aorta.

In another embodiment, the physiologic process of arterial expansion is targeted. In FIG. 9a, an ultrasound transducer is 6005 is placed near the wall of an aneurysm 6030. Ultrasonic energy is applied to the wall 6030 of the aneurysm to thicken the wall and prevent further expansion of the aneurysm. In some embodiments, clot within the aneurysm is targeted as well so that the clot is broken up or dissolved with the ultrasonic energy. Once the wall of the aneurysm is heated with ultrasonic energy to a temperature of between 40 and 70 degrees, the collagen, elastin, and other extracellular matrix in the wall will harden as it cools, thereby preventing the wall from further expansion. In another embodiment, a material is placed in the aneurysm sac and the focused or non-focused ultrasound utilized to harden or otherwise induce the material in the sac to stick to the aorta or clot in the aneurysm and thus close the aneurysm permanently. In one embodiment therefore, an ultrasound catheter is placed in an aorta at the region of an aneurysm wall or close to a material in an aneurysmal wall. The material can be a man-made material placed by an operator or it can be material such as thrombus which is in the aneurysm naturally. Ultrasound is applied to the wall, or the material, resulting in hardening of the wall or of the material, strengthening the aneurysm wall and preventing expansion.

Figure 9B:
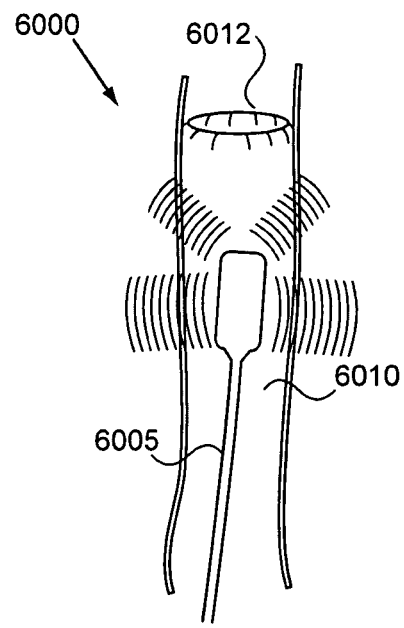

FIG. 9b depicts a clot prevention device 6012 within a blood vessel such as the aorta or vena cava 6000. The ultrasound catheter 6005 is applied to the clot prevention device (filter) 6012 so as to remove the clot from the device or to free the device 6012 from the wall of the blood vessel in order to remove it from the blood vessel 6000.

Figure 9C:
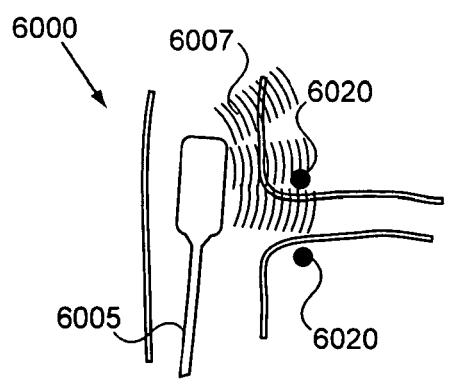

FIG. 9c depicts a device and method in which the celiac plexus 6020 close to the aorta 6000 is ablated or partially heated using heat or vibrational energy from an ultrasonic energy source 6005 which can apply focused or unfocused sound waves 6007 at frequencies ranging from 20 kilohertz to 5 Mhz and at powers ranging from 1 mW to over 100 kW in a focused or unfocused manner. Full, or partial ablation of the celiac plexus 6020 can result in a decrease in blood pressure via a similar mechanism as applying ultrasonic energy to the renal nerves; the ablation catheter is a focused ultrasound catheter but can also be a direct (unfocused) ultrasonic, a microwave transducer, or a resistive heating element.

Figure 10:
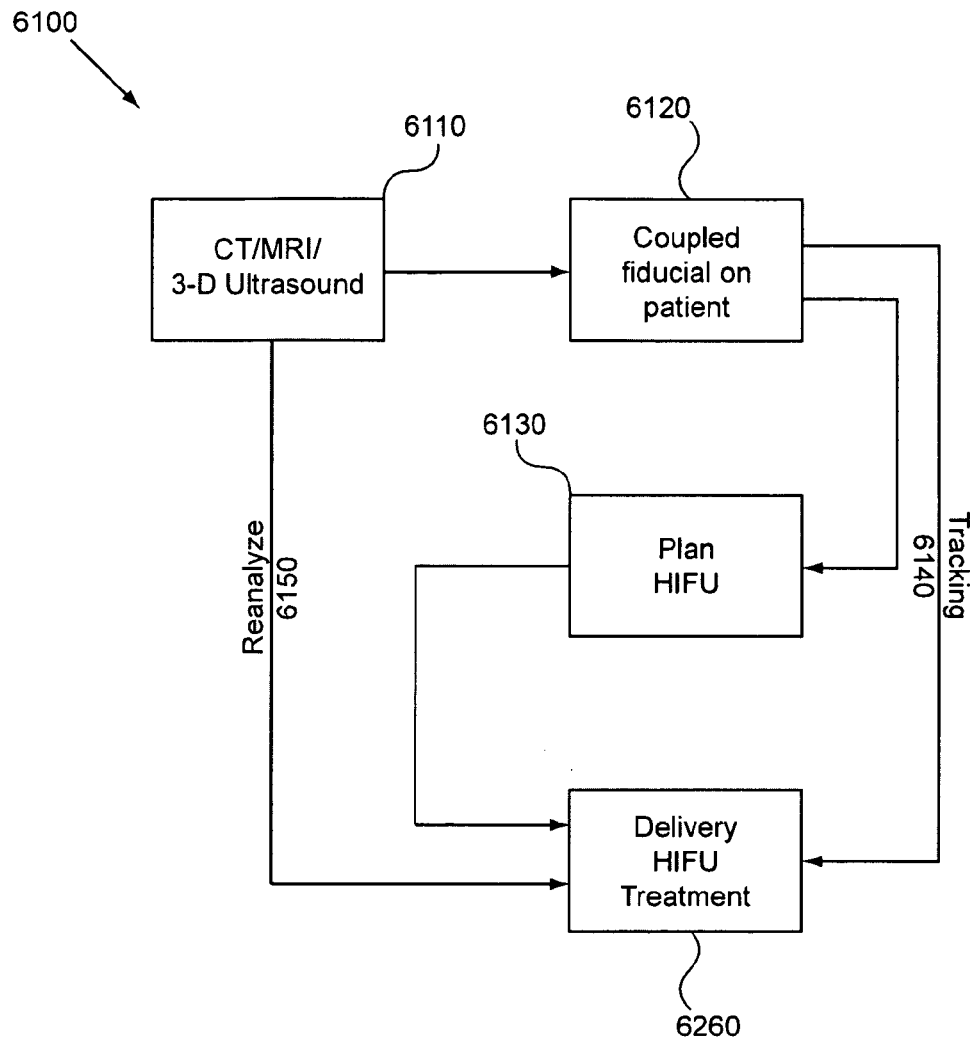
FIG. 10 depicts steps to treat a disease using HIFU.

FIG. 10 depicts a method 6100 to treat a patient with high intensity or low intensity focused ultrasound (HIFU or LIFU) 6230. In a first step, a CT and/or MRI scan and/or thermography and/or ultrasound (1D, 2D, 3D) is performed 6110. A fiducial or other marking on or in the patient 6120 is optionally used to mark and track 6140 the patient. The fiducial can be an implanted fiducial, a temporary fiducial, or a fiducial intrinsic to the patient (e.g. bone, blood vessel, arterial wall) which can be imaged using the CT/MRI/Ultrasound devices 6110. The fiducial can further be a temporary fiducial such as a catheter temporarily placed in an artery or vein of a patient or a percutaneously placed catheter. A planning step 6130 for the HIFU treatment is performed in which baseline readings such as position of the organ and temperature are determined; a HIFU treatment is then planned using a model (e.g. finite element model) to predict heat transfer, or pressure to heat transfer, from the ultrasound transducers 6130. The planning step incorporates the information on the location of the tissue or target from the imaging devices 6110 and allows placement of the anatomy into a three dimensional coordinate reference such that modeling 6130 can be performed.

The planning step 6130 includes determination of the positioning of the ultrasound transducers as far as position of the focus in the patient. X, Y, Z, and up to three angular coordinates are used to determine the position of the ultrasonic focus in the patient based on the cross sectional imaging 6110. The HIFU transducers might have their own position sensors built in so that the position relative to the target can be assessed. Alternatively, the HIFU transducers can be rigidly fixed to the table on which the patient rests so that the coordinates relative to the table and the patient are easily obtainable. The flow of heat is also modeled in the planning step 6130 so that the temperature at a specific position with the ultrasound can be planned and predicted. For example, the pressure wave from the transducer is modeled as it penetrates through the tissue to the target. For the most part, the tissue can be treated as water with a minimal loss due to interfaces. The relative power and phase of the ultrasonic wave at the target can be determined by the positional coupling between the probe and target. A convective heat transfer term is added to model heat transfer due to blood flow, particularly in the region of an artery. A conductive heat transfer term is also modeled in the equation for heat flow and temperature.

Another variable which is considered in the planning step is the size of the lesion and the error in its position. In the ablation of small regions such as nerves surrounding blood vessels, the temperature of the regions may need to be increased to a temperature of 60-90 degrees Celsius to permanently ablate nerves in the region. Temperatures of 40-60 degrees may temporarily inhibit or block the nerves in these regions and these temperatures can be used to determine that a patient will respond to a specific treatment without permanently ablating the nerve region. Subsequently, additional therapy can be applied at a later time so as to complete the job or perhaps, re-inhibit the nerve regions.

An error analysis is also performed during the treatment contemplated in FIG. 10. Each element of temperature and position contains an error variable which propagates through the equation of the treatment. The errors are modeled to obtain a virtual representation of the temperature mapped to position. This map is correlated to the position of the ultrasound transducers in the treatment of the region of interest.

During the delivery of the treatment 6260, the patient may move, in which case the fiducials 6120 track the movement and the position of the treatment zone is re-analyzed 6150 and the treatment is restarted or the transducers are moved either mechanically or electrically to a new focus position.

In another embodiment, a cross-sectional technique of imaging is used in combination with a modality such as ultrasound to create a fusion type of image. The cross-sectional imaging is utilized to create a three dimensional data set of the anatomy. The ultrasound, providing two dimensional images, is linked to the three dimensional imaging provided by the cross-sectional machine through fiducial matches between the ultrasound and the MRI. As a body portion moves within the ultrasound field, the corresponding data is determined (coupled to) the cross-sectional (e.g. MRI image) and a viewing station can show the movement in the three dimensional dataset. The ultrasound provides real time images and the coupling to the MRI or other cross-sectional image depicts the ultrasound determined position in the three dimensional space.

Figure 11A:
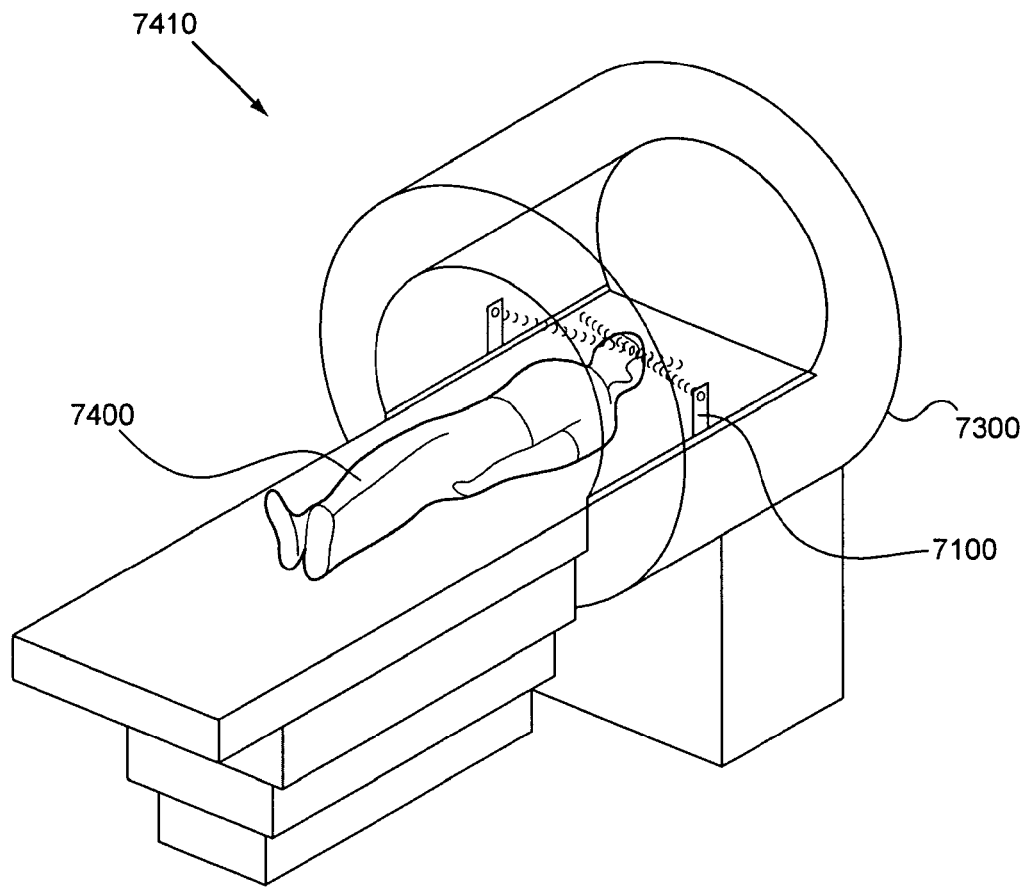
FIG. 11a depicts treatment of brain lesions using cross sectional imaging.
Figure 11B:
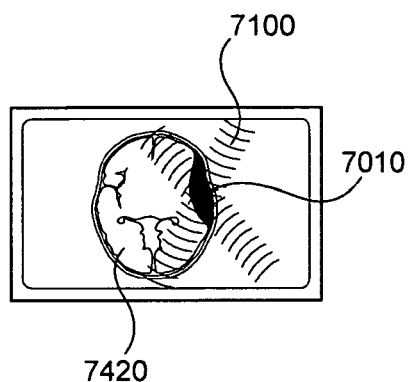
FIG. 11b depicts an image on a viewer showing therapy of the region of the brain being treated.
Figure 11C:
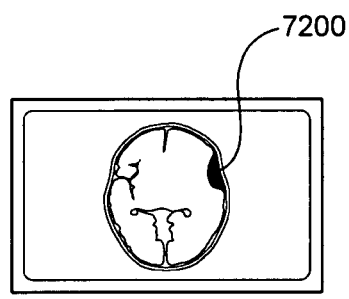
FIG. 11c depicts another view of a brain lesion.

FIG. 11 depicts the treatment of another disease in the body of a patient, this time in the head of a patient. Subdural and epidural hematomas occur as a result of bleeding of blood vessels in the dural or epidural spaces of the brain, spinal column, and scalp. FIG. 11 depicts a CT or MRI scanner 7300 and a patient 7400 therein. An image is obtained of the brain 7000 using a CT or MRI scan. The image is utilized to couple the treatment zone 7100 to the ultrasound array utilized to heat the region. In one embodiment 7100, a subdural hematoma, either acute or chronic, is treated. In another embodiment 7200, an epidural hematoma is treated. In both embodiments, the region of leaking capillaries and blood vessels are heated to stop the bleeding, or in the case of a chronic subdural hematoma, the oozing of the inflammatory capillaries.

In an exemplary embodiment of modulating physiologic processes, a patient 7400 with a subdural or epidural hematoma is chosen for treatment and a CT scan or MRI 7300 is obtained of the treatment region. Treatment planning ensues and the chronic region of the epidural 7200 or subdural 7010 hematoma is targeted for treatment with the focused ultrasound 7100 transducer technology. Next the target of interest is placed in a coordinate reference frame as are the ultrasound transducers. Therapy 7100 ensues once the two are couple together. The focused ultrasound heats the region of the hematoma to dissolve the clot and/or stop the leakage from the capillaries which lead to the accumulation of fluid around the brain 7420. The technology can be used in place of or in addition to a burr hole, which is a hole placed through the scalp to evacuate the fluid.

Figure 12:
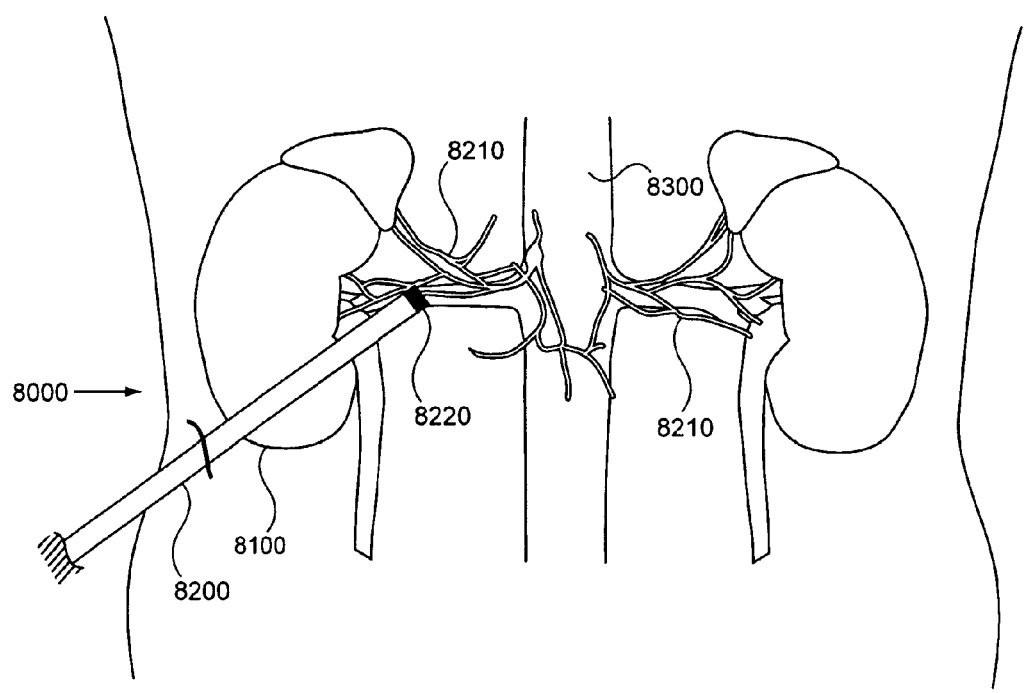
FIG. 12 depicts treatment of the renal nerve region using a laparoscopic approach.

FIG. 12 depicts a laparoscopic based approach 8000 to the renal artery region in which the sympathetic nerves 8210 can be ligated, interrupted, or otherwise modulated. In laparoscopy, the abdomen of a patient is insufflated and laparoscopic instruments introduced into the insufflated abdomen. The retroperitoneum is accessible through a flank approach or through a transabdominal approach. A laparoscopic instrument 8200 with a distal tip 8220 can apply heat or another form of energy or deliver a drug to the region of the sympathetic nerves 8210. The laparoscopic implement can also be utilized to ablate or alter the region of the celiac plexus 8300 and surrounding ganglia. The laparoscope can have an ultrasound transducer attached, a temperature probe attached, a microwave transducer attached, or a radiofrequency transducer attached. The laparoscope can be utilized to directly ablate or stun the nerves (e.g. with a lower frequency/energy) surrounding vessels or can be used to ablate or stun nerve ganglia which travel with the blood vessels. Similar types of modeling and imaging can be utilized with the percutaneous approach as with the external approach to the renal nerves.

Figure 13:
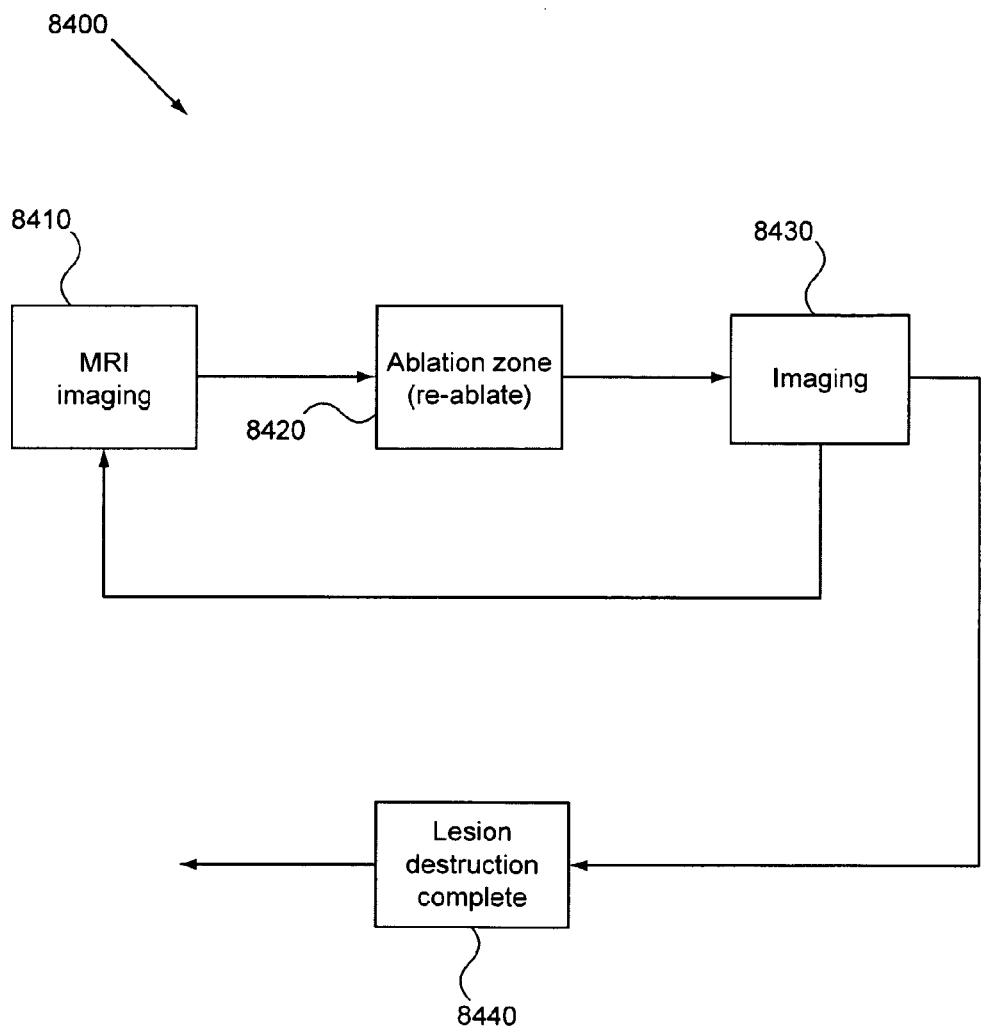
FIG. 13 depicts a methodology for destroying a region of tissue using imaging markers.

FIG. 13 depicts an algorithm for the treatment of a region of interest. MRI and/or CT with or without a imaging agent 8410 can be utilized to demarcate the region of interest (for example, the ablation zone) and then ablation 8420 can be performed around the zone identified by the agent using any of the modalities above. This algorithm is applicable to any of the therapeutic modalities described above including external HIFU, laparoscopic instruments, intravascular catheters, percutaneous catheters, as well as any of the treatment regions including the renal nerves, the eye, the kidneys, the aorta, or any of the other nerves surrounding peripheral arteries or veins. Imaging 8430 with CT, MRI, ultrasound, or PET can be utilized in real time. At such time when destruction of the lesion is complete 8440, imaging with an imaging (for example, a molecular imaging agent or a contrast agent such as gadolinium) agent 8410 can be performed again. The extent of ablation can also be monitored by monitoring the temperature or the appearance of the ablated zone under an imaging modality. Once lesion destruction is complete 8440, the procedure is finished. In some embodiments, ultrasonic diagnostic techniques such as elastography are utilized to determine the progress toward heating or ablation of a region.

Figure 14:
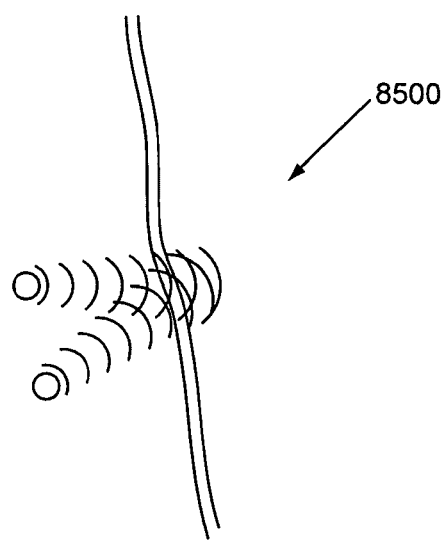
FIG. 14 depicts the partial treatment of a nerve bundle using converging imaging waves.

FIG. 14 depicts ablation in which specific nerve fibers of a nerve are targeted using different temperature gradients or temperatures 8500. For example, if temperature is determined by MRI thermometry or with another technique such as ultrasound, then the temperature can be kept at a temperature in which only certain nerve fibers are targeted for destruction or inhibition. Alternatively, part or all of the nerve can be turned off temporarily to then test the downstream effect of the nerve being turned off. For example, the sympathetic nerves around the renal artery can be turned off with a small amount of heat or other energy (e.g. vibrational energy) and then the effect can be determined. For example, norepinephrine levels in the systemic blood or renal vein can be assayed; alternatively, the stimulation effect of the nerves can be tested after temporary cessation of activity (e.g. skin reactivity, blood pressure lability, cardiac activity, pulmonary activity. Varying frequencies of vibration can be utilized to inhibit specific nerve fibers versus others. For example, in some embodiments, the efferent nerve fibers are inhibited and in other embodiments, the afferent nerve fibers are inhibited. In some embodiments, both types of nerve fibers are inhibited, temporarily or permanently.

Figure 15:
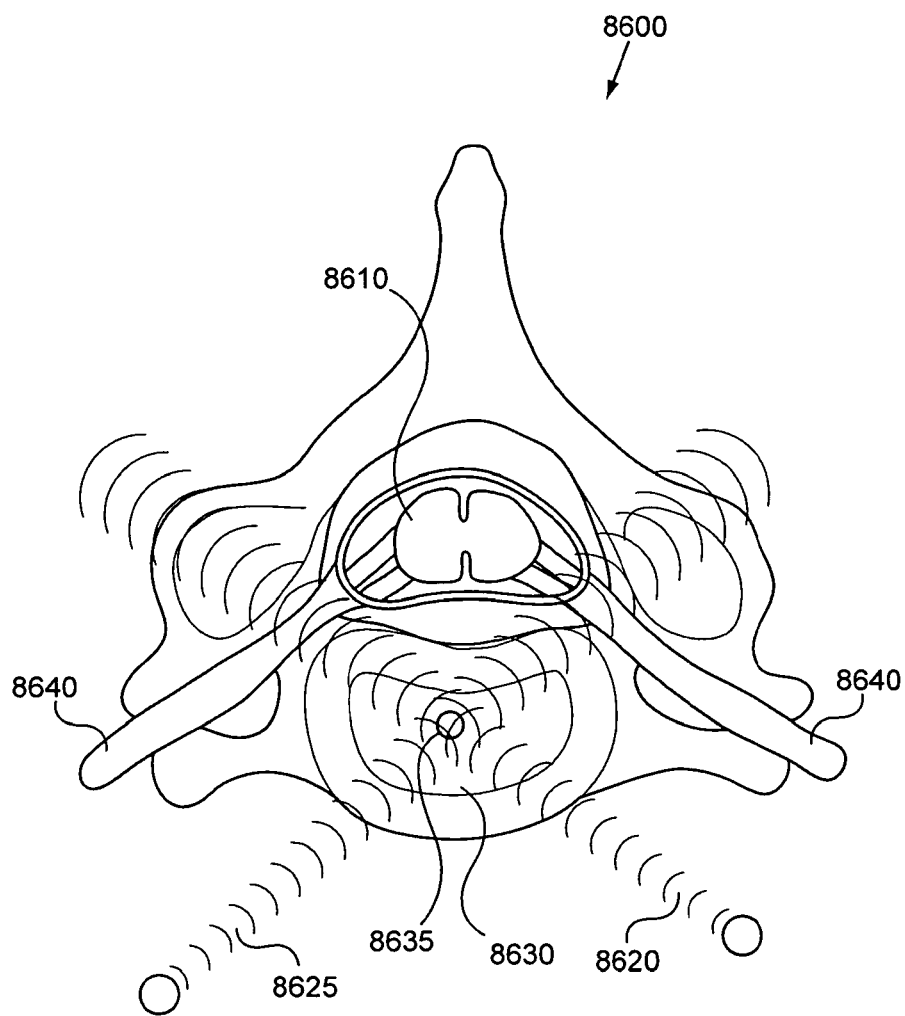
FIG. 15 depicts the application of focused energy to the vertebral column.

FIG. 15 depicts treatment 8600 of a vertebral body or intervertebral disk 8610 in which nerves within 8640 or around the vertebral column 8630 are targeted with ultrasound 8625 waves. In one embodiment, nerves around the facet joints are targeted. In another embodiment, nerves leading to the disks or vertebral endplates are targeted.

Figure 16:
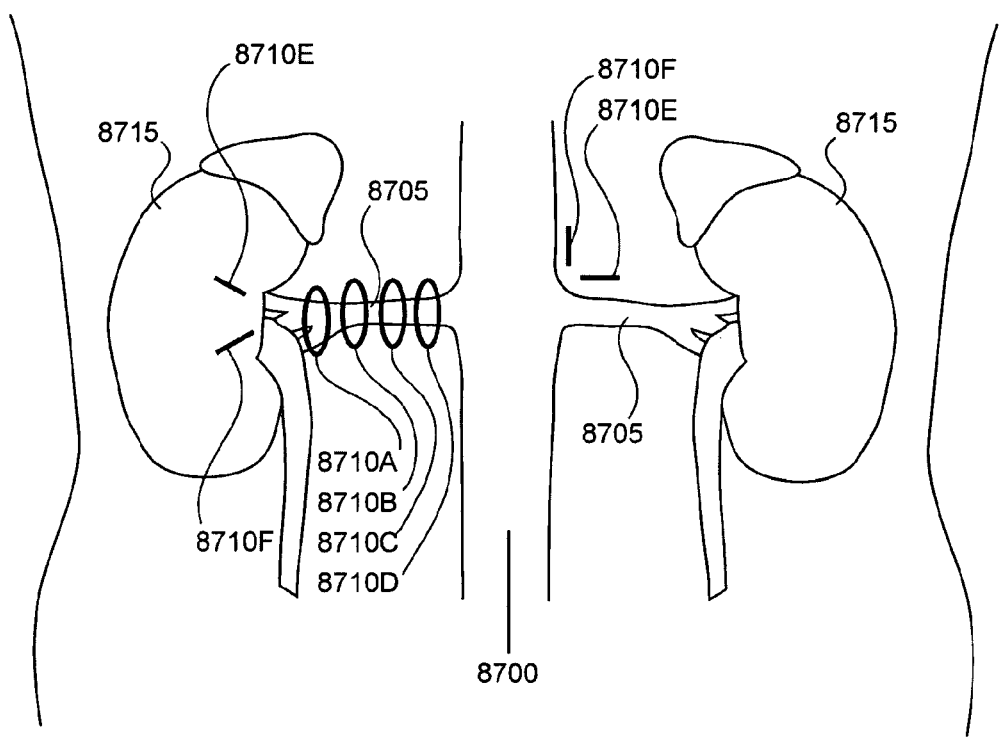
FIG. 16 depicts the types of lesions which are created around the renal arteries to affect a response.

FIG. 16 depicts a set of lesion types, sizes, and anatomies 8710*a-h* which lead to de-innervation of the different portions of the sympathetic nerve tree. For example, the lesions can be annular, cigar shaped, linear, doughnut and/or spherical; the lesions can be placed around the renal arteries 8705, inside the kidney 8710, and/or around the aorta 8700. For example, the renal arterial tree 8700 comprises renal arteries 8705 and kidneys 8715. Lesions 8710*a-h* are different types of lesions which are created around the aorta 8700 and vascular tree. Lesions can be placed in a spiral shape along the length of the artery.

Figure 17A:
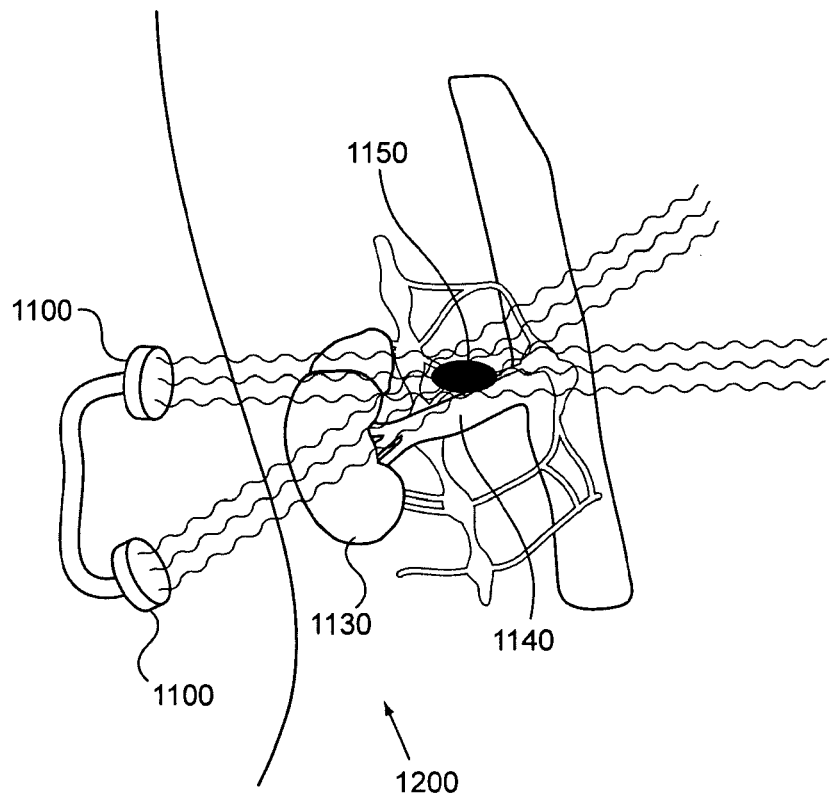
FIG. 17a depicts the application of multiple transducers to treat regions of the autonomic nervous system.
Figures 17B, 17C:
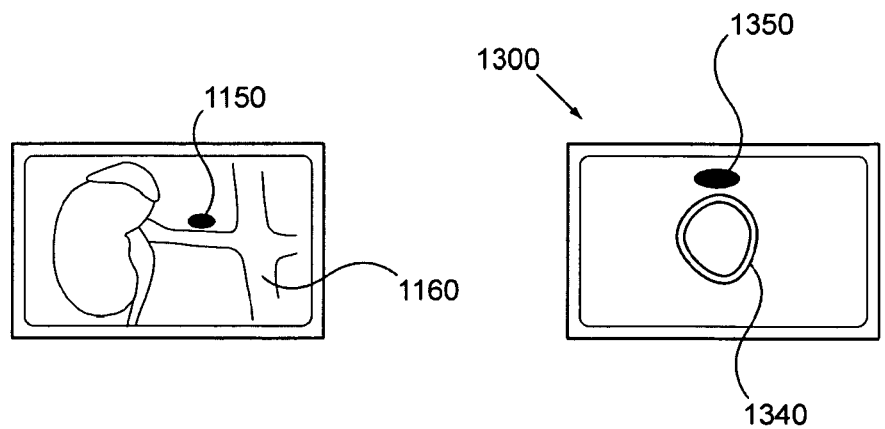
FIGS. 17b-17c depict methods and devices to treat a specific region surrounding an artery.
Figure 17D:
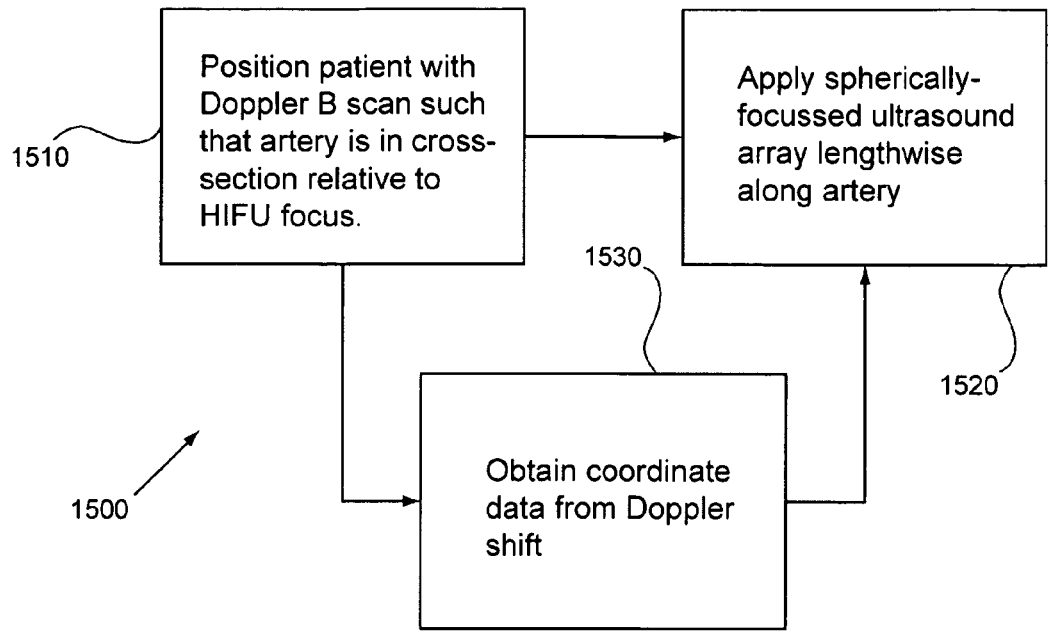
FIG. 17d depicts a method for localizing HIFU transducers relative to Doppler ultrasound signals.
Figure 17E:
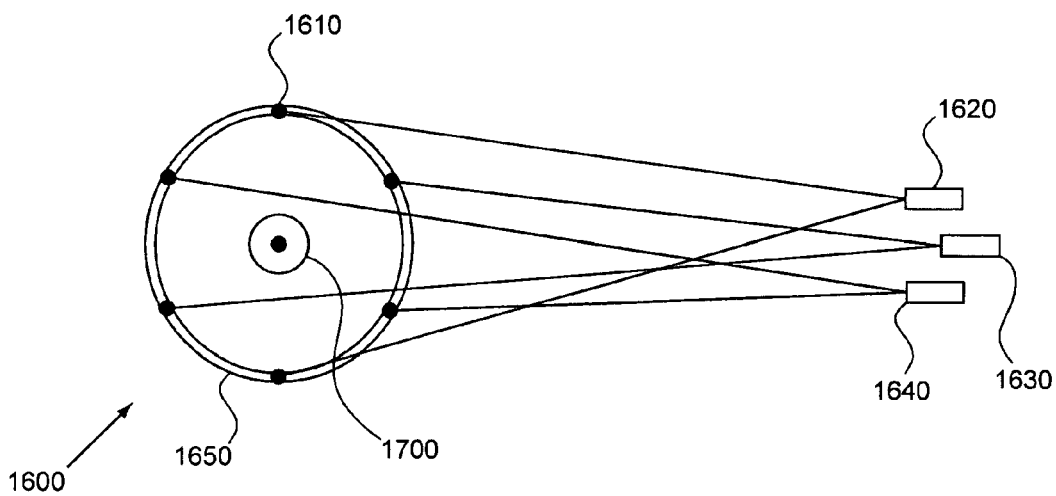
FIG. 17e depicts an arrangement of transducers relative to a target
Figure 17F:
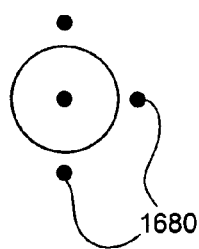
FIG. 17f depicts ablation zones in a multi-focal region in cross-section.

FIG. 17*a* depicts a multi-transducer HIFU device 1100 which applies a finite lesion 1150 along an artery 1140 (e.g. a renal artery) leading to a kidney 1130. The lesion can be spherical in shape, cigar shaped 1050, annular shaped 1050, or point shaped; however, in a preferred embodiment, the lesion runs along the length of the artery and has a cigar shaped. This lesion is generated by a spherical type of ultrasound array in a preferred embodiment. FIG. 17*c* depicts the pathway of the spherical or cylindrical type of ultrasound array 1600. Ultrasound transducers 1610 are aligned along the edge of a cylinder aimed so that they intersect at one or more focal spots 1620, 1630, 1640. The transducers 1610 are positioned along the cylinder 1650 such that some are closer to one focus or the other so that a range of distances to the artery is created. The patient and artery are positioned such that their centers 1700 co-localize with the center of the ultrasound array 1600. Once the centers are co-localized, the HIFU energy can be activated to create lesions along the length of the artery wall 1640, 1620, 1630 at different depths and positions around the artery. The natural focusing of the transducers positioned along a cylinder as in FIG. 17b is a lengthwise lesion, longer than in thickness or height, which will run along the length of an artery when the artery is placed along the center axis of the cylinder. When viewed along a cross section the nerve ablations are positioned along a clock face 1680 around the vessel.

Importantly, during treatment, a treatment workstation 1300 gives multiple views of the treatment zone with both physical appearance and anatomy 1050. Physical modeling is performed in order to predict lesion depth and the time to produce the lesion; this information is fed back to the ultrasound transducers 1100. The position of the lesion is also constantly monitored in a three dimensional coordinate frame and the transducer focus at lesions center 1150 continually updated.

In some embodiments, motion tracking prevents the lesion or patient from moving too far out of the treatment zone during the ablation. If the patient does move outside the treatment zone during the therapy, then the therapy can be stopped. Motion tracking can be performed using the ultrasound transducers, tracking frames and position or with transducers from multiple angles, creating a three dimensional image with the transducers. Alternatively, a video imaging system can be used to track patient movements, as can a series of accelerometers positioned on the patient which indicate movement.

Figure 18:
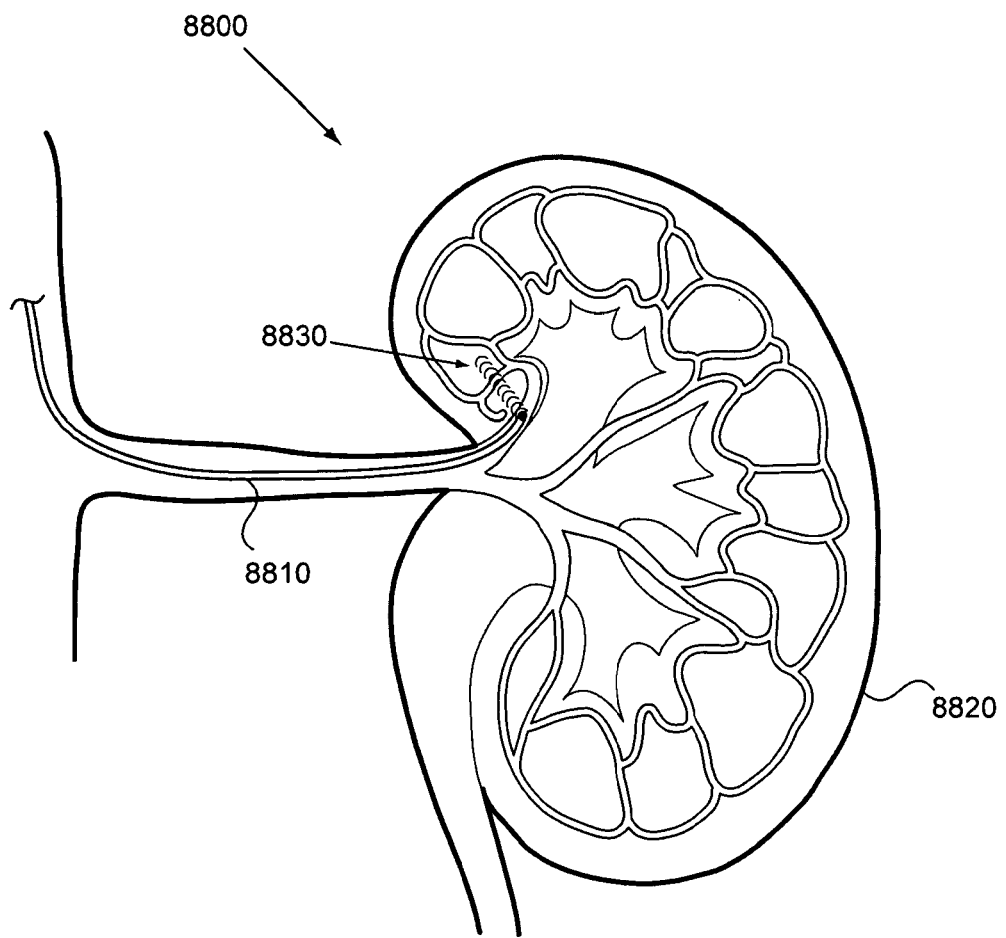
FIG. 18 depicts the application of energy internally within the kidney.

FIG. 18 depicts a micro-catheter 8810 which can be placed into renal calyces 8820; this catheter allows the operator to specifically ablate or stimulate 8830 regions of the kidney 8800. The catheter can be used to further allow for targeting of the region around the renal arteries and kidneys by providing additional imaging capability or by assisting in movement tracking or reflection of the ultrasound waves to create or position the lesion. The catheter or device at or near the end of the catheter may transmit signals outside the patient to direct an energy delivery device which delivers energy through the skin. Signaling outside the patient may comprise energies such as radiofrequency transmission outside the patient or radiofrequency from outside to the inside to target the region surrounding the catheter.

In one method, a micro catheter is delivered to the renal arteries and into the branches of the renal arteries in the kidney. A signal is generated from the catheter into the kidney and out of the patient to an energy delivery system. Based on the generated signal, the position of the catheter in a three dimensional coordinate reference is determined and the energy source is activated to deliver energy to the region indicated by the microcatheter. The microcatheter may be utilized to place a flow restrictor inside the kidney (e.g. inside a renal vein) to "trick" the kidney into thinking its internal pressure is higher than it might be. In this embodiment, the kidney generates signals to the central nervous system to lower sympathetic output to target organs.

Alternatively, specific regions of the kidney might be responsible for hormone excretion or other factors which lead to hypertension or other detrimental effects to the cardiovascular system. The microcatheter can generate ultrasound, radiofrequency, microwave, or X-ray energy. The microcatheter can be utilized to ablate regions in the renal vein or intraparenchymal venous portion as well. In some embodiments, ablation is not required but vibratory energy emanating from the probe is utilized to affect, on a permanent or temporary basis, the mechanoreceptors or chemoreceptors in the location of the hilum of the kidney.

Figure 19:
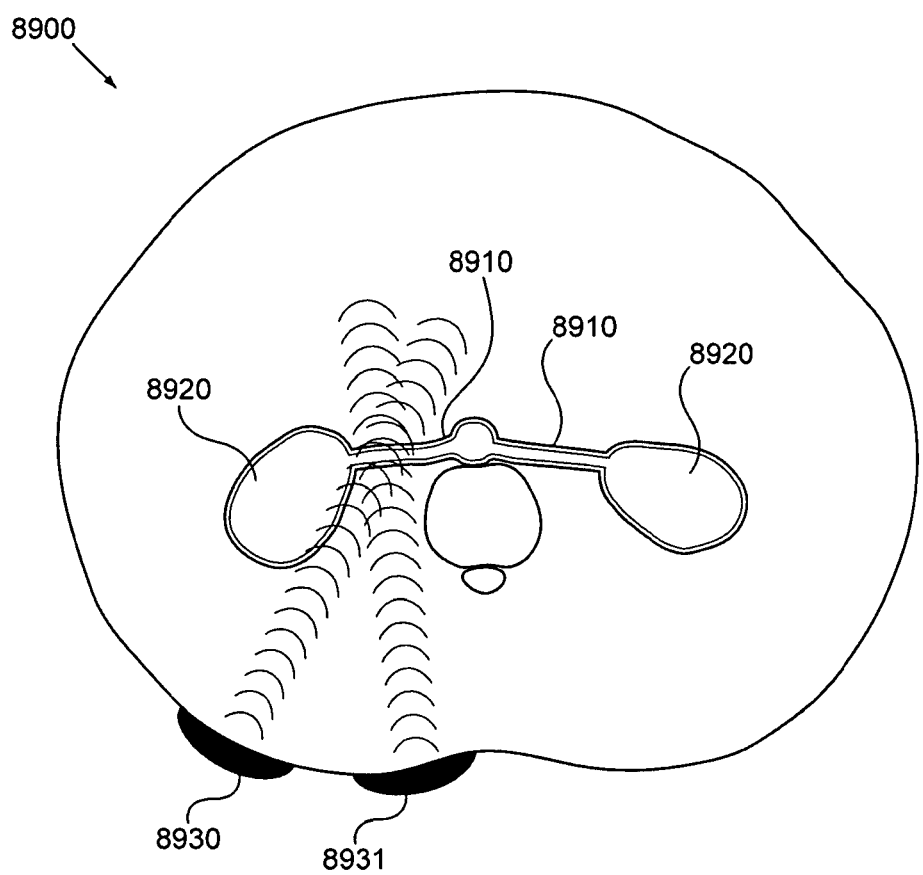
FIG. 19 depicts the direction of energy wave propagation to treat regions of the autonomic nervous system around the kidney region.

FIG. 19 depicts the application of acoustic waves to the region of the renal artery 8910 and kidney 8920 using physically separated transducers 8930, 8931. In contrast to the delivery method of FIG. 17, FIG. 19 depicts delivery of ultrasound transverse to the renal arteries and not longitudinal to the artery. The direction of energy delivery is the posterior of the patient because the renal artery is the first vessel seen when traveling from the skin toward the anterior direction facilitating delivery of the therapy. In one embodiment, the transducers 8930, 8931 are placed under, or inferior to the rib of the patient or between the ribs of a patient; next, the transducers apply an ultrasound wave propagating forward toward the anterior abdominal wall and image the region of the renal arteries and renal veins, separating them from one another. In some embodiments, such delivery might be advantageous, if for example, a longitudinal view of the artery is unobtainable or a faster treatment paradigm is desirable. The transducers 8930, 8931 communicate with one another and are connected to a computer model of the region of interest being imaged (ROI), the ROI based on an MRI scan performed just prior to the start of the procedure and throughout the procedure. Importantly, the transducers are placed posterior in the cross section of the patient, an area with more direct access to the kidney region. The angle between the imaging transducers is In another embodiment, an MRI is not performed but ultrasound is utilized to obtain all or part of the view in FIG. 19. For example, 8930 might contain an imaging transducer as well as a therapeutic energy source (e.g. ionizing energy, HIFU, low energy focused ultrasound, etc.).

Figure 20:
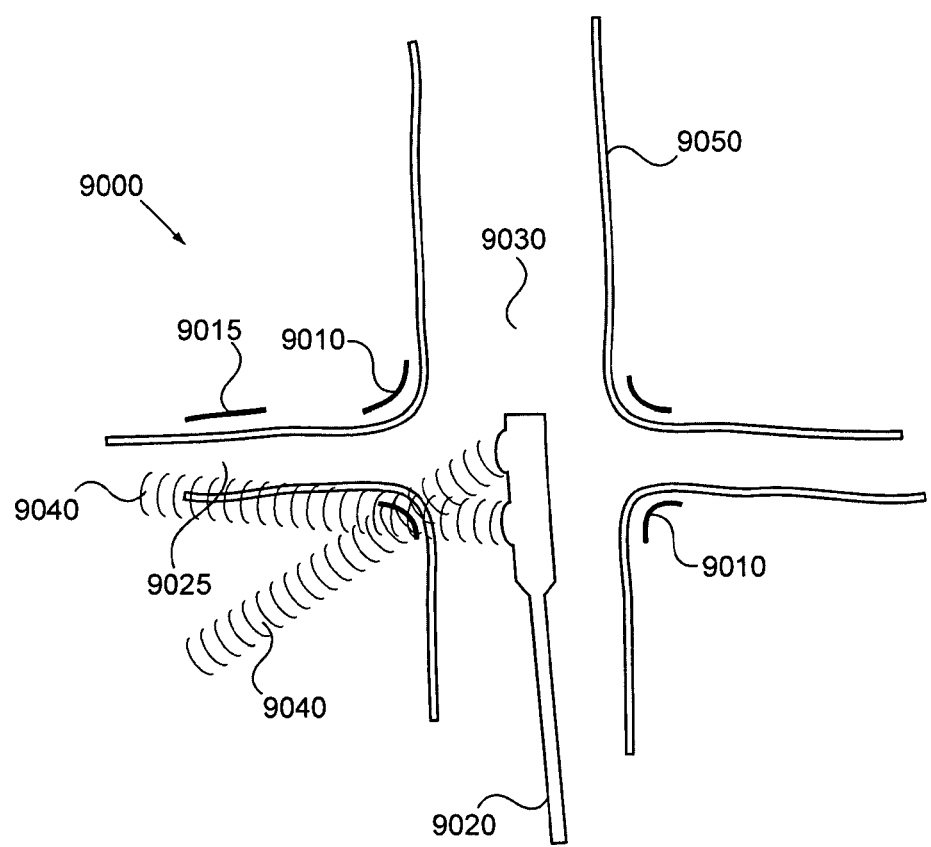
FIG. 20 depicts the application of ultrasound waves through the wall of the aorta

FIG. 20 depicts an alternative method 9000 and device to ablate the renal nerves 9015 or the nerves leading to the renal nerves at the aorta-renal artery ostium 9010. The intravascular device 9020 is placed into the aorta 9050 and advanced to the region of the renal arteries 9025. Energy is applied from the transducer 9020 and focused 9040 (in the case of HIFU, LIFU, ionizing radiation) to the region of the takeoff of the renal arteries 9025 from the aorta 9050. This intravascular procedure can be guided using MRI and/or MRI thermometry or it can be guided using fluoroscopy, ultrasound, or MRI. Because the aorta is larger than the renal arteries, the HIFU catheter can be placed into the aorta directly and cooling catheters can be included as well. In addition, in other embodiments, non-focused ultrasound can be applied to the region around the renal ostium or higher in the aorta. Non-focused ultrasound in some embodiments may require cooling of the tissues surrounding the probe using one or more coolants but in some embodiments, the blood of the aorta will take the place of the coolant; HIFU, or focused ultrasound, may not need the cooling because the waves are by definition focused from different angles to the region around the aorta. The vena cava and renal veins can also be used as a conduit for the focused ultrasound transducer to deliver energy to the region as well. In one embodiment, the vena cava is accessed and vibratory energy is passed through the walls of the vena cava and renal vein to the renal arteries, around which the nerves to the kidney travel. The veins, having thinner walls, allow energy to pass through more readily.

Figure 21A:
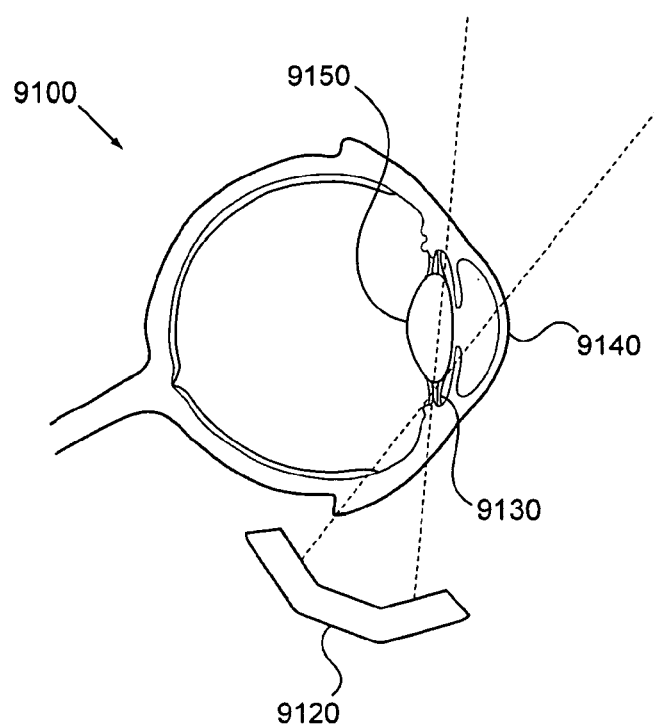
FIG. 21a depicts application of focused energy to the ciliary muscles and processes of the eye.
Figure 21B:
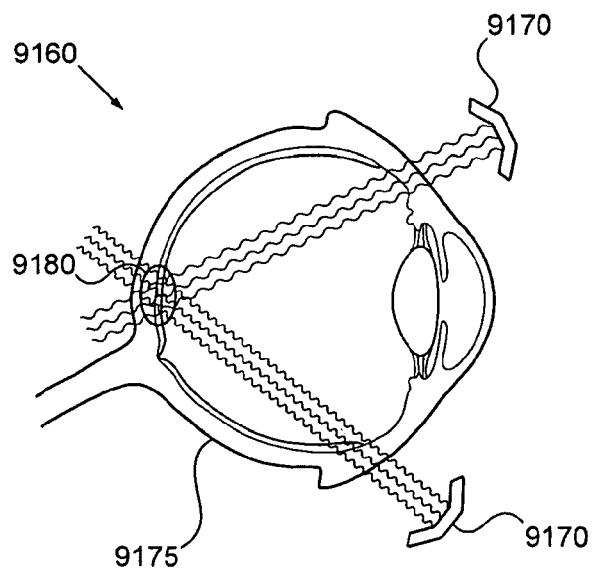
FIG. 21b depicts the application of focused non-ablative energy to the back of the eye to enhance drug or gene delivery or another therapy such as ionizing radiation.

FIG. 21 depicts an eyeball 9100. Also depicted are the zonules 9130 and ultrasound transducer 9120. The transducer 9120 applies focused ultrasound energy to the region surrounding the zonules, or the zonules themselves, in order to tighten them such that a presbyopic patient can accommodate and visualize object up close. Similarly, heat or vibration to the ciliary muscles, which then slows down the outflow of aqueous humor at the region of interest so that the pressure within the eye cannot build up to a high level. The ultrasound transducer 9120 can also be utilized to deliver drug therapy to the region of the lens, ciliary body, zonules, intravitreal cavity, anterior cavity, posterior cavity, etc.

In some embodiments (FIG. 21*b*), the ultrasonic transducers 9170 are focused on the particular region of the eye so that tissues along the path of the ultrasound are not damaged by the ultrasound and the focus region and region of effect is the position where the waves meet in the eye. In one embodiment, the transducers are directed through the pars plana region of the eye to target the macula 9180 at the posterior pole 9175 of the eye. This configuration might allow for heat, vibratory stimulation, drug delivery, gene delivery, augmentation of laser or ionizing radiation therapy, etc. In certain embodiments, focused ultrasound is not required and generic vibratory waves are transmitted through the eye at frequencies from 20 kHz to 10 MHz. Such energy may be utilized to break up clots in, for example, retinal venous or arterial occlusions which are creating ischemia in the retina. This energy can be utilized in combination with drugs utilized specifically for breaking up clots in the veins of the retina.

Figure 22:
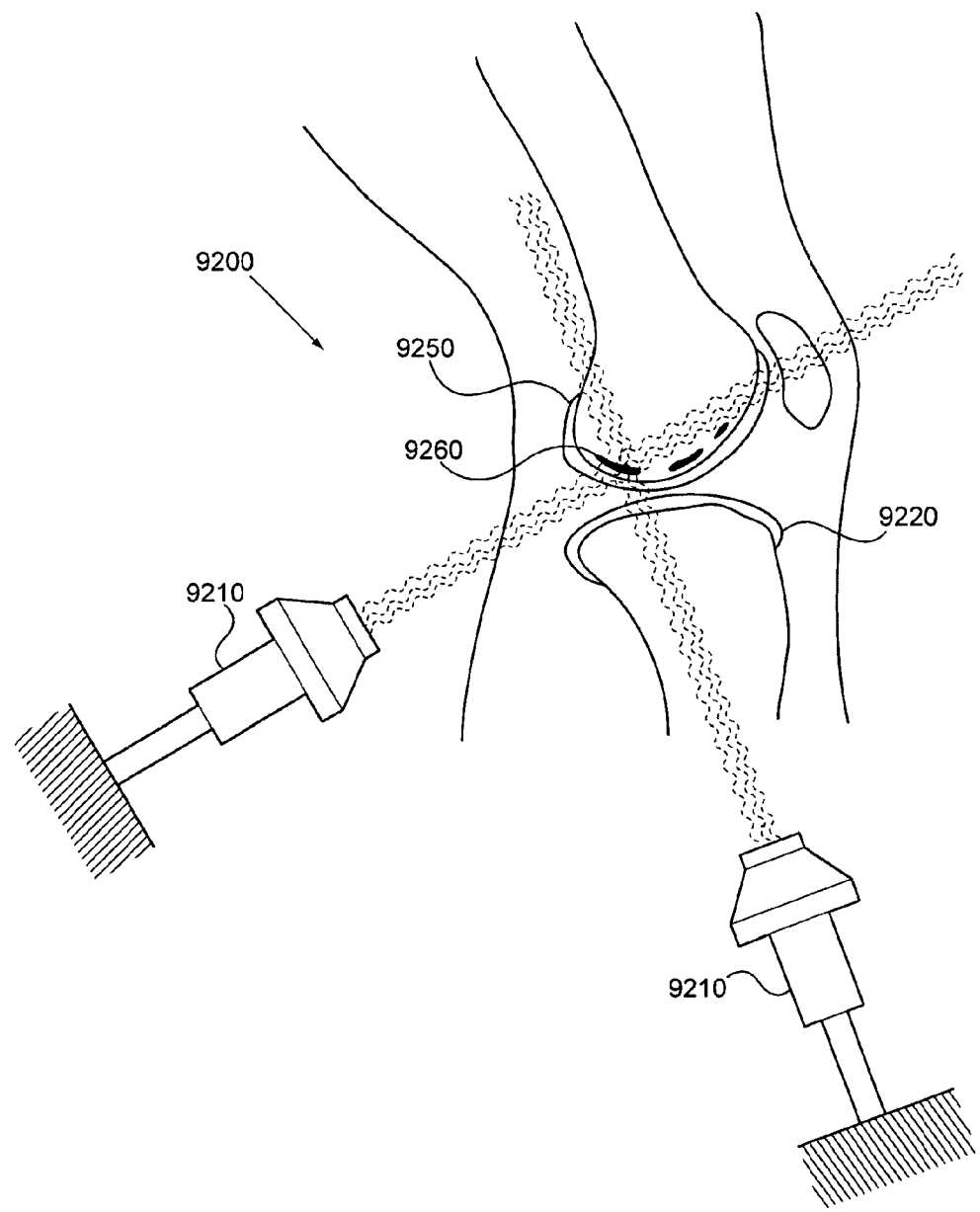
FIG. 22 depicts the application of focused energy to nerves surrounding the knee joint.

FIG. 22 depicts a peripheral joint 9200 being treated with heat and/or vibrational energy. Ultrasound transducer 9210 emits waves toward the knee joint to block nerves 9260 just underneath the bone periostium. Although a knee joint is depicted, it should be understood that many joints can be treated including small joints in the hand, intervertebral joints, the hip, the ankle, the wrist, and the shoulder. Unfocused or focused ultrasonic energy can be applied to the joint region to inhibit nerve function reversibly or irreversibly. Such inhibition of nerve function can be utilized to treat arthritis, post-operative pain, tendonitis, tumor pain, etc.

Figure 23A:
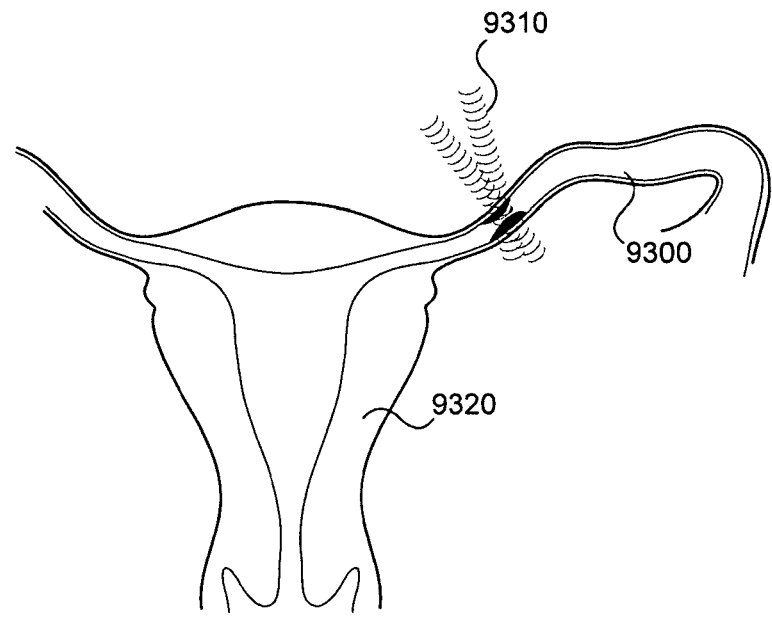
FIGS. 23a-23b depict the application of energy to the fallopian tube to sterilize a patient.
Figure 23B:
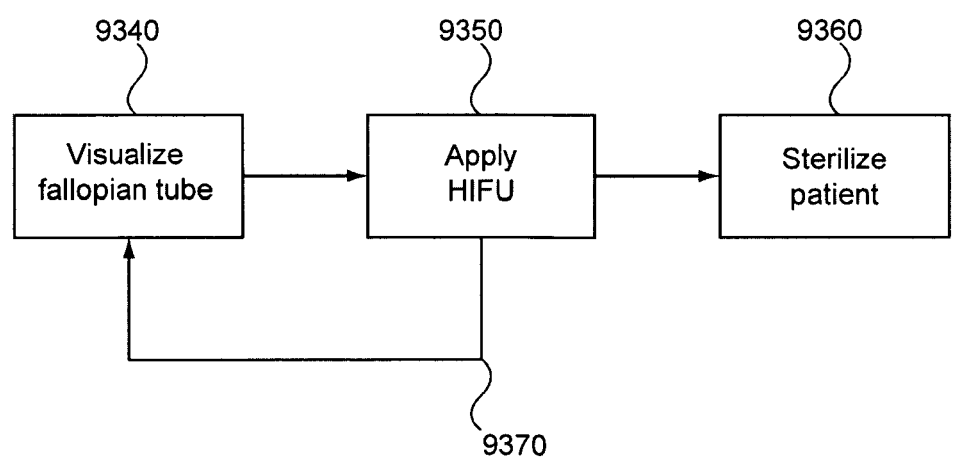
Figure 24:
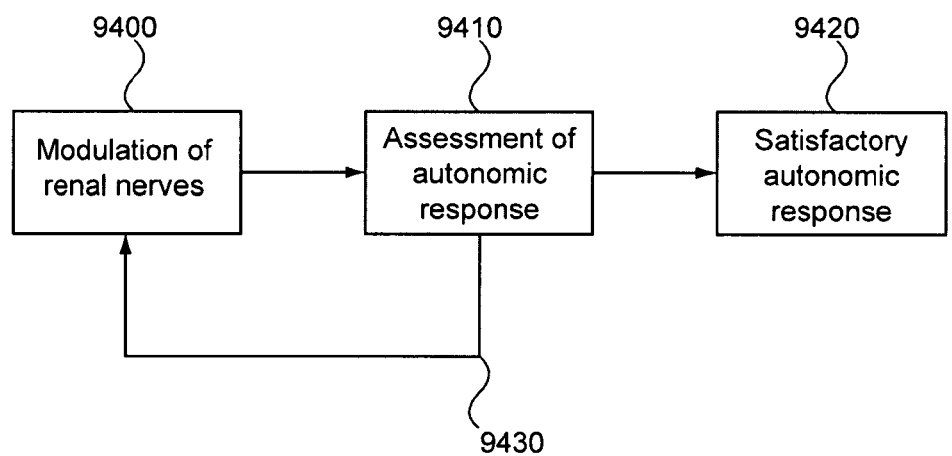
FIG. 24 depicts an algorithm to assess the effect of the neural modulation procedure on the autonomic nervous system. After a procedure is performed on the renal nerves, assessment of the autonomic response is performed by, for example, simulating the autonomic nervous system in one or more places.

FIG. 23*a-b* depicts closure of a fallopian tube 9300 of a uterus 9320 using externally applied ultrasound 9310 so as to prevent pregnancy. MRI or preferably ultrasound can be utilized for the imaging modality. Thermometry can be utilized as well so as to see the true ablation zone in real time. The fallopian tube 9300 can be visualized using ultrasound, MRI, CT scan or a laparoscope. Once the fallopian tube is targeted, external energy 9310, for example, ultrasound, can be utilized to close the fallopian tube to prevent pregnancy.

In other embodiments, ultrasound is applied to the uterus or fallopian tubes to aid in pregnancy by improving the receptivity of the sperm and/or egg for one another. This augmentation of conception can be applied to the sperm and egg outside of the womb as well, for example, in a test tube.

In 23*b* a method is depicted in which the fallopian tubes are visualized 9340 using MRI, CT, or ultrasound. HIFU 9350 is applied under visualization with MRI or ultrasound. As the fallopian tubes are heated, the collagen in the wall is heated until the walls of the fallopian tube close off. At this point the patient is sterilized 9360. During the treating time, it may be required to determine how effective the heating is progressing. If additional heat is required, then additional HIFU may be added to the fallopian tubes until there is closure of the tube and the patient is sterilized 9360.

The invention claimed is:

1. A method to inhibit a function of a nerve traveling to or from a kidney, comprising:
    identifying an acoustic window at a back of a body of a patient through which a hilum of the kidney can be imaged;
    transmitting a first energy through a skin of the patient from the back of the body of the patient;
    imaging the hilum of the kidney using the transmitted first energy to obtain an image; and
    applying a second energy to the hilum of the kidney that has been imaged.

2. The method of claim 1, further comprising tracking the hilum of the kidney using the image created by the first energy.

3. The method of claim 1, wherein the second energy is applied to at least partially inhibit the nerve traveling to or from the kidney.

4. The method of claim 1, wherein the first energy comprises ultrasound energy.

5. The method of claim 1, wherein the second energy comprises ultrasound energy.

6. A system to at least partially inhibit a function of a nerve traveling to or from a kidney, comprising:
    a first energy source configured for transmitting a first ultrasound energy from a back of a body of a patient through a skin of the patient;
    an imager configured for imaging a blood vessel using a transmitted first ultrasound energy to obtain an image; and
    a second energy source configured to apply a second ultrasound energy to an adventitial region of the blood vessel region that has been imaged using the first ultrasound energy, the second ultrasound energy being focused ultrasound energy.

7. The system of claim 6, further comprising a processing unit configured for tracking the blood vessel using the image created by the first ultrasound energy.

8. The system of claim 6, further comprising a processing unit executing a modeling algorithm with an input and an output, the input comprising a three dimensional coordinate space and a representation of the second energy source.

9. The system of claim 8, wherein the output of the modeling algorithm comprises an energy level.

10. The system of claim 9, wherein the output of the modeling algorithm further comprises a direction of the second ultrasound energy.

11. The system of claim 6, wherein the imager is configured to image an intravascular catheter.

12. The system of claim 6, further comprising a processing unit configured to determine phase and power output for the second energy source in dependence on an image provided by the imager.

13. The system of claim 6, further comprising a processing unit configured to receive an input regarding error in position of the focused ultrasound energy.

14. The system of claim 6, further comprising a processing unit coupled to the second energy source, wherein the processing unit is configured to receive input regarding lesion size in an ablation zone.

15. The system of claim 6, further comprising a processing unit configured to:
    obtain an error variable;
    use the error variable to create a representation of temperature and position, and their associated errors, and
    use the representation to create a map.

16. The system of claim 6, further comprising a processing unit configured to determine a baseline position for the energy source, and one or more positions of the blood vessel with respect to the baseline.

17. The system of claim 16, wherein the processing unit is configured to update a target of the energy source in dependence on a difference between the one or more positions and the baseline position.

18. The system of claim 17, wherein a frequency of the updates is greater than 50 Hertz.

19. The system of claim 16, wherein the one or more positions of the blood vessel are determined using an intravascular targeting catheter.

20. The system of claim 6, further comprising a processing unit executing a targeting algorithm for tracking the adventitial region of the blood vessel.

* * * * *